United States Patent
Raats et al.

(10) Patent No.: US 10,233,236 B2
(45) Date of Patent: *Mar. 19, 2019

(54) METHOD OF TREATING OR PREVENTING RHEUMATOID ARTHRITIS

(71) Applicant: MODIQUEST B.V., Oss (NL)

(72) Inventors: Jozef Maria Hendrik Raats, Nijmegen (NL); Renato Gerardus Silvano Chirivi, Oosterhout (NL)

(73) Assignee: Modiquest B.V., Oss (NL)

( * ) Notice: Subject to any disclaimer, the term of this patent is extended or adjusted under 35 U.S.C. 154(b) by 254 days.

This patent is subject to a terminal disclaimer.

(21) Appl. No.: 14/742,990

(22) Filed: Jun. 18, 2015

(65) Prior Publication Data

US 2015/0307603 A1    Oct. 29, 2015

Related U.S. Application Data

(62) Division of application No. 13/514,923, filed as application No. PCT/EP2010/069431 on Dec. 10, 2010, now Pat. No. 9,109,019.

(30) Foreign Application Priority Data

Dec. 10, 2009    (EP) .................................... 09178658

(51) Int. Cl.

| | | |
|---|---|---|
| *C07K 16/44* | (2006.01) | |
| *C07K 16/18* | (2006.01) | |
| *A61K 39/00* | (2006.01) | |

(52) U.S. Cl.
CPC .............. *C07K 16/18* (2013.01); *C07K 16/44* (2013.01); *A61K 2039/505* (2013.01); *C07K 2317/21* (2013.01); *C07K 2317/34* (2013.01); *C07K 2317/56* (2013.01); *C07K 2317/565* (2013.01); *C07K 2317/622* (2013.01)

(58) Field of Classification Search
None
See application file for complete search history.

(56) References Cited

U.S. PATENT DOCUMENTS

2012/0321631 A1    12/2012    Raats

FOREIGN PATENT DOCUMENTS

| WO | 98/22503 | 5/1998 |
|---|---|---|
| WO | 2004078098 A2 | 9/2004 |
| WO | 2009147201 A2 | 12/2009 |
| WO | 2011070172 A1 | 6/2011 |

OTHER PUBLICATIONS

Biol., Chem., 2001; 276(39):36687-36694.
Kuna et al., Antibodies to Mutated Citrullinated Vimentin and Antibodies to Cyclic Citrullinated Peptides and Juvenile Idiopathic Arthritis; Clinical Chemistry and Laboratory Medicine, vol. 47 No. 12; Oct. 21, 2009; pp. 1525-1530.
Narayanan et al., Long-term Follow Up of Infliximab Therapy in Inflammatory Arthritis; Indian Journal of Rheumatology, vol. 2 No. 1; Mar. 1, 2007; pp. 8-10.
Neeli et al., Histone Deimination as a Response to Inflammatory Stimuli in Neutrophils, The Journal of Immunology; Feb. 1, 2008; vol. 180 No. 3; pp. 1895-1902.
Raats et al., Recombinant Human Monoclonal Auto Antibodies Specific for Citrulline-containing Peptides from Phage Display Libraries Derived from Patients with Rheumatoid Arthritis, The Journal of Rheumatology; Aug. 1, 2003; pp. 1696-1711.
Sebbag et al.;, Epitopes of Human Fibrin Recognized by the Rheumatoid Arthritis-specific Auto Antibodies to Citrullinated Proteins;, European Journal of Immunology; Aug. 2006, vol. 36 No. 8; pp. 2250-2263.
Verpoort et al., Fine Specifiity of the Anti-Citrullinated Protein Antibody Response is Influenced by the Shared Epitope Alleles; Arthritis and Rheumatism, vol. 56 No. 12; Dec. 2007; pp. 3949-3952.
Wager et al., Antibody Against Mutated Citrullinated Vimentin: A New Sensitive Marker in the Diagnosis of Rheumatory Arthritis; Rheumatology International;, vol. 29 No. 11; Jan. 28, 2009; pp. 1315-1321.
De Pascalis, R., et al. J Immunol. 2002;169:3076-3084.
Lamminmaki, U., et al. J. Biol. Chem. 2001;276(39):36687-36694.

*Primary Examiner* — G. R. Ewoldt
(74) *Attorney, Agent, or Firm* — Patent Law Works LLP

(57) ABSTRACT

This invention is in the field of treating or preventing rheumatoid arthritis in humans and animals. In particular, the invention relates to methods for treating or preventing rheumatoid arthritis through treatment with an antibody which specifically reacts with a citrullinated epitope present on a peptide with an amino acid sequence according to SEQ ID NO:21.

4 Claims, 26 Drawing Sheets

Specification includes a Sequence Listing.

SEQUENCE LISTING

```
<160> NUMBER OF SEQ ID NOS: 45

<210> SEQ ID NO 1
<211> LENGTH: 17
<212> TYPE: PRT
<213> ORGANISM: Mus musculus

<400> SEQUENCE: 1

Lys Ala Met Gly Ile Met Asn Ser Phe Val Asn Asp Ile Phe Glu Arg
1               5                   10                  15

Ile

<210> SEQ ID NO 2
<211> LENGTH: 12
<212> TYPE: PRT
<213> ORGANISM: Mus musculus

<400> SEQUENCE: 2

Arg Lys Glu Ser Tyr Ser Ile Tyr Val Tyr Lys Val
1               5                   10

<210> SEQ ID NO 3
<211> LENGTH: 17
<212> TYPE: PRT
<213> ORGANISM: Bos Taurus

<400> SEQUENCE: 3

Lys Ala Met Gly Ile Met Asn Ser Phe Val Asn Asp Ile Phe Lys Arg
1               5                   10                  15

Ile
```

-continued

<210> SEQ ID NO 4
<211> LENGTH: 17
<212> TYPE: PRT
<213> ORGANISM: Bos Taurus

<400> SEQUENCE: 4

Lys Ala Met Gly Asn Met Asn Ser Phe Val Asn Asp Ile Phe Glu Arg
1               5                   10                  15

Ile

<210> SEQ ID NO 5
<211> LENGTH: 15
<212> TYPE: PRT
<213> ORGANISM: Rattus norvegicus

<400> SEQUENCE: 5

Arg Lys Thr Val Thr Ala Met Asp Val Val Tyr Ala Leu Lys Arg
1               5                   10                  15

<210> SEQ ID NO 6
<211> LENGTH: 12
<212> TYPE: PRT
<213> ORGANISM: Rattus norvegicus

<400> SEQUENCE: 6

Arg Asp Ala Val Thr Tyr Thr Glu His Ala Lys Arg
1               5                   10

<210> SEQ ID NO 7
<211> LENGTH: 12
<212> TYPE: PRT
<213> ORGANISM: Rattus norvegicus

<400> SEQUENCE: 7

Arg Ile Ser Gly Leu Ile Tyr Glu Glu Thr Arg Gly
1               5                   10

<210> SEQ ID NO 8
<211> LENGTH: 1431
<212> TYPE: DNA
<213> ORGANISM: homo sapiens

<400> SEQUENCE: 8

```
atgggatgga gctgtatcat cctcttcttg gtagcaacag ctacaggtgt gcattcccag      60
gtacagctgc agcagtcagg gggaggcctg gtcaggccgg ggggtccct gagactctcc      120
tgtgcagcct ccggattcaa cctcagcacc aattttatga actgggtccg ccagagtcga      180
gggaaggggc tggagtggat ctcatccatt agttggactg gtgatgatat atatgaggca      240
gactcactga agggccgatt caccgtctcc agagacaacg ccaagaacac agtgtatctg      300
caactgagca gcctgacacc ggacgacacg gctgtctatt actgtgcgag agtgcgccag      360
tatcgtgatg gtaggggta tgtcgttaat gacgctcttg atatttgggg ccaagggaca      420
atggtcaccg tgtcgtcagc ctccaccaag ggcccatcgg tcttcccct ggcaccctcc       480
tccaagagca cctctggggg cacagcggcc ctgggctgcc tggtcaagga ctacttcccc      540
gaaccggtga cggtgtcgtg gaactcaggc gccctgacca gcggcgtgca cacctteccg      600
gctgtcctac agtcctcagg actctactcc ctcagcagcg tggtgaccgt gccctccagc      660
agcttgggca cccagaccta catctgcaac gtgaatcaca agcccagcaa caccaaggtg      720
gacaagaaag ttgagcccaa atcttgtgac aaaactcaca catgcccacc gtgcccagca      780
```

```
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctacag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaatg a            1431

<210> SEQ ID NO 9
<211> LENGTH: 705
<212> TYPE: DNA
<213> ORGANISM: homo sapiens

<400> SEQUENCE: 9
atgggatgga gctgtatcat cctcttcttg gtagcaacag ctacaggtgt gcattcccag     60
tctgtgttga ctcagccgcc ctcaatgtct gcggccccag gacagaaggt cacgatctcc    120
tgctctggaa gcagctccaa cattggcaat aattatgtat cctggtatca gcaagtccca    180
ggaacagccc ccaaactcct catttatgac gacaataaga gaccctccgg aattcccggc    240
cgattctctg gctccaagtc tgccacgtcc gccaccctgg gcatcaccgg actccaggct    300
ggggacgagg ccgattatta ctgcggatca tgggatgata acctgagtgt tgtgcttttc    360
ggcggaggga ccaagctgac cgtcctaggt cagcccaagg ctgccccctc ggtcactctg    420
ttcccgccct cctctgagga gcttcaagcc aacaaggcca cactggtgtg tctcataagt    480
gacttctacc cgggagccgt gacagtggcc tggaaggcag atagcagccc cgtcaaggcg    540
ggagtggaga ccaccacacc ctccaaacaa agcaacaaca gtacgcggc cagcagctat    600 ctgagcctga cgcctgagca gtggaagtcc cacagaagct acagctgcca ggtcacgcat    660
gaagggagca ccgtggagaa gacagtggcc cctacagaat gttca                   705

<210> SEQ ID NO 10
<211> LENGTH: 699
<212> TYPE: DNA
<213> ORGANISM: homo sapiens

<400> SEQUENCE: 10
atgggatgga gctgtatcat cctcttcttg gtagcaacag ctacaggtgt gcattccgac     60
atccagatga cccagtctcc atcctccctg tctgcatctg taggagacag aatcaccatc    120
acttgccggg caagtcagag cattagcaac tatttaaatt ggtatcagca gaaaccaggg    180
aaagtcccta agctcctgat ctatgctgca tccagcttgc aaagtggggt cccagcaagg    240
ttcagtggca gtggatctgg gacagatttc agtctcacca tcagcagtct gcaacctgaa    300
gatttcgcaa cttactactg tcaacagagt tacagtaccc ctctgacttt cggcggaggg    360
accaaggtgg aaatcaaacg aactgtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
```

```
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgt                             699
```

<210> SEQ ID NO 11
<211> LENGTH: 321
<212> TYPE: DNA
<213> ORGANISM: homo sapiens

<400> SEQUENCE: 11

```
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                                321
```

<210> SEQ ID NO 12
<211> LENGTH: 19
<212> TYPE: PRT
<213> ORGANISM: Mus musculus

<400> SEQUENCE: 12

Met Gly Trp Ser Cys Ile Ile Leu Phe Leu Val Ala Thr Ala Thr Gly
1               5                   10                  15

Val His Ser

<210> SEQ ID NO 13
<211> LENGTH: 127
<212> TYPE: PRT
<213> ORGANISM: homo sapiens

<400> SEQUENCE: 13

Gln Val Gln Leu Gln Gln Ser Gly Gly Gly Leu Val Arg Pro Gly Gly
1               5                   10                  15

Ser Leu Arg Leu Ser Cys Ala Ala Ser Gly Phe Asn Leu Ser Thr Asn
            20                  25                  30

Phe Met Asn Trp Val Arg Gln Ser Arg Gly Lys Gly Leu Glu Trp Ile
        35                  40                  45

Ser Ser Ile Ser Trp Thr Gly Asp Asp Ile Tyr Glu Ala Asp Ser Leu
    50                  55                  60

Lys Gly Arg Phe Thr Val Ser Arg Asp Asn Ala Lys Asn Thr Val Tyr
65                  70                  75                  80

Leu Gln Leu Ser Ser Leu Thr Pro Asp Asp Thr Ala Val Tyr Tyr Cys
                85                  90                  95

Ala Arg Val Arg Gln Tyr Arg Asp Gly Arg Gly Tyr Val Val Asn Asp
            100                 105                 110

Ala Leu Asp Ile Trp Gly Gln Gly Thr Met Val Thr Val Ser Ser
        115                 120                 125

<210> SEQ ID NO 14
<211> LENGTH: 330
<212> TYPE: PRT
<213> ORGANISM: homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 110
<212> TYPE: PRT
<213> ORGANISM: homo sapiens

<400> SEQUENCE: 15

Gln Ser Val Leu Thr Gln Pro Pro Ser Met Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Val Pro Gly Thr Ala Pro Lys Leu Leu

```
            35                  40                  45
Ile Tyr Asp Asp Asn Lys Arg Pro Ser Gly Ile Pro Gly Arg Phe Ser
 50                  55                  60
Gly Ser Lys Ser Ala Thr Ser Ala Thr Leu Gly Ile Thr Gly Leu Gln
 65                  70                  75                  80
Ala Gly Asp Glu Ala Asp Tyr Tyr Cys Gly Ser Trp Asp Asn Leu
                 85                  90                  95
Ser Val Val Leu Phe Gly Gly Gly Thr Lys Leu Thr Val Leu
            100                 105                 110

<210> SEQ ID NO 16
<211> LENGTH: 106
<212> TYPE: PRT
<213> ORGANISM: homo sapiens

<400> SEQUENCE: 16

Gly Gln Pro Lys Ala Ala Pro Ser Val Thr Leu Phe Pro Pro Ser Ser
 1               5                  10                  15
Glu Glu Leu Gln Ala Asn Lys Ala Thr Leu Val Cys Leu Ile Ser Asp
                20                  25                  30
Phe Tyr Pro Gly Ala Val Thr Val Ala Trp Lys Ala Asp Ser Ser Pro
            35                  40                  45
Val Lys Ala Gly Val Glu Thr Thr Thr Pro Ser Lys Gln Ser Asn Asn
 50                  55                  60
Lys Tyr Ala Ala Ser Ser Tyr Leu Ser Leu Thr Pro Glu Gln Trp Lys
 65                  70                  75                  80
Ser His Arg Ser Tyr Ser Cys Gln Val Thr His Glu Gly Ser Thr Val
                85                  90                  95
Glu Lys Thr Val Ala Pro Thr Glu Cys Ser
            100                 105

<210> SEQ ID NO 17
<211> LENGTH: 330
<212> TYPE: DNA
<213> ORGANISM: homo sapiens

<400> SEQUENCE: 17
cagtctgtgt tgacgcagcc gccctcaatg tctgcggccc caggacagaa ggtcacgatc    60
tcctgctctg gaagcagctc caacattggc aataattatg tatcctggta tcagcaagtc   120
ccaggaacag cccccaaact cctcatttat gacgacaata agagaccctc cggaattccc   180
ggccgattct ctggctccaa gtctgccacg tccgccaccc tgggcatcac cggactccag   240
gctgggacg aggccgatta ttactgcgga tcatgggatg ataacctgag tgttgtgctt   300
ttcggcggag ggaccaagct gaccgtccta                                    330

<210> SEQ ID NO 18
<211> LENGTH: 381
<212> TYPE: DNA
<213> ORGANISM: homo sapiens

<400> SEQUENCE: 18
caggtacagc tgcagcagtc aggggggaggc ctggtcaggc cggggggtc cctgagactc     60
tcctgtgcag cctccggatt caacctcagc accaatttta tgaactgggt ccgccagagt   120
cgagggaagg ggctggagtg gatctcatcc attagttgga ctggtgatga tatatatgag   180
gcagactcac tgaagggccg attcaccgtc tccagagaca acgccaagaa cacagtgtat   240
```

-continued

```
ctgcaactga gcagcctgac accggacgac acggctgtct attactgtgc gagagtgcgc      300
cagtatcgtg atggtagggg gtatgtcgtt aatgacgctc ttgatatttg gggccaaggg      360
acaacggtca ccgtgtcgtc a                                                381
```

<210> SEQ ID NO 19
<211> LENGTH: 330
<212> TYPE: DNA
<213> ORGANISM: homo sapiens

<400> SEQUENCE: 19

```
cagtctgtgt tgacgcagcc gccctccgtg tctgcgaccc caggacagaa ggtctccatc       60
tcctgctctg gaagcggcgc caacattggc aatacttatg tctcctggta ccaacaactc      120
ccaggatcag cccccaaact cctcatttac gacgataatc agcgaccctc tgggattcct      180
gaccgattct ctggcgccaa gtctggcacg tcagccaccc tgggcatcgc cgggctccag      240
actggggacg aggccgacta tttctgcgga gcatgggaca gtagcctgag tgcttttgtc      300
ttcggatctg ggacccagct caccgtttta                                       330
```

<210> SEQ ID NO 20
<211> LENGTH: 366
<212> TYPE: DNA
<213> ORGANISM: homo sapiens

<400> SEQUENCE: 20

```
caggtgcagc tgcaggagtc tggcccaggg gtggtgaagc cttcggagac gctgtctcta       60
acctgcaatg tctccggtga ctccatcagt gatggctact actggggctg gatccggcag      120
cccccaggga ggggactgga gtggattgga agtgtctatt ataatcgaaa caccttctac      180
aattcgtccc tcgagagtcg agtcagtctt tcacttgaca cttccaagaa ccacctctcc      240
ctgacgatga gcgatgtgac cgccgcagac acagccgttt atttctgttc gagagggcga      300
tccaaatttg gtccaaatga tgcttttgaa atttggggcc aagggaccac ggtcaccgtg      360
tcgtca                                                                 366
```

<210> SEQ ID NO 21
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 21

```
Ala Ala Ala Ser Gly Xaa Gly Lys Gln Gly Gly Lys
1               5                   10
```

<210> SEQ ID NO 22
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 22

```
Ala Lys Ala Lys Ser Xaa Ser Ser Arg Ala Gly Leu
1               5                   10
```

```
<210> SEQ ID NO 23
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 23

Lys Ser Arg Ser Ser Xaa Ala Gly Leu Gln Phe Pro
1               5                   10

<210> SEQ ID NO 24
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 24

Gln Phe Pro Val Gly Xaa Val His Arg Leu Leu Arg
1               5                   10

<210> SEQ ID NO 25
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 25

Val Gly Arg Val His Xaa Leu Leu Arg Lys Gly Asn
1               5                   10

<210> SEQ ID NO 26
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 26

Val His Arg Leu Leu Xaa Lys Gly Asn Tyr Ser Glu
1               5                   10

<210> SEQ ID NO 27
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 27

Gly Asn Tyr Ser Glu Xaa Val Gly Ala Gly Ala Pro
1               5                   10

<210> SEQ ID NO 28
<211> LENGTH: 12
<212> TYPE: PRT
<213> ORGANISM: homo sapiens
```

```
<220> FEATURE:
<221> NAME/KEY: MISC_FEATURE
<222> LOCATION: (6)..(6)
<223> OTHER INFORMATION: X = citrulline

<400> SEQUENCE: 28

Ala Gly Asn Ala Ala Xaa Asp Asn Lys Lys Thr Arg
1               5                   10

<210> SEQ ID NO 29
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 29

Asp Asn Lys Lys Thr Xaa Ile Ile Pro Arg His Leu
1               5                   10

<210> SEQ ID NO 30
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 30

Thr Arg Ile Ile Pro Xaa His Leu Gln Leu Ala Ile
1               5                   10

<210> SEQ ID NO 31
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 31

Leu Gln Leu Ala Ile Xaa Asn Asp Glu Glu Leu Asn
1               5                   10

<210> SEQ ID NO 32
<211> LENGTH: 12
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: X = citrulline

<400> SEQUENCE: 32

Asn Lys Leu Leu Gly Xaa Val Thr Ile Ala Gln Gly
1               5                   10

<210> SEQ ID NO 33
<211> LENGTH: 22
<212> TYPE: PRT
<213> ORGANISM: homo sapiens
<220> FEATURE:
<221> NAME/KEY: MISC_FEATURE
<222> LOCATION: (15)..(17)
<223> OTHER INFORMATION: X = citrulline
```

<400> SEQUENCE: 33

Leu Ser Glu Gly Gly Gly Val Arg Gly Pro Arg Val Val Glu Xaa His
1               5                   10                  15

Xaa Ser Gln Cys Lys Asp
            20

<210> SEQ ID NO 34
<211> LENGTH: 22
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: X = citrulline

<400> SEQUENCE: 34

Leu Ser Glu Gly Gly Gly Val Xaa Gly Pro Arg Val Val Glu Arg His
1               5                   10                  15

Gln Ser Gln Cys Lys Asp
            20

<210> SEQ ID NO 35
<211> LENGTH: 22
<212> TYPE: PRT
<213> ORGANISM: homo sapiens
<220> FEATURE:
<221> NAME/KEY: MISC_FEATURE
<222> LOCATION: (15)..(15)
<223> OTHER INFORMATION: X = citrulline

<400> SEQUENCE: 35

Leu Ala Glu Gly Gly Gly Val Arg Gly Pro Arg Val Val Glu Xaa His
1               5                   10                  15

Gln Ser Ala Cys Lys Asp
            20

<210> SEQ ID NO 36
<211> LENGTH: 22
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: X = citrulline

<400> SEQUENCE: 36

Leu Ala Glu Gly Gly Gly Val Xaa Gly Pro Arg Val Val Glu Arg His
1               5                   10                  15

Gln Ser Ala Cys Lys Asp
            20

<210> SEQ ID NO 37
<211> LENGTH: 17
<212> TYPE: PRT
<213> ORGANISM: homo sapiens
<220> FEATURE:
<221> NAME/KEY: MISC_FEATURE
<222> LOCATION: (9)..(9)
<223> OTHER INFORMATION: X = citrulline

<400> SEQUENCE: 37

Glu Pro Thr Asp Ser Leu Asp Ala Xaa Gly His Arg Pro Val Asp Arg
1               5                   10                  15

Arg

<210> SEQ ID NO 38
<211> LENGTH: 15
<212> TYPE: PRT
<213> ORGANISM: homo sapiens
<220> FEATURE:
<221> NAME/KEY: MISC_FEATURE
<222> LOCATION: (4)..(11)
<223> OTHER INFORMATION: X = citrulline

<400> SEQUENCE: 38

Tyr Val Thr Xaa Ser Ser Ala Val Xaa Leu Xaa Ser Ser Val Pro
1               5                   10                  15

<210> SEQ ID NO 39
<211> LENGTH: 330
<212> TYPE: DNA
<213> ORGANISM: homo sapiens

<400> SEQUENCE: 39
cagtctgtgt tgacgcagcc gccctcagcg tctgggaccc ccggacagag cgtcaccatc        60
tcttgttctg ggggcgactc caacatcggg gcgaatcatg taatctggta ccaccaaatc       120
ccacaaatgg cccccaaact gctcgtccat actagtgatc accggccctc aggggtccct       180
gagcgattct ctggttccaa gtctggcacg tcagcctccc tggccatcac tgggctccag       240
tctgaggatg acgtgatta ttactgttca gcttgggatg acaatctcag tggctggaca        300
ttcggcggag ggaccaagct gaccgtccta                                        330

<210> SEQ ID NO 40
<211> LENGTH: 354
<212> TYPE: DNA
<213> ORGANISM: homo sapiens

<400> SEQUENCE: 40
caggtgcagc tggtgcagtc tggggctgag gtgaggaagc ctggggcctc agttaaggtc        60
tcctgtaagg cttcgggtta cagatttgcc agctacggta tcaactgggt gcgacaggcc       120
cctggacaag gcttgagtg gatgggatgg atcggcggtt acactggtta cacagactat        180
gcacagaagt tcgaggacag aatcaacatg accacagaca catccacgac acagtttac        240 atggagctga ggagcctgag aactgacgac acagccgtat actattgtac gaggggaatt       300
gggccttccc cgatggacgc ctggggccaa gggaccacgg tcaccgtgtc gtca             354

<210> SEQ ID NO 41
<211> LENGTH: 321
<212> TYPE: DNA
<213> ORGANISM: homo sapiens

<400> SEQUENCE: 41
gacatccaga tgacccagtc tccatcctcc ctgtctgcat ctgtaggaga cagaatcacc        60
atcacttgcc gggcaagtca gagcattagc aactatttaa attggtatca gcagaaacca       120
gggaaagtcc ctaagctcct gatctatgct gcatccagct tgcaaagtgg ggtcccagca       180
aggttcagtg gcagtggatc tgggacagat ttcagtctca ccatcagcag tctgcaacct       240
gaagatttcg caacttacta ctgtcaacag agttacagta cccctctgac tttcggcgga       300
gggaccaagg tggaaatcaa a                                                 321

<210> SEQ ID NO 42
<211> LENGTH: 369

<212> TYPE: DNA
<213> ORGANISM: homo sapiens

<400> SEQUENCE: 42

```
gaggtgcagc tggtggagtc tggcccagga ctggtgaagt cttcggagac cctgtctctc      60
acctgccatg tctccggtta ctccatcagc gatggttact actggggctg gatccggcag     120
tccccaggga agggactgga gtggattggg agtaggcatc atgggggaa cgccaccttc      180
tacaatccgt cacacaagag tcgagtcagc ctcttaattg acacctccaa gaaccagttg     240
tccctgaaga tgcactctgt gaccgccgca gacacggcca tttactactg tgcgagaggg     300
cttcatatcg atggttggaa cgatgctttt gagatctggg gccagggac cacggtcacc      360
gtgtcgtca                                                             369
```

<210> SEQ ID NO 43
<211> LENGTH: 330
<212> TYPE: DNA
<213> ORGANISM: homo sapiens

<400> SEQUENCE: 43

```
tcctatgtgc tgactcagcc accctcaacg tctgggaccc ccgggcagag ggtcaccatc      60
tcttgttctg gaggcttctc caacatcgga cttaataatg taaactggta tcagcaactc     120
ccagaaacgg cccccaaact cctcatctat agtagtgatc agcggccctc aggggtccct     180
gaccgattct ctggctccaa gtctggcacc tcagcctccc tggccatcag tgggctccgg     240
tccgaggatg aggctgatta ttactgtgca gcatgggatg acagcctgag tggttgggtg      300
ctcggcggag gaaccaagct gaccgtccta                                      330
```

<210> SEQ ID NO 44
<211> LENGTH: 367
<212> TYPE: DNA
<213> ORGANISM: Mus musculus

<400> SEQUENCE: 44

```
cggatccagt tggtgcagtc tggacctgaa ctgaagaagc ctggtgaggc agtcaagatc      60
tcctgtaagg cttctggata taccttcaca aactatggta tgcactggat gaaacagact     120
ccaggaaagg attttaggtg gatgggctgg ataaacacct acagtggaga ggcaacatat     180
gttgatgact tcaagggacg cttcgccttc tctttgggaa cctctgccag cactgcctat     240
ttgcagatca acaacctcaa gaatgacgac acggctacat atttctgttt aagaggctat     300
acttaccaaa gtttcgacga aggggcgac tactggggcc agggcaccgc tctcacagtc      360
tcctcag                                                               367
```

<210> SEQ ID NO 45
<211> LENGTH: 338
<212> TYPE: DNA
<213> ORGANISM: mus musculus

<400> SEQUENCE: 45

```
gatgttgtga tgacccagac tccactcact ttgtcggtta ccactggaca accagcctcc      60
atctcttgca gtcaagtca gagcctcttg gatagtgatg gaaagacata tttgaattgg     120
ttgtttcaga ggccaggcca gtctccaaag cgcctaatat atctggtgtc taaactggac     180
```

-continued

```
tctggagtcc ctgacaggtt cactggcagt ggatcaggga cagatttcac actgaaaatc    240
agcagagtgg aggctgagga tttgggaatt tattattgct ggcaaggtac acattttccg    300
tacacgttcg gaggggggac caatttggaa ataaaacg                            338
```

METHOD OF TREATING OR PREVENTING RHEUMATOID ARTHRITIS

CROSS-REFERENCE TO RELATED APPLICATIONS

This application is a continuation of U.S. patent application Ser. No. 13/514,923, filed Aug. 20, 2012, pending, which application is a national phase entry under 35 U.S.C. § 371 of international Patent Application PCT/EP2010/069431, filed Dec. 10, 2010, published in English as International Patent Publication WO 2011/070172 A1 on Jun. 16, 2011, which claims the benefit under Article 8 of the Patent Cooperation Treaty to European Patent Application Serial No. 09178658.2, filed Dec. 10, 2009, the disclosure of each of which is hereby incorporated herein in its entirety by this reference.

STATEMENT ACCORDING TO 37 C.F.R. § 1.821(c) or (e)—SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

This disclosure is in the field of treating or preventing inflammation in humans and animals and relates to pharmaceutical compositions and methods for treating or preventing various inflammatory conditions. In particular, the disclosure relates to compositions and methods for preventing or treating inflammatory conditions such as citrulline-related diseases, preferably inflammatory diseases, more preferably inflammatory arthritis, such as rheumatoid arthritis. The disclosure provides specific binding molecules, such as antibodies, directed against citrulline-containing epitopes for use in the therapy and prevention of inflammatory conditions such as inflammatory arthritis, preferably rheumatoid arthritis.

BACKGROUND

Inflammatory conditions, whether of a chronic or acute nature, represent a substantial problem in the healthcare industry. Briefly, chronic inflammation is considered to be inflammation of a prolonged duration (weeks or months) in which active inflammation, tissue destruction and attempts at healing are proceeding simultaneously (*Robbins Pathologic Basis of Disease* by R. S. Cotran, V. Kumar, and S. L. Robbins, W. B. Saunders Co., p. 75, 1989). Although chronic inflammation can follow an acute inflammatory episode, it can also begin as an insidious process that progresses with time, for example, as a result of a persistent infection (e.g., tuberculosis, syphilis, and fungal infection) that causes a delayed hypersensitivity reaction, prolonged exposure to endogenous (e.g., elevated plasma lipids) or exogenous (e.g., silica, asbestos, cigarette tar, and surgical sutures) toxins, or autoimmune reactions against the body's own tissues (e.g., rheumatoid arthritis, systemic lupus erythematosus, multiple sclerosis, and psoriasis).

Inflammatory arthritis is a serious health problem in developed countries, particularly given the increasing number of aged individuals. For example, one form of inflammatory arthritis, rheumatoid arthritis (RA), is a multisystem chronic, relapsing, inflammatory disease affecting 1% to 2% of the world's population.

Although many organs can be affected, RA is basically a severe form of chronic synovitis that sometimes leads to destruction and ankylosis of affected joints (*Robbins Pathologic Basis of Disease* by R. S. Cotran, V. Kumar, and S. L. Robbins, W.B. Saunders Co., 1989). Pathologically, the disease is characterized by a marked thickening of the synovial membrane that forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and eventually the pannus grows to fill the joint space. The pannus develops an extensive network of new blood vessels through the process of angiogenesis, which is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachidonic acid metabolism) from the cells of the pannus tissue leads to the progressive destruction of the cartilage tissue. The pannus invades the articular cartilage leading to erosions and fragmentation of the cartilage tissue. Eventually, there is erosion of the subchondral bone with fibrous ankylosis, and ultimately bony ankylosis, of the involved joint.

It is generally believed that RA is an autoimmune disease and that many different arthrogenic stimuli activate the immune response in an immunogenetically susceptible host. Both exogenous infectious agents (Epstein-Barr virus, rubella virus, cytomegalovirus, herpes virus, human T-cell lymphotropic virus, mycoplasma, and others) and endogenous proteins such as collagen, proteoglycans, altered immunoglobulins and post-translationally modified proteins like citrullinated proteins have been implicated as a causative agent that triggers an inappropriate host immune response. Regardless of the inciting agent, autoimmunity plays a role in the progression of the disease. In particular, the relevant antigen is ingested by antigen-presenting cells (macrophages or dendritic cells in the synovial membrane), processed, and presented to T lymphocytes. The T cells initiate a cellular immune response and stimulate the proliferation and differentiation of B lymphocytes into plasma cells. The end result is the production of an excessive inappropriate immune response directed against the host tissues (e.g., antibodies directed against type II collagen, antibodies directed against the Fc portion of autologous IgG (called "Rheumatoid Factor")) and antibodies directed against different citrullinated epitopes (anti-CCP). This further amplifies the immune response and hastens the destruction of the cartilage tissue. Once this cascade is initiated, numerous mediators of cartilage destruction are responsible for the progression of rheumatoid arthritis.

The above-mentioned anti-CCP antibodies have been demonstrated to be highly specific for RA. Recent evidence shows that each individual that is seropositive for these antibodies either already has RA or will develop this disease in the future. The presence of anti-CCP antibodies (especially when high titers are present) is predictive of erosive disease outcome (Nijenhuis et al., *Clin. Chim. Acta*, vol.

350, 17-34, 2004). Furthermore, it has been demonstrated that anti-CCP antibodies are produced locally at the site of inflammation. The proportion of anti-CCP antibodies with respect to total IgG found in synovial material from RA patients appeared to be significantly higher than that in serum of the same patients (Masson-Bessiere et al., *Clin. Exp. Immunol.*, vol. 119, 544-552, 2000) (Reparon-Schuijt et al., *Arthritis Rheum.*, vol. 44, 41-47, 2001).

The presence of anti-CCP producing plasma cells in the synovium is indicative of an antigen-driven maturation of CCP-specific B cells at the site of inflammation. Once anti-CCP antibodies are produced, the formation of immune complexes with citrullinated proteins in the synovia may trigger the progression of the inflammatory process. These and other data supported the hypothesis that anti-CCP antibodies actually caused at least part of the disease symptoms of RA. A role for the anti-CCP antibodies in the pathogenesis of RA is supported by the results of B lymphocyte depletion experiments in patients with RA (Cambridge et al., *Arthritis Rheum.*, vol. 48, 2146-2154, 2003).

People with advanced rheumatoid arthritis have a mortality rate greater than some forms of cancer and because of this, treatment regimens have shifted toward aggressive early drug therapy designed to reduce the probability of irreversible joint damage. Recent recommendations of the American College of Rheumatology (*Arthritis and Rheumatism* 39(5):713-722, 1996) include early initiation of disease-modifying anti-rheumatic drug (DMARD) therapy for any patient with an established diagnosis and ongoing symptoms. Anticancer drugs have become the first line therapy for the vast majority of patients, with the chemotherapeutic drug methotrexate being the drug of choice for 60% to 70% of rheumatologists. The severity of the disease often warrants indefinite weekly treatment with this drug, and in those patients whose disease progresses despite methotrexate therapy (over 50% of patients), second line chemotherapeutic drugs such as cyclosporin and azathioprine (alone or in combination) are frequently employed.

There remains a need for compounds for the treatment or prevention of inflammatory diseases that are capable of inhibiting the pathogenesis of inflammatory diseases, in particular, diseases wherein the synovium is involved, and citrulline-related inflammatory diseases.

BRIEF SUMMARY

The disclosure provides a binding molecule specifically reactive with a citrullinated epitope on p15 and/or p17 for use in the treatment or prevention of inflammatory diseases.

P15 and p17 are identified herein as human PAD4- and/or PAD2-deiminated human histone 2A and/or histone 4, and/or on human PAD2-deiminated human histone H3.

The disclosure also provides a method for treating or preventing an inflammatory disease, comprising the step of administering to a patient in need thereof a therapeutically effective amount of an anti-inflammatory composition comprising a binding molecule specifically reactive with a citrulline epitope on p15 and/or p17.

The compositions and methods of the present disclosure include pharmaceutically acceptable formulations of specific binding molecules reactive with citrulline residues. In particular, the binding molecules are specifically reactive with citrullinated epitopes on two polypeptides as identified herein, termed "p15" and "p17."

The disclosure also relates to polypeptides and nucleic acids as identified herein.

These and other aspects of this disclosure will become evident upon reference to the following detailed description, figures and examples. In addition, various references are set forth herein that describe in more detail certain procedures, devices, or compositions, and are, therefore, incorporated herein by reference in their entirety.

BRIEF DESCRIPTION OF THE DRAWINGS

FIG. 7A shows the macroscopical inflammation in the right hind paws between experimental groups on the last day of the experiment (day 35). Each dot depicts a single animal. The horizontal lines indicate the mean score within an experimental group. It may be concluded that RhmAb2.102 injection protects the mice from permanent joint damage.

DETAILED DESCRIPTION

Figure 1A:
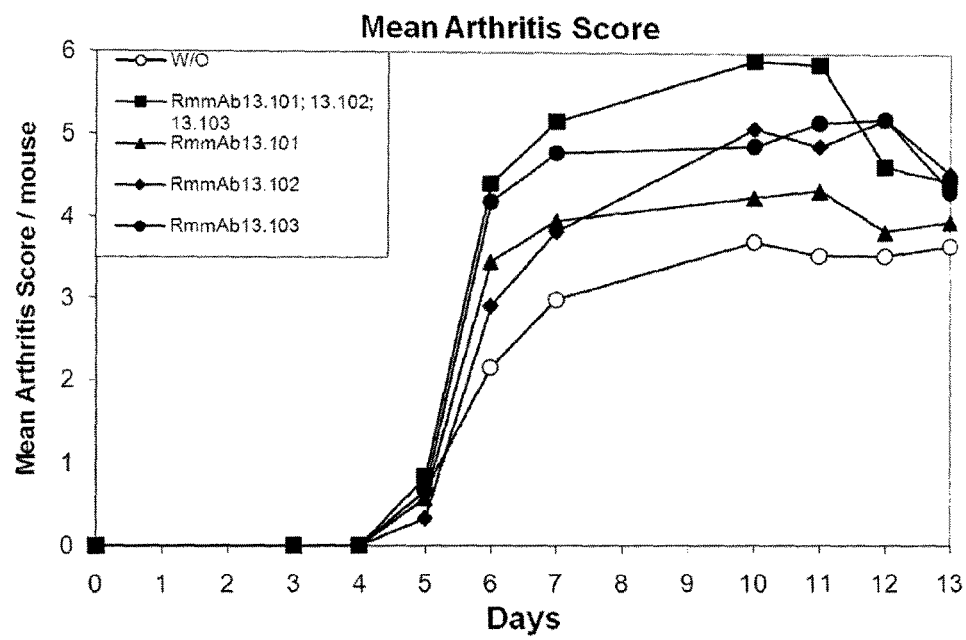
FIGS. 1A-1F: A collagen antibody-induced arthritis (CAIA) model was used to test the effect of monoclonal antibodies on the severity of symptoms of arthritis. Mean arthritis score (FIGS. 1A, 1C and 1E) and arthritis incidence (FIGS. 1B, 1D and 1F) are indicated. Groups of five to six mice were treated at day 0 through i.p. injection with anti-collagen antibodies. Mice used in the experiments shown in FIGS. 1A and 1B received 1.6 mg anti-collagen antibody mix, whereas mice used in FIGS. 1C-1F received 2.4 mg. LPS (25 µg/mouse) together with anti-citrulline or a control antibody (RhmAb2.201) were administered on day 3 through i.p. injection. All antibodies were administered at 1 mg/mouse unless otherwise stated in the graph. Animals have been scored daily until day 13.

The disclosure provides a binding molecule specifically reactive with a citrullinated epitope on p15 and/or p17 for use in the treatment or prevention of inflammatory diseases.

The term "specific binding molecule" is used herein to indicate a molecule, preferably a small molecule, capable of specific binding. Specific binding in this respect is intended to mean that the molecule is capable of binding to a selected target molecule whereas it will not bind to another, non-related target molecule under the same conditions. For instance, a binding molecule is said to specifically bind to serum albumin when it binds to serum albumin and binds less or not at all to another or preferably any other protein found in serum. Preferred specific binding molecules are antibodies.

The term "specifically reacts with citrulline" or "reactive with a citrullinated epitope" or "reactive with a citrulline epitope" in this context means that the specific binding molecule or antibody reacts with a structure such as a peptide containing a citrulline residue, whereas the antibody reacts less or preferably not at all with the same structure containing an arginine residue instead of the citrulline residue. The term "peptide" should be interpreted as a structure that is capable of presenting the citrulline residue in the correct context for immunoreactivity with the specific binding molecules as described herein, preferably in the same context as it appears in the human or animal body, preferably in the context of a native polypeptide. It is also preferred that the citrulline residue is presented in the context of a native polypeptide that does not activate or trigger other components of the immune system such as cell activation or complement binding.

The "specific binding molecule" may be a molecule, preferably a small molecule, composed of DNA, RNA, peptide, protein domain, whole proteins, or combinations thereof or parts thereof, that are capable of specifically binding to a target compound. Preferred examples of specific binding molecules are peptides or antibodies.

Native antibodies (also known as immunoglobulins) are gamma globulin proteins that may be found in blood or other bodily fluids of vertebrates, and are used by the immune system to identify and neutralize foreign objects, such as bacteria and viruses.

Native antibodies are typically made of basic structural units—each with two large heavy chains and two small light chains—to form, for example, monomers with one unit, dimers with two units or pentamers with five units. Antibodies are produced by a white blood cell called a B cell. There are several different types of heavy chains, resulting in different kinds of antibodies. Antibodies may be grouped into different isotypes based on which heavy chain they possess. Five different antibody isotypes are known in mammals that perform different roles, and help direct the appropriate immune response for each different type of foreign object they encounter. Some animal species such as Camelids (e.g., llamas) and sharks may have aberrant antibody structures.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens.

The unique part of the antigen recognized by an antibody is called an epitope. These epitopes bind with their antibody in a highly specific interaction that allows antibodies to identify and bind only their unique antigen in the midst of the millions of different molecules that make up an organism. Recognition of an antigen by an antibody tags it for attack by other parts of the immune system. Antibodies can also neutralize targets directly, for example, by binding to a part of a pathogen that it needs to cause an infection.

The large and diverse population of antibodies is generated by random combinations of a set of gene segments that encode different antigen-binding sites (or paratopes), followed by random mutations in this area of the antibody gene, which create further diversity. Antibody genes also re-organize in a process called class switching that changes the base of the heavy chain to another, creating a different isotype of the antibody that retains the antigen-specific variable region. This allows a single antibody to be used in several different isotypes by several different parts of the immune system.

The term "antibodies" or "antibody" as used herein refers to a structure, preferably a protein or polypeptide structure, capable of specific binding to a target molecule often referred to as "antigen."

An antibody may be selected from the group consisting of single-chain antibodies, single-chain variable fragments (scFvs), fragment antigen-binding regions (Fabs), recombinant antibodies, monoclonal antibodies, fusion proteins comprising the antigen-binding domain of a native antibody or an aptamer, single-domain antibodies (sdabs), also known as VHH antibodies, nanobodies (camelid-derived single-domain antibodies), shark IgNAR-derived single-domain antibody fragments called VNAR, anticalins, aptamers (DNA or RNA) and active components or fragments thereof.

In another preferred embodiment, an antibody is a fusion protein comprising the antigen-binding domain of a native antibody or an aptamer, such as an aptamer in the form of DNA or RNA.

The term "or part thereof" or "fragments thereof" in the context of an antibody or other specific binding molecule is meant to refer to the part of the antibody or specific binding molecule that makes up the specific binding site of the antibody or specific binding molecule and may be interpreted as the part of an antibody or specific binding molecule that is still capable of reacting with the same epitope as the entire antibody or specific binding molecule.

Human antibodies or fragments thereof are a preferred embodiment of the disclosure. Preferably, IgG1 (e.g., IgG1λ) antibodies having an IgG1 heavy chain and a lambda light chain may be used advantageously. However, other human antibody isotypes are also encompassed by the disclosure, including IgG2, IgG3, IgG4, IgM, IgA1, IgA2, IgAsec, IgD and IgE in combination with a kappa or lambda light chain. Also, all animal-derived antibodies of various isotypes can be used in the disclosure. The antibodies can be full-size antibodies or antigen-binding fragments of antibodies, including Fab, F(ab')2, single-chain Fv fragments, or single-domain VHH, VH or VL single domains.

The term "specific binding molecules reactive with a citrullinated epitope" is to be interpreted as specific binding molecules that specifically react with a citrulline residue in the context of a larger structure such as a peptide or a peptide nucleic acid or an aptamer or a peptide mimicking structure.

Citrulline is an amino acid that is not incorporated into proteins during normal translation; however, it may be generated by post-translational modification of an arginine residue by peptidylarginine deiminase (PAD).

Citrullination is the post-translational conversion of arginine residues to citrulline residues, which is catalyzed by peptidylarginine deiminase (PAD). Peptidylarginine deiminase (PAD; EC 3.5.3.15) enzymes catalyze the conversion of arginine residues to citrulline residues in proteins. No tRNA exists for citrulline; the presence of citrulline residues in proteins is exclusively the result of post-translational modification. In mammals (humans, mice and rats), five PAD isotypes (PAD1-PAD6; "PAD4" and "PAD5" are used for the same isotype), each encoded by a distinct gene, have been identified (Vossenaar et al., *Bioessays* 25, 1106-1118, 2003). All these enzymes rely strongly on the presence of Ca2+ for activity and are unable to convert free L-arginine into free L-citrulline. Free L-arginine can be converted to free L-citrulline by nitric oxide synthase (EC 1.14.13.39) in eukaryotes or by arginine deiminase (EC 3.5.3.6) in bacteria. These enzymes are not Ca2+ dependent.

The most pronounced difference between the highly homologous PAD enzymes is their tissue-specific expression. In epidermis, PAD1 (synonyms: PAD I, PAD type I) is involved in the citrullination of keratin filaments during the final stages of keratinocyte differentiation, which is important for the reorganization of the cornified envelope. Another site of citrullination in the epidermis is the hair follicle, which contains PAD3 (synonyms PAD III, PAD type III) and its natural substrate trichohyalin (THH). THH is a major structural protein of the inner root sheath cells and the medulla layer of the hair follicle and, to a lesser extent, of other specialized epithelia. The most recently identified PAD isotype, PAD6 (synonym: ePAD), was found in cytoplasmic sheets of mouse oocytes, which play an important role in early embryogenesis. The expression of its human orthologue was found to be restricted to ovary, testis and peripheral blood leukocytes (Chavanas et al., *Gene*, vol. 330; 19-27, 2004). Originally, this PAD isotype was designated ePAD, but based upon the systematic numbering of other PADs, this isotype was renamed PAD6 (Vossenaar et al., *Bioessays*, vol. 25 1106-1118, 2003). The most widely expressed isotype, PAD2 (synonyms PAD II, PAD type II, PAD-H19), is present in many different tissues, like skeletal muscle, brain, spleen, secretory glands and macrophages. Despite this broad expression pattern, only myelin basic protein (MBP) and vimentin have been identified as natural substrates. In multiple sclerosis (MS), patients develop an autoimmune response against MBP. MBP is an abundant protein of the myelin sheath, and its citrullination occurs during development of the central nervous system. Citrullination of vimentin was observed during calcium-ionophore-induced apoptosis of human and mouse macrophages and, as described above, citrullinated vimentin was shown to be the target of the RA-specific anti-Sa autoantibodies. In contrast to the PADs discussed above, which are all mainly localized in the cytoplasm of cells, the PAD4 isotype (synonyms: PAD IV, PAD type IV, HL-60 PAD, PAD V, PAD type V, PADI4) is localized in the nucleus. The nuclear localization signal of PAD4 was found in the N-terminal region of the protein. PAD4 is mainly expressed in peripheral blood granulocytes and monocytes. Substrates of PAD4 in the nucleus are histone core proteins (H2A, H3 and H4) and nucleophosmin/B23, a nucleolar protein that functions in ribosome assembly, nucleocytoplasmic transport and centrosome duplication.

Specific binding molecules according to the disclosure are directed against a citrullinated epitope on p15 and/or p17, two polypeptides characterized by their molecular weights of 15 kDa and 17 kDa, respectively.

Such specific binding molecules were found to be particularly suited for the treatment or prevention of inflammatory diseases.

"Inflammatory Conditions" or "Inflammatory diseases" as used herein refers to any of a number of conditions or diseases that are characterized by vascular changes: edema and infiltration of neutrophils (e.g., acute inflammatory reactions); infiltration of tissues by mononuclear cells; tissue destruction by inflammatory cells, connective tissue cells and their cellular products; and attempts at repair by connective tissue replacement (e.g., chronic inflammatory reactions).

Representative examples of such conditions include citrulline-related inflammatory diseases and autoimmune diseases. "Citrulline-related inflammatory diseases" are herein defined as those diseases wherein citrullination plays a role in the pathogenesis of the disease. Whether or not citrullination plays a role in the pathogenesis of the disease, may be easily determined by a skilled person using routine tests available in the art. For example, these diseases may be characterized by the presence of an abnormal level of citrullinated proteins in affected or disease-related tissue. Such may be accomplished by an immunological test such as a Western blot or an ELISA, wherein the affected tissue is used as an antigen and citrullination of that antigen may be detected with the aid of an anti-citrulline antibody as described herein.

Alternatively, a person skilled in the art can use Proteomics applications such as mass spec. analysis to compare the level and type of citrullination in a diseased versus healthy tissue from affected patients.

The disease may also be characterized by the presence of an immune response against citrulline-containing peptides or proteins. This may be a humoral or a cellular immune response, such as a response mediated by T-cells or B-cells. Tests for detecting anti-citrulline antibodies have been described in the art and are commercially available.

The disclosure, therefore, relates to a specific binding molecule for use in treating or preventing citrulline-related inflammatory diseases.

Such diseases are, for instance, inflammatory arthritis, including rheumatoid arthritis and osteoarthritis, multiple sclerosis, psoriatic arthritis, psoriasis, Alzheimer's disease, autoimmune hepatitis, juvenile idiopathic arthritis, spondylo-arthropathy, Down's syndrome, multiple system atrophy, Parkinson's disease and Lewy body dementia. The disclosure, therefore, relates to a specific binding molecule for use in treating or preventing diseases selected from the group consisting of arthritis, rheumatoid arthritis, osteoarthritis, multiple sclerosis, psoriatic arthritis, psoriasis, Alzheimer's disease, autoimmune hepatitis, juvenile idiopathic arthritis, spondyloarthropathy, Down's syndrome, multiple system atrophy, Parkinson's disease and Lewy body dementia.

The disclosure, in particular, relates to specific binding molecules for the treatment or prevention of autoimmune diseases, more in particular, rheumatoid arthritis or osteoarthritis.

Multiple sclerosis or MS is a chronic inflammatory disorder of the CNS, characterized by autoimmunity-mediated destruction of the myelin sheath. The cells of the myelin sheath form a multi-bilayer structure around the axons consisting of lipid-protein complexes in a ratio of about 3:1. Two major proteins, MBP and proteolipid protein, account for 85% of the protein fraction. MBP is a highly cationic protein, capable of forming strong interactions with negatively charged phospholipids such as phosphatidylserine. In approximately 18% of the MBP molecules of healthy adult humans, six (out of 19) arginines are citrullinated (Wood et al., *J. Biol. Chem.*, vol. 264, 5121-5127, 1989; Wood et al., *Ann. Neurol.*, vol. 40, 18-24, 1996). The remaining MBP molecules do not contain citrulline. In MS patients, the proportion of MBP-cit6 is increased to 45% of total MBP. The decreased net positive charge of MBP-cit6 causes partial unfolding of MBP molecules and weakens their interaction with the phospholipids (Boggs et al., *J. Neurosci. Res.*, vol. 57, 529-535, 1999, Pritzker et al., *Biochemistry*, vol. 39, 5374-5381, 2000). Although MBP-cit6 is capable of forming lipid complexes more rapidly than non-citrullinated MBP, the complexes that are formed are not as densely packed as those formed with non-citrullinated MBP (Boggs et al., *J. Neurosci. Res.*, vol. 57, 529-535, 1999; Beniac et al., *J. Struct. Biol.*, vol. 129, 80-95, 2000). MBP-cit6 is degraded four times more rapidly by cathepsin D than non-citrullinated MBP (Cao et al., *Biochemistry*, vol. 38, 6157-6163, 1999). In a rare case of acute fulminating MS (Marburg type), 80% of the MBP molecules are heavily citrullinated (MBPcit18) (Wood et al., *Ann. Neurol.*, vol. 40, 18-24, 1996). The severely unfolded MBP-cit18 is degraded 45 times more rapidly by cathepsin D than normal MBP (Cao et al., *Biochemistry*, vol. 38, 6157-6163, 1999). Clinical trials with paclitaxel, the active component of the anticancer drug TAXOL®, are in progress (O'Connor et al., *Ann. Neurol.*, vol. 46, 470, 1999). Low doses of paclitaxel can inhibit citrullination of MBP by PAD2 in vitro (Pritzker et al., *Biochem. Biophys. Acta*, vol. 1388, 154-160, 1998). Treatment with paclitaxel attenuates clinical symptoms and induces remyelination of damaged sheaths (Moscarello et al., *Mult. Scler.* vol. 8, 130-138, 2002), underlining the possible importance of PAD as a candidate factor in demyelinating disease (Moscarello et al., *J. Neurochem.*, vol. 81, 335-343, 2002).

In psoriasis, keratinocytes proliferate very rapidly and travel from the basal layer to the surface in only about four days. The skin cannot shed these cells quickly enough so they accumulate in thick, dry patches, or plaques. In normal keratinocytes, keratin K1 is citrullinated by PAD1 during terminal differentiation. This process causes the keratin filaments to become more compact, which is essential for the normal cornification process of the epidermis. The keratinocytes in the psoriatic hyperproliferative plaques do not contain citrullinated keratin K1 (Ishida-Yamamoto et al., *J. Invest. Dermatol.*, vol. 114, 701-705, 2000). It is not clear whether the increased cell proliferation prevents adequate citrullination by PAD or that inactivity of PAD allows hyperproliferation and accumulation of keratinocytes. Although the mechanism is unknown, aberrant citrullination in psoriatic epidermis obviously is related to PAD1.

In a preferred embodiment, the composition according to the invention is in a form selected from the group consisting of an aqueous solution, a gel, a hydrogel, a film, a paste, a cream, a spray, an ointment, or a wrap. In further embodiments, the above methods are used to administer the compositions described herein by a route selected from intraarticular, intraperitoneal, topical, rectal, intravenous, oral, ocular, or to the resection margin of tumors.

In certain embodiments, a pharmaceutically acceptable carrier comprises at least one carrier selected from the group consisting of a co-solvent solution, liposomes, micelles, liquid crystals, nanocrystals, nanoparticles, emulsions, microparticles, microspheres, nanospheres, nanocapsules, polymers or polymeric carriers, surfactants, suspending agents, complexing agents such as cyclodextrins or adsorbing molecules such as albumin, surface active particles, and chelating agents. In further embodiments, a polysaccharide comprises hyaluronic acid and derivatives thereof, dextran and derivatives thereof, cellulose and derivatives thereof (e.g., methylcellulose, hydroxypropylcellulose, hydroxypropylmethylcellulose, carboxymethylcellulose, cellulose acetate phthalate, cellulose acetate succinate, cellulose acetate butyrate, hydroxypropylmethylcellulose phthalate), chitosan and derivatives thereof, [beta]-glucan, arabinoxylans, carrageenans, pectin, glycogen, fucoidan, chondroitins, dermatan, heparan, heparin, pentosan, keratin, alginate, cyclodextrins, and salts and derivatives, including esters and sulfates, thereof.

In a further aspect, the method according to the disclosure comprises delivering a composition according to the disclosure to a target site, most notably a synovial joint.

In one specific embodiment of the disclosure, the specific binding molecule competes with monoclonal antibodies RhmAb2.102, RhmAb2.108, RhmAb2.109, RhmAb2.110, RhmAb2.111 and RhmAb2.112 and RmmAb22.101 for binding to p15 and/or p17.

These antibodies are disclosed herein by the primary amino acid sequence of their heavy and light chains (see Table 10).

TABLE 10

Antibody primary amino acid sequences

| Seq. ID. | Prot/DNA | Name |
|---|---|---|
| 1 | prot. | histone 3, h2bb [*Mus musculus*] |
| 2 | prot. | histone 3, h2bb [*Mus musculus*] |
| 3 | prot. | similar to histone H2B [*Bos taurus*] |
| 4 | prot. | histone cluster 1, H2bn [*Bos taurus*] |
| 5 | prot. | histone cluster 2, H4 [*Rattus norvegicus*] |
| 6 | prot. | histone cluster 2, H4 [*Rattus norvegicus*] |
| 7 | prot. | histone cluster 2, H4 [*Rattus norvegicus*] |
| 8 | DNA | human IgG1 heavy chain RhmAb2.102 |
| 9 | DNA | human Lambda light chain RhmAb2.102 |
| 10 | DNA | human kappa light chain Rhmab2.110 |
| 11 | DNA | human kappa constant domain |
| 12 | prot. | Mouse Leader sequence |
| 13 | prot. | VH Rhmab2.102 |
| 14 | prot. | human constant Fc IgG1 |
| 15 | prot. | VL Rhmab2.102 |
| 16 | prot. | human Lambda constant domain |
| 17 | DNA | VL Rhmab2.108 |
| 18 | DNA | VH Rhmab2.108 and Rhmab2.111 |
| 19 | DNA | VL Rhmab2.111 |
| 20 | DNA | VH Rhmab2.109 |
| 21 | prot. | peptide no. 1 (human histone 2A) |
| 22 | prot. | peptide no. 2 (human histone 2A) |
| 23 | prot. | peptide no. 3 (human histone 2A) |
| 24 | prot. | peptide no. 4 (human histone 2A) |
| 25 | prot. | peptide no. 5 (human histone 2A) |
| 26 | prot. | peptide no. 6 (human histone 2A) |
| 27 | prot. | peptide no. 7 (human histone 2A) |
| 28 | prot. | peptide no. 8 (human histone 2A) |
| 29 | prot. | peptide no. 9 (human histone 2A) |
| 30 | prot. | peptide no. 10 (human histone 2A) |
| 31 | prot. | peptide no. 11 (human histone 2A) |
| 32 | prot. | peptide no. 12 (human histone 2A) |
| 33 | prot. | msFibα XH |
| 34 | prot. | msFibα XG |
| 35 | prot. | huFibα XH |
| 36 | prot. | huFibα XG |
| 37 | prot. | msFibβ XG |
| 38 | prot. | msVim XS/XL |
| 39 | DNA | VL Rhmab2.109 |
| 40 | DNA | VH Rhmab2.110 |
| 41 | DNA | VL Rhmab2.110 |
| 42 | DNA | VH Rhmab2.112 |
| 43 | DNA | VL Rhmab2.112 |
| 44 | DNA | VH Rmmab22.101 |
| 45 | DNA | VL Rmmab22.101 |

Binding molecules or antibodies competing with the monoclonal antibodies as disclosed herein may be selected by standard procedures. In short, a binding assay such as an ELISA may be developed wherein the antigens as disclosed herein are immobilized on a solid support. The monoclonal antibodies as disclosed herein may be labeled and interference with their binding to the immobilized antigens may be easily determined by routine analysis. These and other, more sophisticated methods are known to the skilled person and can be routinely performed in an ordinary laboratory setting.

In particular, assays may easily be developed using any of the antigenic proteins according to SEQ ID NO: 21, SEQ ID NO: 24, SEQ ID NO: 26, SEQ ID NO: 37 and SEQ ID NO: 38 immobilized on a solid support. Monoclonal antibodies selected from the group consisting of RhmAb2.102, RhmAb2.108, RhmAb2.109, RhmAb2.110, RhmAb2.111, RhmAb2.112 and RmmAb22.101 may be labeled and contacted with the immobilized antigen in the presence and the absence of a test antibody. If the test antibody interferes with the binding, i.e., lowers the signal obtained with any of the labeled antibodies, it may be concluded that the test antibody competes with binding of the labeled antibody. Such a competing antibody would then be suitable for use in the methods of the disclosure.

The disclosure, therefore, relates to an antibody for use in the treatment or prevention of rheumatoid arthritis wherein the antibody is specifically reactive with a peptide selected from the group consisting of SEQ ID NO: 21, SEQ ID NO: 24, SEQ ID NO: 26, SEQ ID NO: 37 and SEQ ID NO: 38.

The primary mRNA sequences of the variable regions of monoclonal antibody RhmAb2.101 have been published and were deposited in the EMBL database under accession numbers as shown in Table 1. The primary sequence of the variable regions of monoclonal antibodies RhmAb2.102, RhmAb2.108, RhmAb2.109, RhmAb2.110, RhmAb2.111 and RhmAb2.112, are disclosed herein in SEQ ID NO: 13, SEQ ID NO: 15, SEQ ID NO: 17, SEQ ID NO: 18, SEQ ID NO: 39, SEQ ID NO: 20, SEQ ID NO: 41, SEQ ID NO: 40, SEQ ID NO: 19, SEQ ID NO: 43, and SEQ ID NO: 42

Mouse monoclonals RmmAb22.101 and RmmAb22.102 were derived from hybridomas deposited with the DSMZ—Deutsche Sammlung von Mikroorganismen and Zellkulturen GmbH, Inhoffenstraße 7 B, 38124 Braunschweig, GERMANY and received DSMZ deposit number ACC 3031 and ACC 3032, respectively. After sequencing, they appeared to have an identical DNA sequence, which is shown in SEQ ID NO: 44 and SEQ ID NO: 45.

The disclosure, therefore, also relates to a polypeptide comprising a variable heavy or light chain selected from the group consisting of SEQ ID NO: 18, SEQ ID NO: 17, SEQ ID NO: 20, SEQ ID NO: 39, SEQ ID NO: 40, SEQ ID NO: 41, SEQ ID NO: 19, SEQ ID NO: 43, SEQ ID NO: 42, SEQ ID NO: 44 and SEQ ID NO: 45. The disclosure also relates to a nucleic acid encoding a polypeptide selected from the group consisting of SEQ ID NO: 18, SEQ ID NO: 17, SEQ ID NO: 20, SEQ ID NO: 39, SEQ ID NO: 40, SEQ ID NO: 41, SEQ ID NO: 19, SEQ ID NO: 43, SEQ ID NO: 42, SEQ ID NO: 44 and SEQ ID NO: 45. The disclosure also relates to a polypeptide comprising a variable heavy and light chain as is present in RmmAb22.101 and RmmAb22.102.

The disclosure also relates to a nucleic acid encoding a polypeptide according to a variable heavy and light chain as is present in RmmAb22.101 and RmmAb22.102, which is shown in SEQ ID NO: 44 and SEQ ID NO: 45.

In another preferred embodiment, the specific binding molecule is an antibody selected from the group consisting of monoclonal antibodies RhmAb2.102, RhmAb2.108, RhmAb2.109, RhmAb2.110, RhmAb2.111 and RhmAb2.112, RmmAb22.101, and RmmAb22.102.

In another preferred embodiment, the specific binding molecule comprises VH and/or VL domains derived or obtained from an antibody selected from the group consisting of monoclonal antibodies and RhmAb2.102, RhmAb2.108, RhmAb2.109, RhmAb2.110, RhmAb2.111 and RhmAb2.112, RmmAb22.101, and RmmAb22.102.

The term "derived" or "obtained" in this context means that the primary structure of the VH and/or VL domains may be determined from the protein and nucleic acid sequences disclosed herein and cloned and rearranged in a different context, for instance, a human antibody context displaying a mouse VH or VL domain. More in particular, the term "derived" or "obtained" in this respect means that the essential residues responsible for the specific binding properties of the VH and/or VL domains in a particular antibody are identified and that these essential residues or structural homologues thereof are then transferred into the context of another peptide.

Specific binding molecules according to the disclosure may be generated essentially in two ways. First, they may be derived from the antibodies and their sequences as presented herein. Reactivity of the antibodies may even be improved by site-directed mutagenesis, chain shuffling, sexual PCR, or by other means for antibody derivation and optimization known to the person skilled in the art. Alternatively, specific binding molecules, in particular, antibodies may be obtained by panning with any of the specifically reactive epitopes as described herein, in particular, deiminated histone 2A, peptide 1 (SEQ ID NO: 21) and other particularly reactive peptides.

A person skilled in the art may use the sequences described herein to clone or generate cDNA or genomic sequences, for instance, such as described in the examples below. Cloning of these sequences in an appropriate eukaryotic expression vector, like pcDNA3 (in VITROGEN®), or derivatives thereof, and subsequent transfection of mammalian cells (like CHO cells) with combinations of the appropriate light chain and heavy chain-containing vectors will result in the expression and secretion of the listed antibodies RhmAb2.102, RhmAb2.108, RhmAb2.109, RhmAb2.110. RhmAb2.111 and RhmAb2.112. RmmAb22.101, and RmmAb22.102. Also, mouse monoclonals RmmAb22.101 and RmmAb22.102 may be directly expressed and secreted by their respective hybridoma cell lines as deposited (DSMZ numbers ACC 3031 and ACC 3032).

The skilled person may also make analogues of the specific binding molecules as described herein by using the specific binding domains of the antibody sequences and express them in a different context such as a polypeptide such as a fusion protein. This is well known in the art.

Recombinant human and mouse monoclonal anti-citrulline antibodies were obtained as described in Examples 1, 13, and 14. Monoclonal antibody heavy chains RhmAb2.102, RhmAb2.108, RhmAb2.109, RhmAb2.110, RhmAb2.111 and RhmAb2.112 were obtained with a mouse leader sequence (SEQ ID NO: 12), and a human IgG1 Fc region (SEQ ID NO: 14). Monoclonal antibody light chains RhmAb2.102, RhmAb2.108, RhmAb2.109, RhmAb2.111 and RhmAb2.112 were obtained with a mouse leader sequence (SEQ ID NO: 12) and a human Lambda constant region (SEQ ID NO: 16). Monoclonal antibody RhmAb2.110 was obtained with a mouse leader sequence (SEQ ID NO: 12) and a human Kappa constant region (SEQ ID NO: 11).

Mouse monoclonal anti-citrulline-peptide antibodies RmmAb13.101, RmmAb13.102 and RmmAb13.103 were obtained from a commercial source (ModiQuest Research BV Nijmegen, The Netherlands; Cat no, MQ13.101, MQ13.102 and MQ13.103).

Anti-citrulline antibodies were tested in an experimental model wherein inflammation is induced by injecting anti-collagen antibodies into a mouse. This model is known as collagen antibody-induced arthritis (CAIA) (Nandakumar and Holmdahl, *J. Immunol. Methods*, vol. 304, 126-136, 2005). Anti-collagen antibodies were obtained from a commercial source (ModiQuest Research BV Nijmegen, The Netherlands; Cat no, MQ18.101).

Figure 1B:
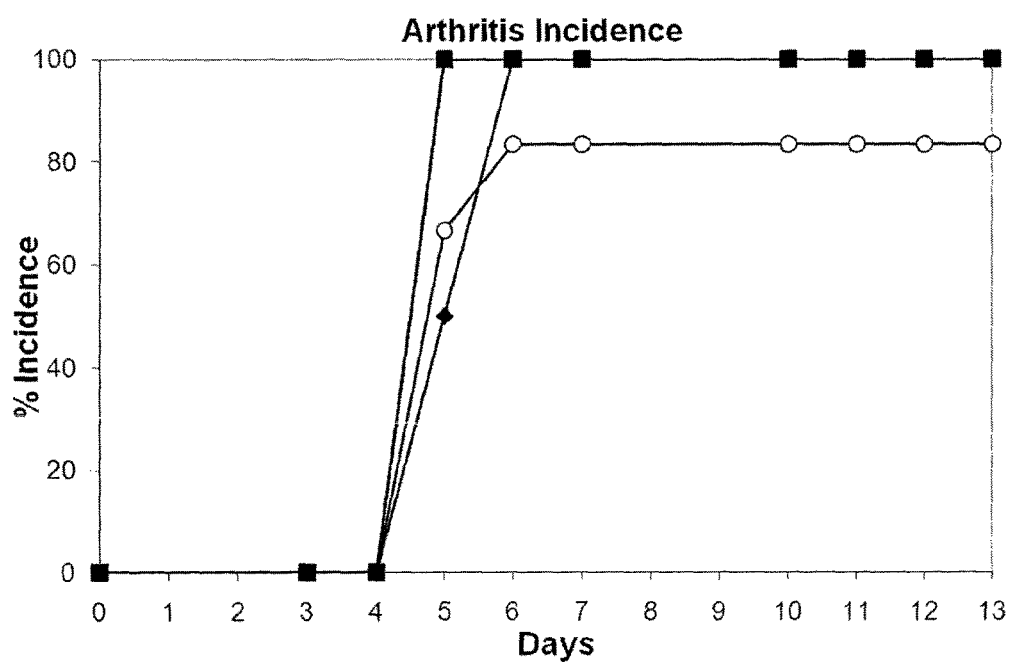

Mouse monoclonal anti-citrulline antibodies RmmAb13.101, RmmAb13.102 and RmmAb13.103 were confirmed to enhance the severity of the collagen antibody-induced arthritis, as has also been described by Kuhn et al. (*J. Clin. Invest.*, vol. 116, 961-871, 2006); and Hill et al. (*J. Exp. Med.*, vol. 205, 967-979, 2008). This is shown in FIGS. 1A and 1B.

Furthermore, several studies in human patients indicate that antibodies against citrullinated epitopes add to the pathogenesis of RA (Masson-Bessiere et al., *J. Immunol.*, vol. 166, 4177-4184, 2001; Vossenaar and van Venrooij, *Arthritis Res. Ther.*, vol. 6, 107-111, 2004). This is shown in FIGS. 1A and 1B, which show the "mean arthritis score" and "arthritis incidence," respectively, of the same experiment.

Surprisingly, however, human monoclonal antibody RhmAb2.102 dramatically reduced the clinical signs of arthritis in the experimental CAIA model.

Figure 1C:
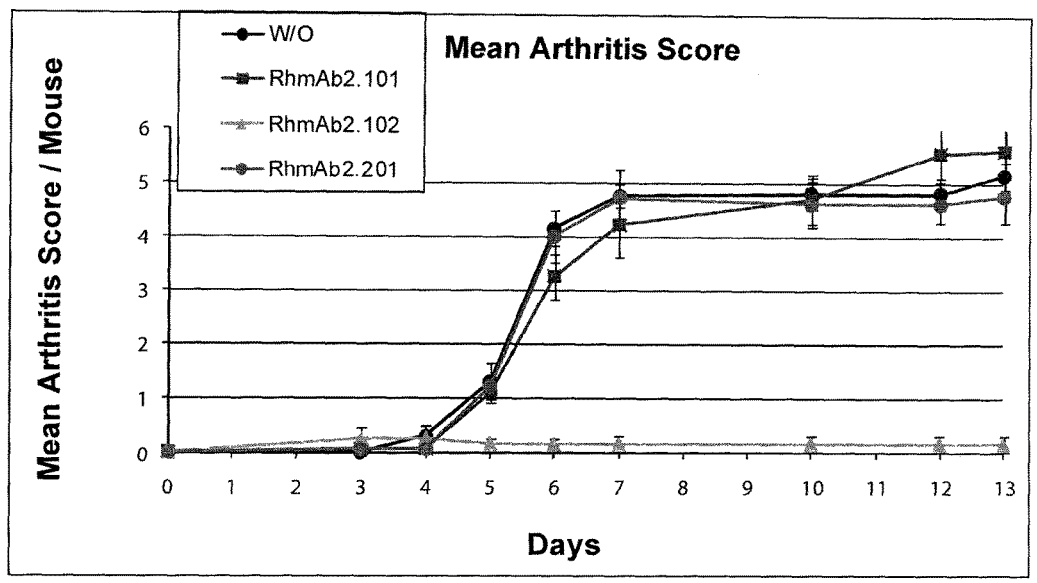
Figure 1D:
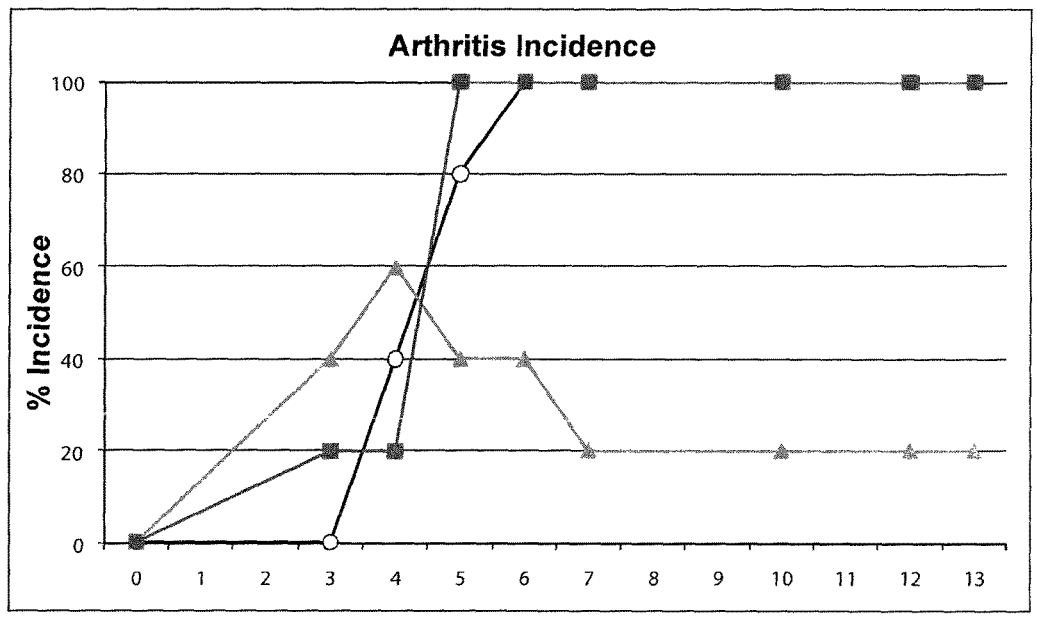
Figure 9:
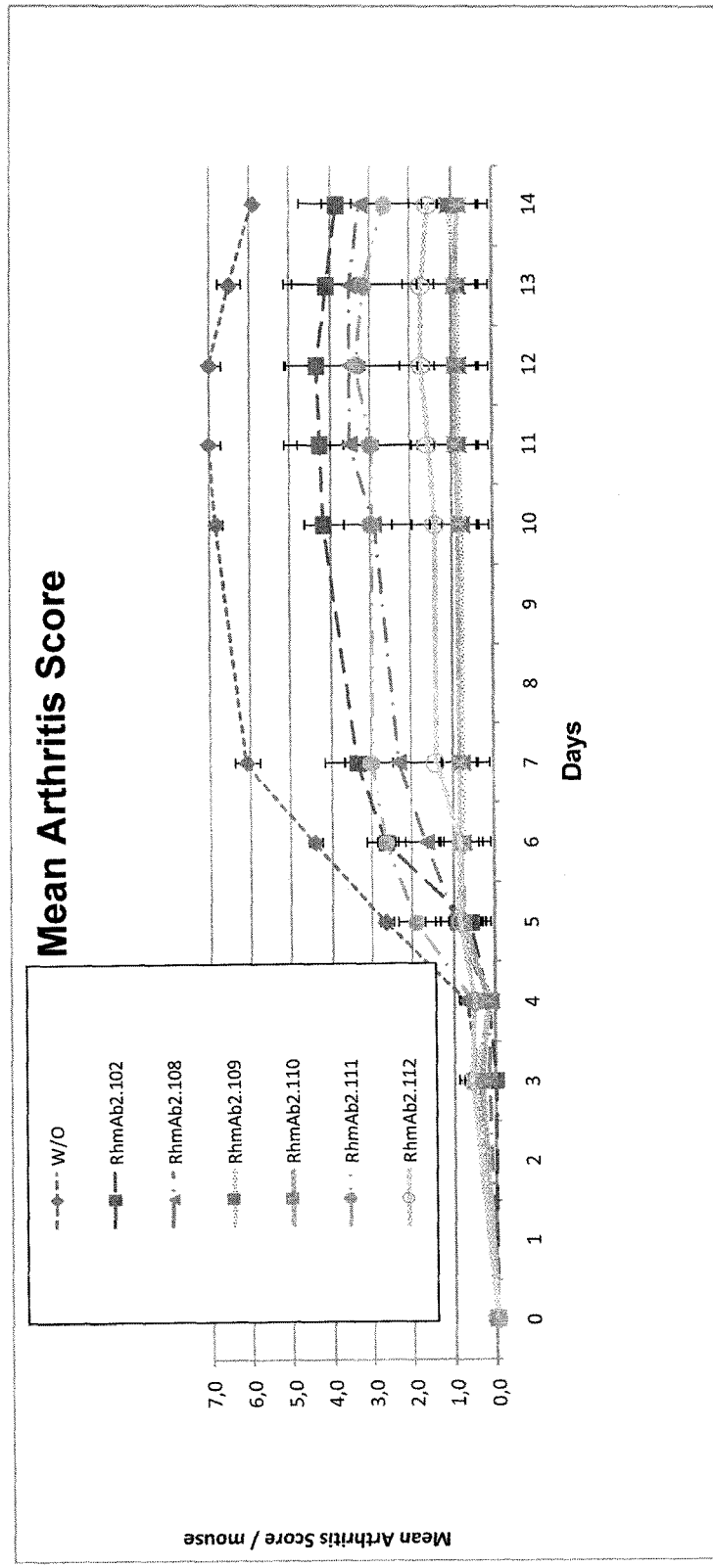
FIG. 9: The collagen antibody-induced arthritis (CAIA) model was used to test the anti-inflammatory effect of RhmAb2.102, RhmAb2.108, RhmAb2.109, RhmAb2.110, RhmAb2.111 and RhmAb2.112 when given on day 3 after injection of anti-collagen antibodies. Mean arthritis score of all paws are indicated. Groups of three mice were treated at day 0 with i.p. injection of 2.8 mg anti-collagen antibodies. LPS (25 µg/mouse) was administered at day 3 via i.p. injection, and RhmAb2.102, RhmAb2.108, RhmAb2.109, RhmAb2.110, RhmAb2.111 and RhmAb2.112 (1 mg/mouse) or placebo were injected via i.v. injection on the same day. Animals have been scored daily until day 14. All new antibodies RhmAb2.108, RhmAb2.109, RhmAb2.110, RhmAb2.111 and RhmAb2.112, showed a higher anti-inflammatory effect than RhmAb2.102.

Results obtained with RhmAb2.102 are shown in FIGS. 1C and 1D. Results obtained with RhmAb2.108, RhmAb2.109, RhmAb2.110, RhmAb2.111 and RhmAb2.112 were even better as compared to RhmAb2.102, as shown in FIG. 9.

The human monoclonal antibody RhmAb2.101 had no effect at all on the clinical signs of arthritis at the dose applied. The commercially available antibody RhmAb2.201 is used as an irrelevant antibody control in this experiment (ModiQuest Research B.V., cat no: MQR2.201). This antibody does not recognize citrullinated epitopes.

The same animal experiments were also performed with the mouse monoclonal antibodies RmmAb22.101 and RmmAb22.102, which recognize a similar subset of epitopes as the human antibodies RhmAb2.108, RhmAb2.109, RhmAb2.110, RhmAb2.111 and RhmAb2.112.

Figure 10:
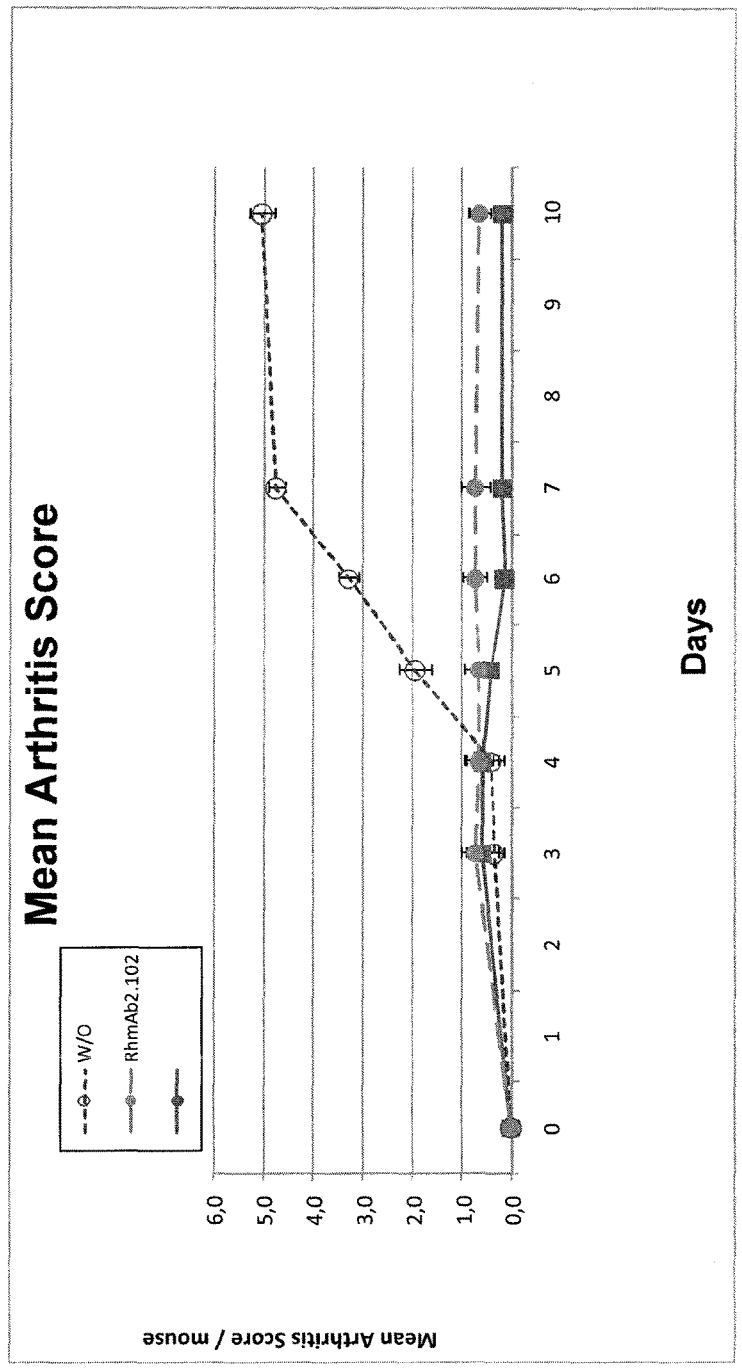
FIG. 10: The collagen antibody-induced arthritis (CAIA) model was used to test the anti-inflammatory effect of RhmAb2.102, RmmAb22.101, and RmmAb22.102 antibodies. Groups of three mice were treated at day 0 with i.p. injection of 2.8 mg anti-collagen antibodies. LPS (25 µg/mouse) as well as RhmAb2.102, RmmAb22.101 and RmmAb22.102 (6 mg/mouse) and placebo were administered via i.p. injection on day 3. All animals have been scored for inflammation daily until day 10. All tested antibodies, RhmAb2.102, RmmAb22.101 and RmmAb22.102, protected the mice against inflammation in their paws. Only data of RhmAb2.102 and RmmAb22.101 are shown.
Figure 11A:
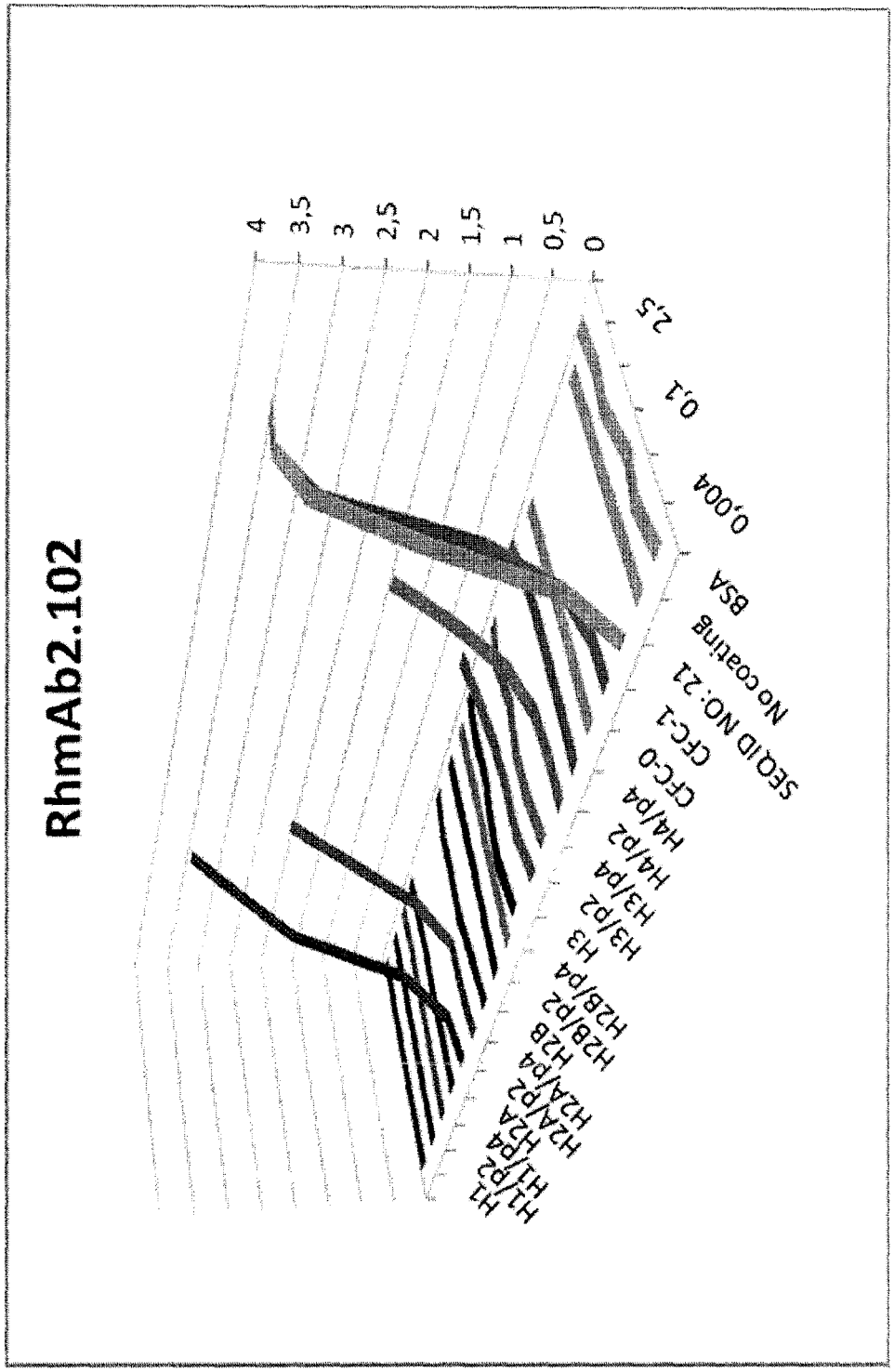
FIGS. 11A-11H: An enzyme-linked immunosorbent assay (ELISA) was used to test the affinity of RhmAb2.102 (FIG. 11A), RhmAb2.108 (FIG. 11B), RhmAb2.109 (FIG. 11C), RhmAb2.110 (FIG. 11D), RhmAb2.111 (FIG. 11E), RhmAb2.112 (FIG. 11F), RmmAb22.101 (FIG. 11G), and RmmAb22.102 (FIG. 11H) for human recombinant histones (H1, H2A, H2B, H3 and H4) deiminated with huPAD2 or huPAD4. Deiminated as well as non-deiminated histones, and BSA were immobilized on 96-well ELISA plates (0.3 µg/well). CFC-1, CFC-0, SEQ ID NO: 21 were coated at the same concentration and served as positive and negative controls, respectively, for specific anti-citrulline reactivity and as coating controls. Non-coated wells were used to test for aspecific binding of the antibodies. Coated wells were incubated with antibody dilution series ranging from 2.5 µg/well down to 0.004 µg/well for 1 hour at RT (z-axis). Detection of bound anti-citrulline antibodies was performed by incubating the wells with rabbit anti-human HRP (1:2000) for 1 hour at RT followed by incubation with TMB substrate. The resulting OD (y-axis) is a measure for antibody binding. H1-recombinant histone 1; H1/p2=huPAD2 recombinant histone 1; H1/p4-huPAD4 recombinant histone 1 and so forth (x-axis).
Figure 11B:
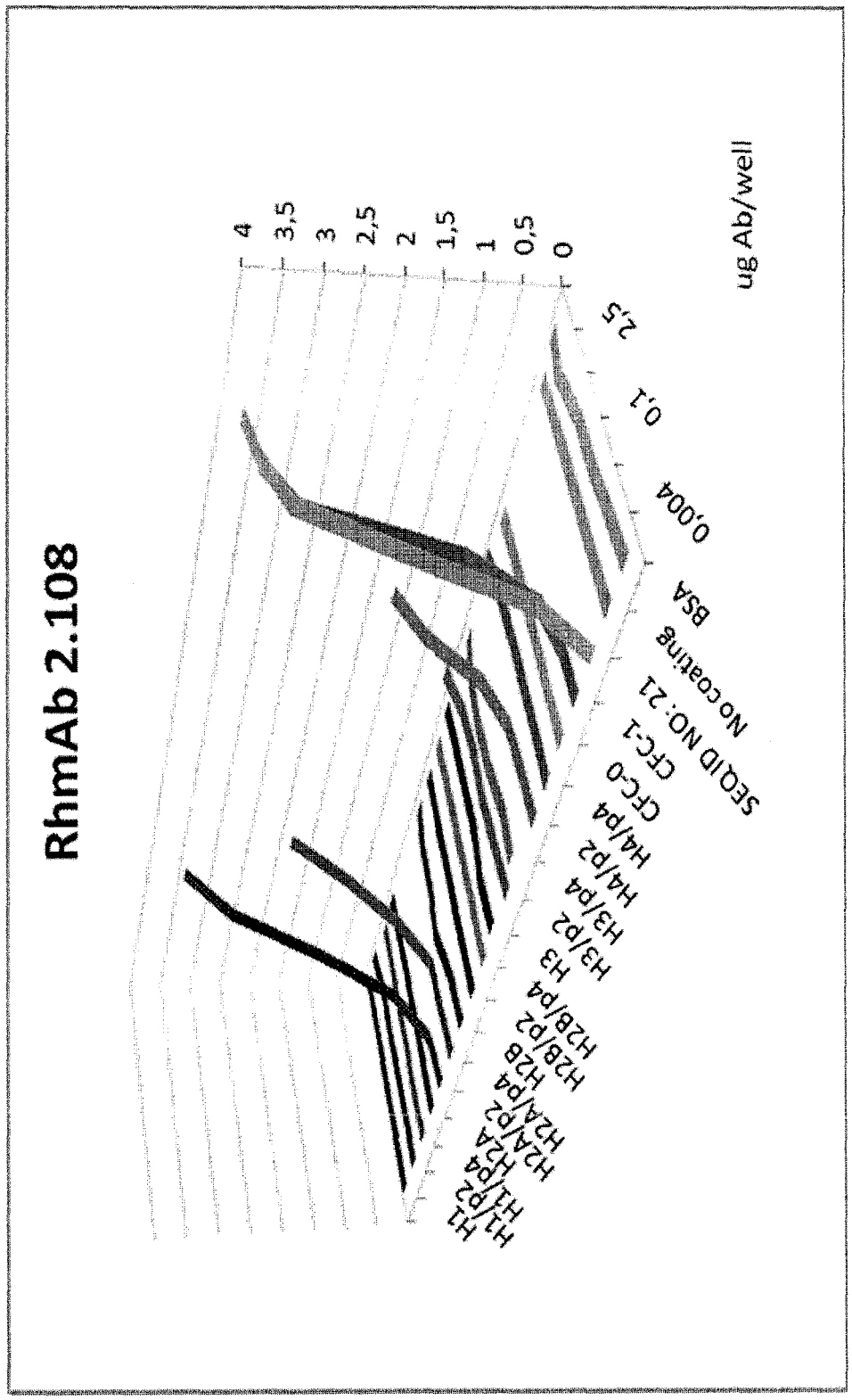
Figure 11C:
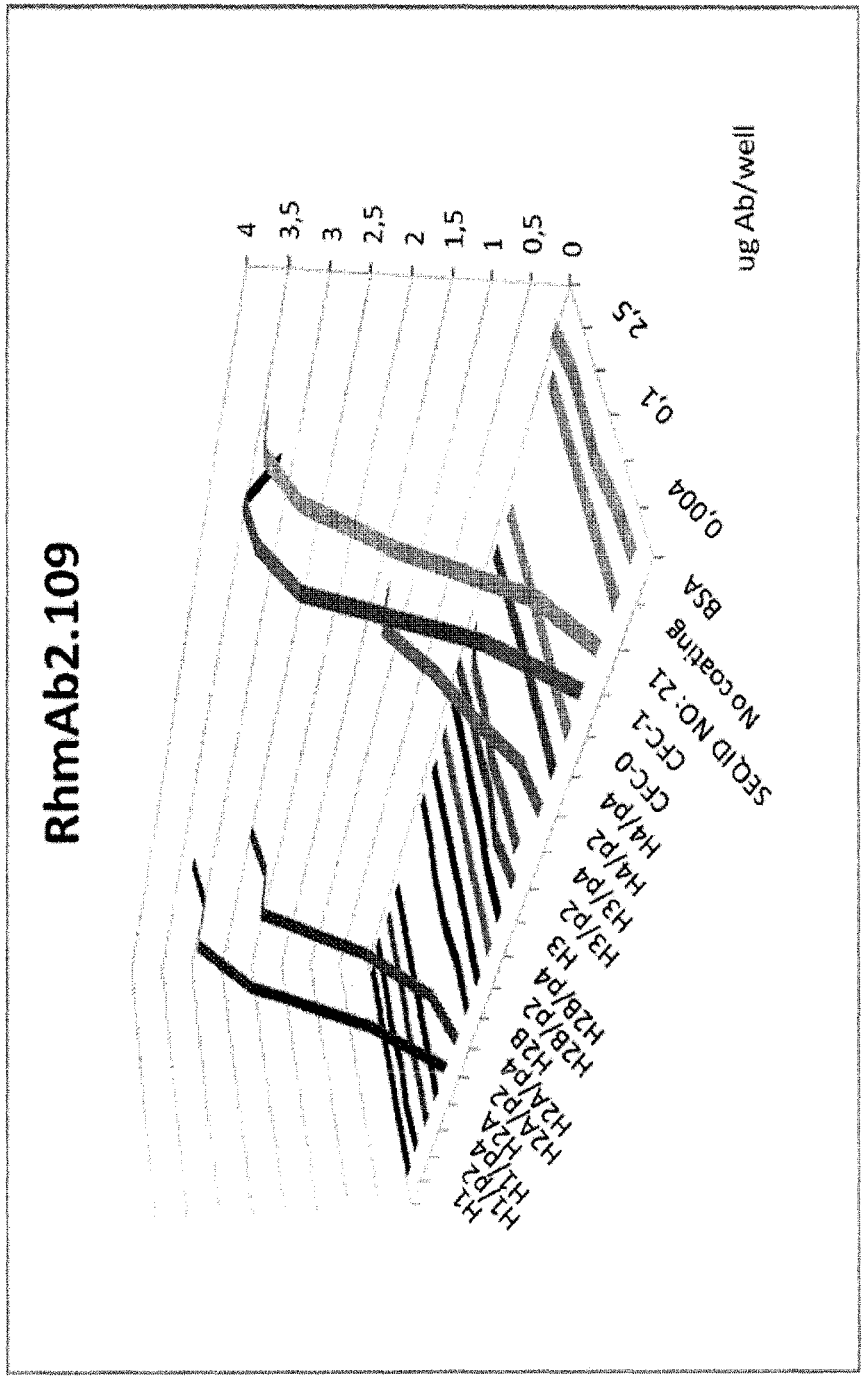
Figure 11D:
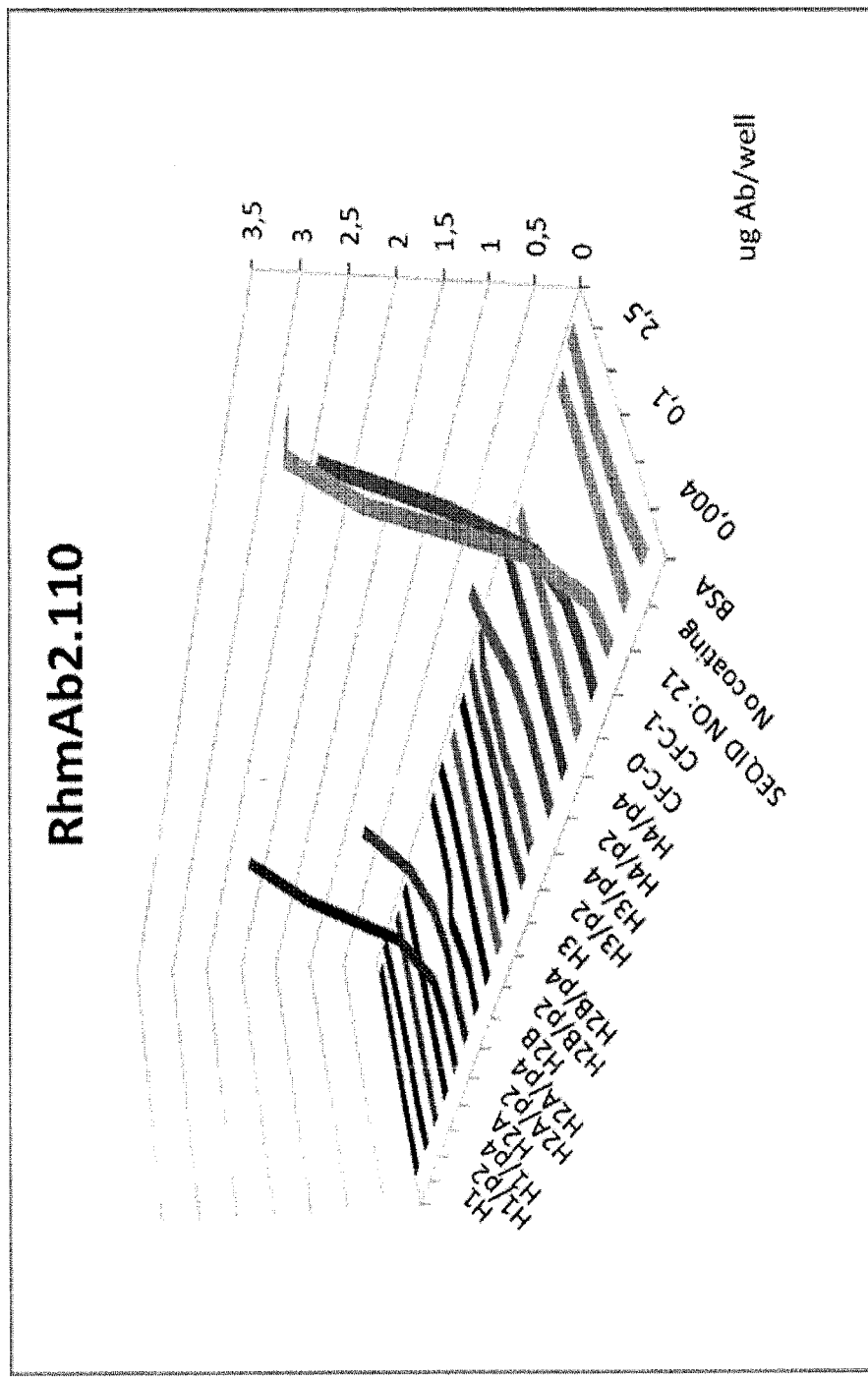
Figure 11E:
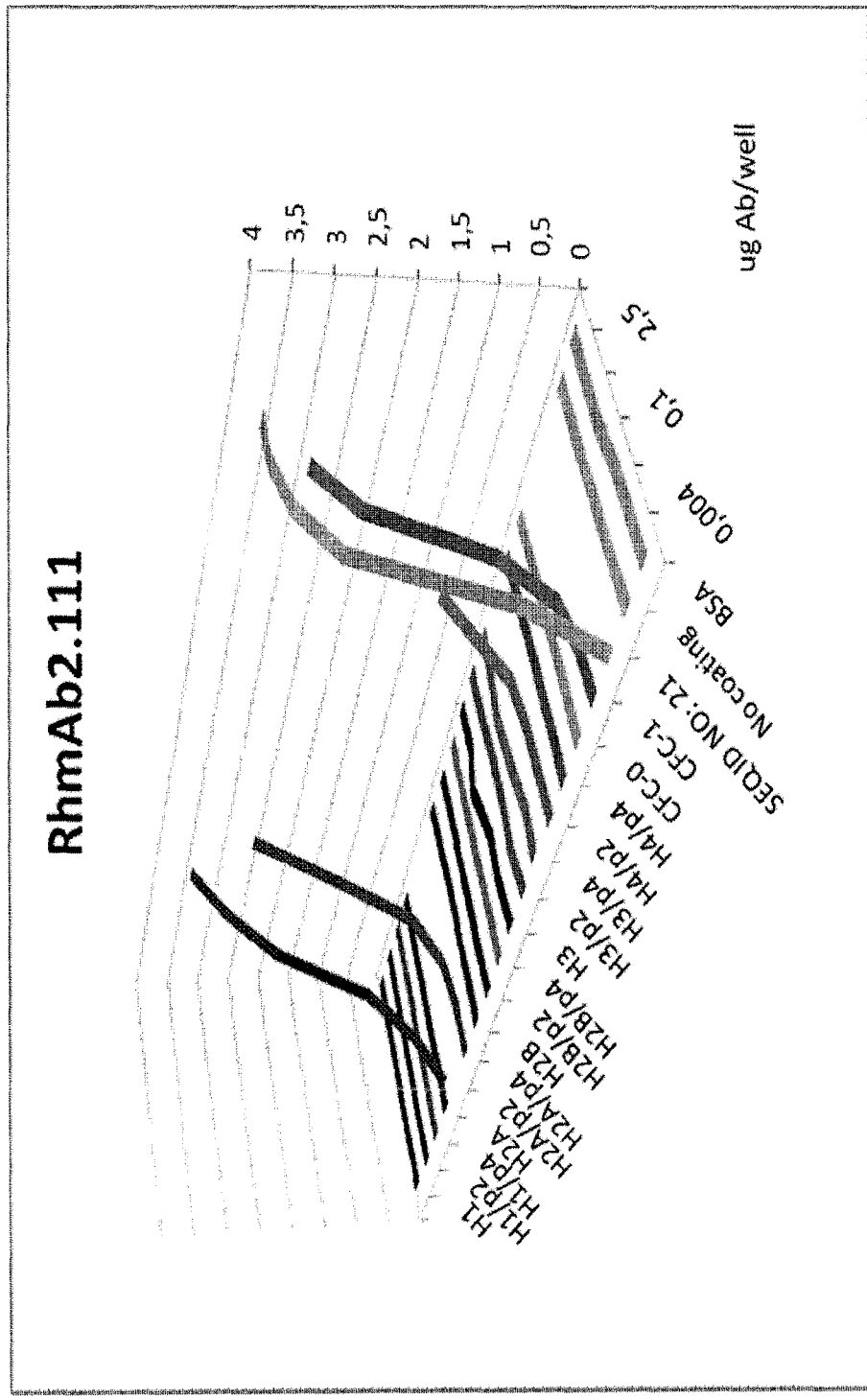
Figure 11F:
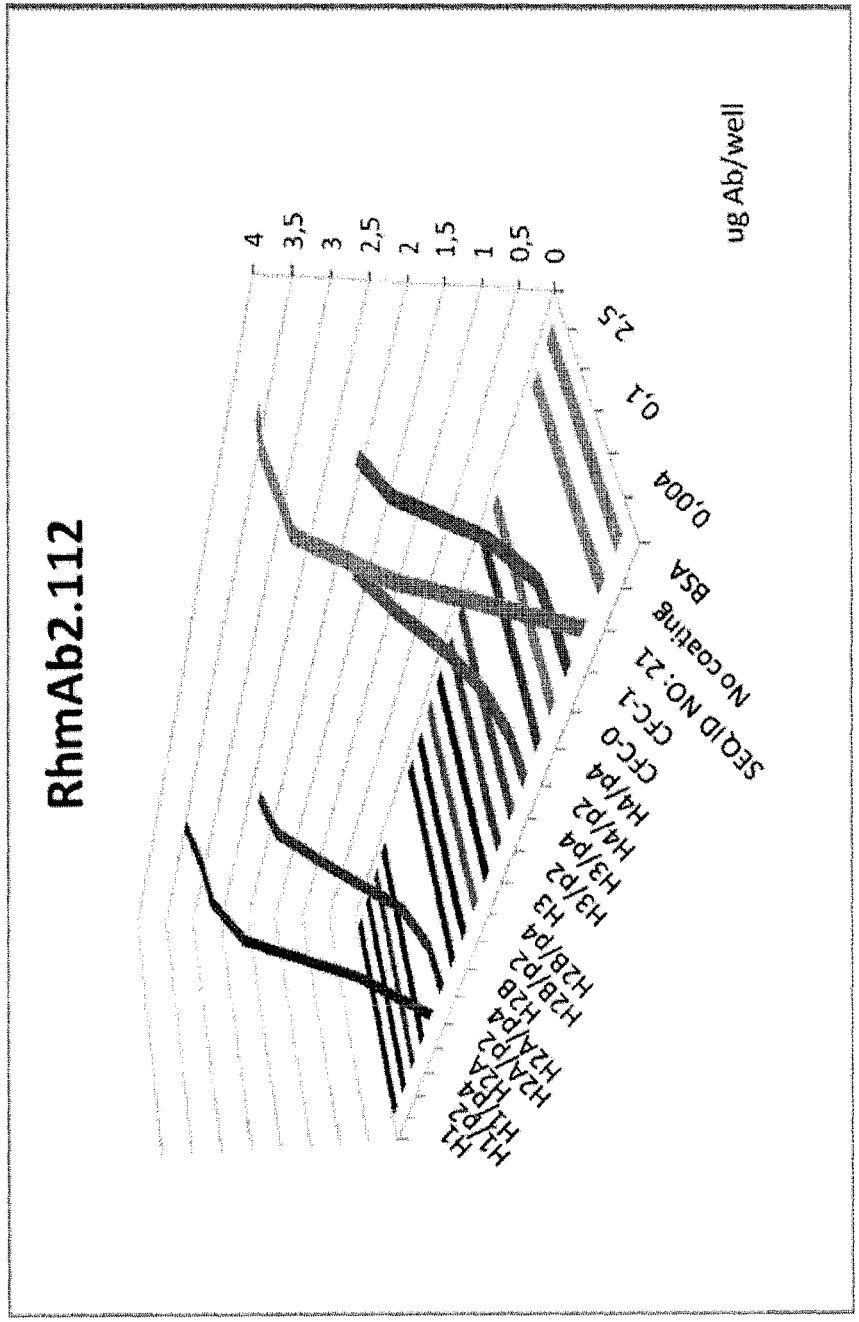
Figure 11G:
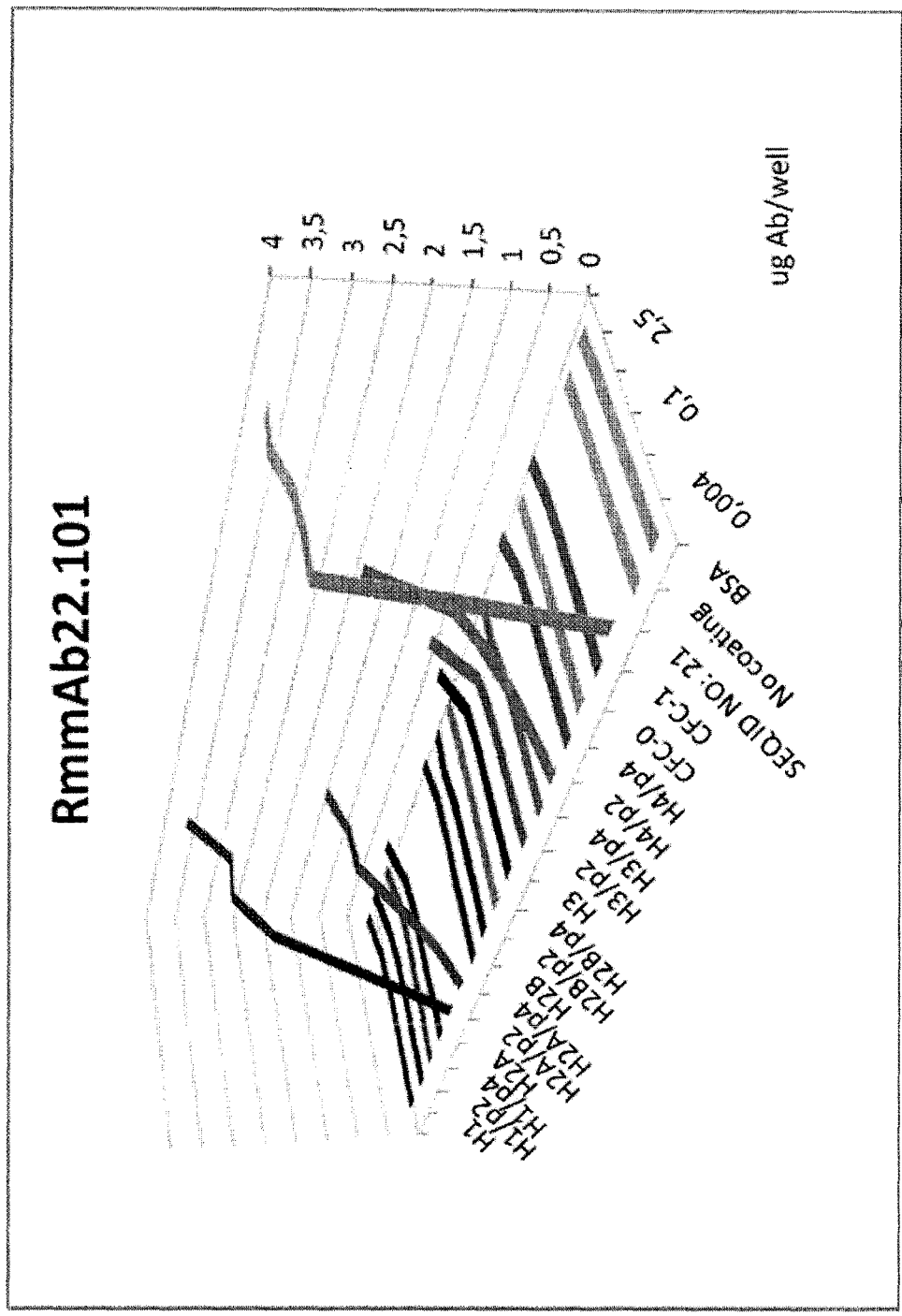
Figure 11H:
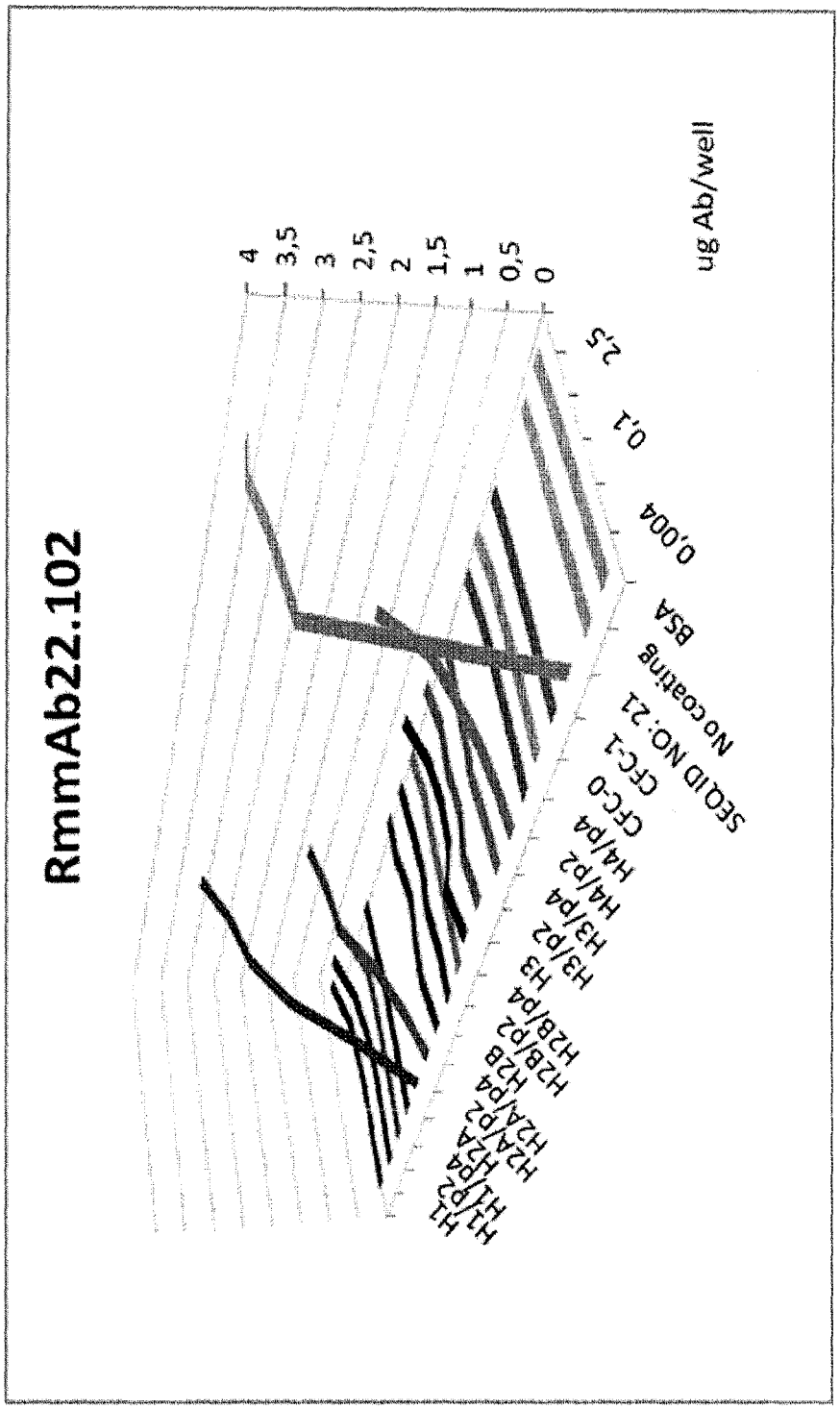

Similar results were obtained in the CAIA animal experiments as with the human antibodies RhmAb2.108, RhmAb2.109, RhmAb2.110, RhmAb2.111 and RhmAb2.112. The Mouse monoclonals RmmAb22.101 and RmmAb22.102 abolished the clinical signs of arthritis (FIG. 10).

Figure 1E:
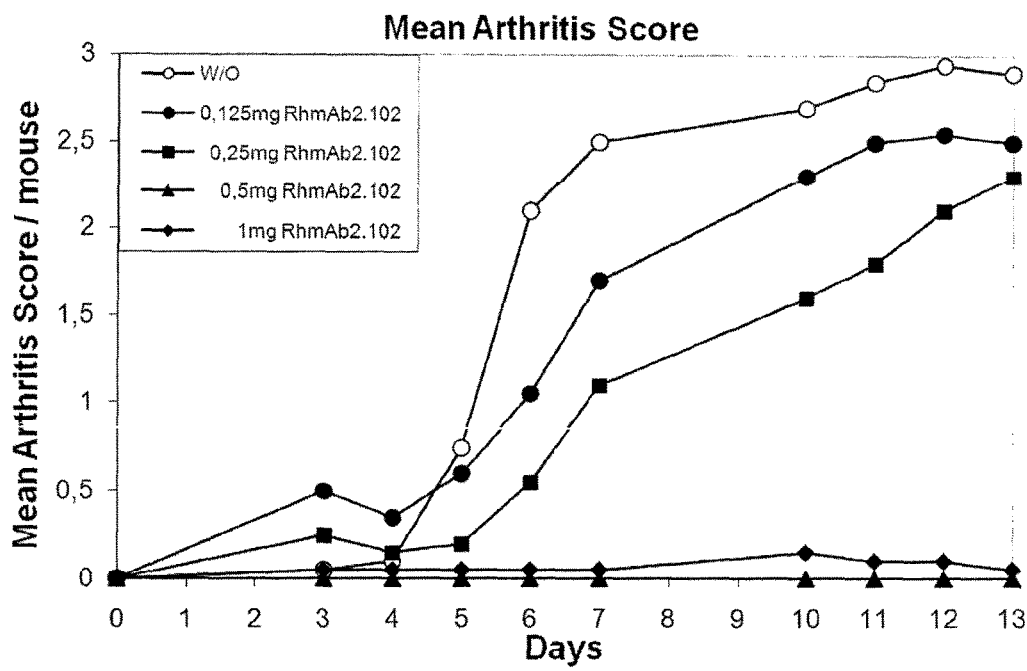
Figure 1F:
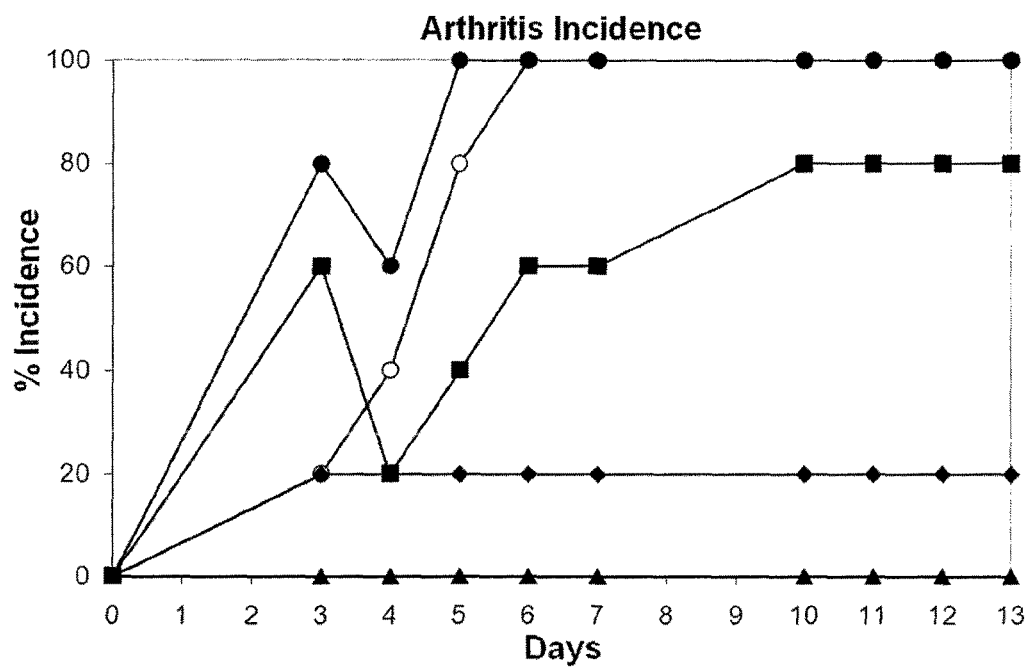

FIGS. 1E and 1F show an independent CAIA experiment in which the clinical dose for RhmAb2.102 has been evaluated. The lowest dose that gave maximum inhibition was 0.5 mg Ab/mouse which corresponds to 28 mg/kg at IP injection.

From these experiments, it is concluded that the specific epitopes recognized by monoclonal antibodies selected from the group consisting of RhmAb2.102, RhmAb2.108, RhmAb2.109, RhmAb2.110, RhmAb2.111 and RhmAb2.112, RmmAb22.101, and RmmAb22.102 play an important role in the treatment or prevention of inflammatory diseases. Specific masking of these epitopes may, therefore, be an effective therapy of inflammatory diseases, in particular, rheumatoid arthritis.

In order to further analyze the antigen or antigens recognized by these monoclonal antibodies, they were tested for their reactivity toward cell extracts that were deiminated using Peptidylarginine deiminase (PAD enzyme) as described in Example 3. Western blots containing hPAD2 or hPAD4 transfected COS-1 lysates that were post-lytically deiminated were incubated with the monoclonal antibodies RhmAb2.101 and RhmAb2.102. It was observed that only strips incubated with RhmAb2.102 showed reactivity with a doublet of proteins with a molecular weight of approximately 15 kilodaltons and 17 kilodaltons.

WO 2004/078098 discloses antibodies specific for citrullinated peptide/MHC class II complexes to inhibit T cell activation. These antibodies do not bind to the separate peptide or MHC class II molecule but only to the complex of the peptide and the MHC class II molecule. The antibodies disclosed herein are different from the antibodies disclosed in WO 2004/078098 since they recognize the individual peptides and proteins as disclosed herein. Moreover, the antibodies recognize a polypeptide in a Western blot that could not be a complex between a peptide and an MHC class II molecule, since the complex between an MHC molecule and a citrullinated peptide would never survive the reducing conditions of an SDS gel used in the immunoblot procedure. The epitopes recognized by the binding molecules as disclosed herein are, therefore, different from the antibodies disclosed in WO 2004/078098. Moreover, the antibodies as disclosed herein are not specifically reactive with a complex of a peptide and an MHC class II molecule.

The above-described experiments and considerations led to the conclusion that there is a clear correlation between the ability to prevent clinical signs of inflammatory diseases and reactivity with citrullinated epitopes on p15 and p17.

Similar data were obtained when human monoclonal antibodies RhmAb2.101 and RhmAb2.102 were used in immunoprecipitation experiments as detailed in Example 5.

Immunoprecipitations with RhmAb2.102, on both human PAD2- and PAD4-deiminated COS-1 lysates, revealed prominent p15 and p17 protein bands.

The intensity of recognition of p15 and p17 proteins, therefore, seems to correlate well with the therapeutic properties of these antibodies (FIGS. 1A-1D).

Whether or not an antibody is reactive with p15 or p17 may easily be established by performing immunoprecipitation or Western blot analysis as detailed in Examples 4 and 5. Alternatively, competition experiments with RhmAb2.102, RhmAb2.108, RhmAb2.109, RhmAb2.110, RhmAb2.111 and RhmAb2.112. RmmAb22.101, and RmmAb22.102, may be performed using either Western blots containing deiminated COS-1 lysates or purified deiminated p15 and/or p17 proteins in Western blot or ELISA.

Proteins p15 and p17 were further characterized by Matrix-assisted laser desorption/ionization-time of flight mass spectrometry (MALDI-TOF MS) as detailed in Example 6. Since the genome of the African Green Monkey is not completely sequenced, all other mammal genome databases were screened for homology with the peptides found with MALDI-TOF MS. Proteins found with a high degree of homology turned out to be histones. This is shown in Table 3 (Example 6).

The disclosure, therefore, also relates to a binding molecule specifically reactive with a citrullinated epitope on histones for use in the treatment or prevention of inflammatory diseases.

The citrullination of histones by enzymatic action of PAD is well documented and, therefore, citrullinated histones may very well be produced in vitro. These citrullinated histones may then be used as a substrate in an enzymatic binding assay to screen and select for other specific binding molecules such as peptides and antibodies reactive with epitopes on citrullinated p15 and p17, i.e., histones. Preferably, specific binding molecules are selected that compete with antibodies RhmAb2.102, RhmAb2.108, RhmAb2.109, RhmAb2.110, RhmAb2.111 and RhmAb2.112, RmmAb22.101, and RmmAb22.102 for binding to p15 and/or p17.

In this document and in its claims, the verb "to comprise" and its conjugations are used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

In order to further analyze which deiminated histone or histones are involved in the therapeutic action of RhmAb2.102, RhmAb2.108, RhmAb2.109, RhmAb2.110, RhmAb2.111 RhmAb2.112, RmmAb22.101, and RmmAb22.102, commercially available histones (H1, H2A, H2B, H3 and H4) were deiminated with human peptidylarginine deiminase (PAD, EC 3.5.3.15) enzymes (huPAD2 or huPAD4). Deiminated as well as non-deiminated histones were coated on 96-well ELISA plates and incubated with serial dilutions of RhmAb2.101 and RhmAb2.102. The results are shown in Table 6 and FIG. 2.

Figure 2A:
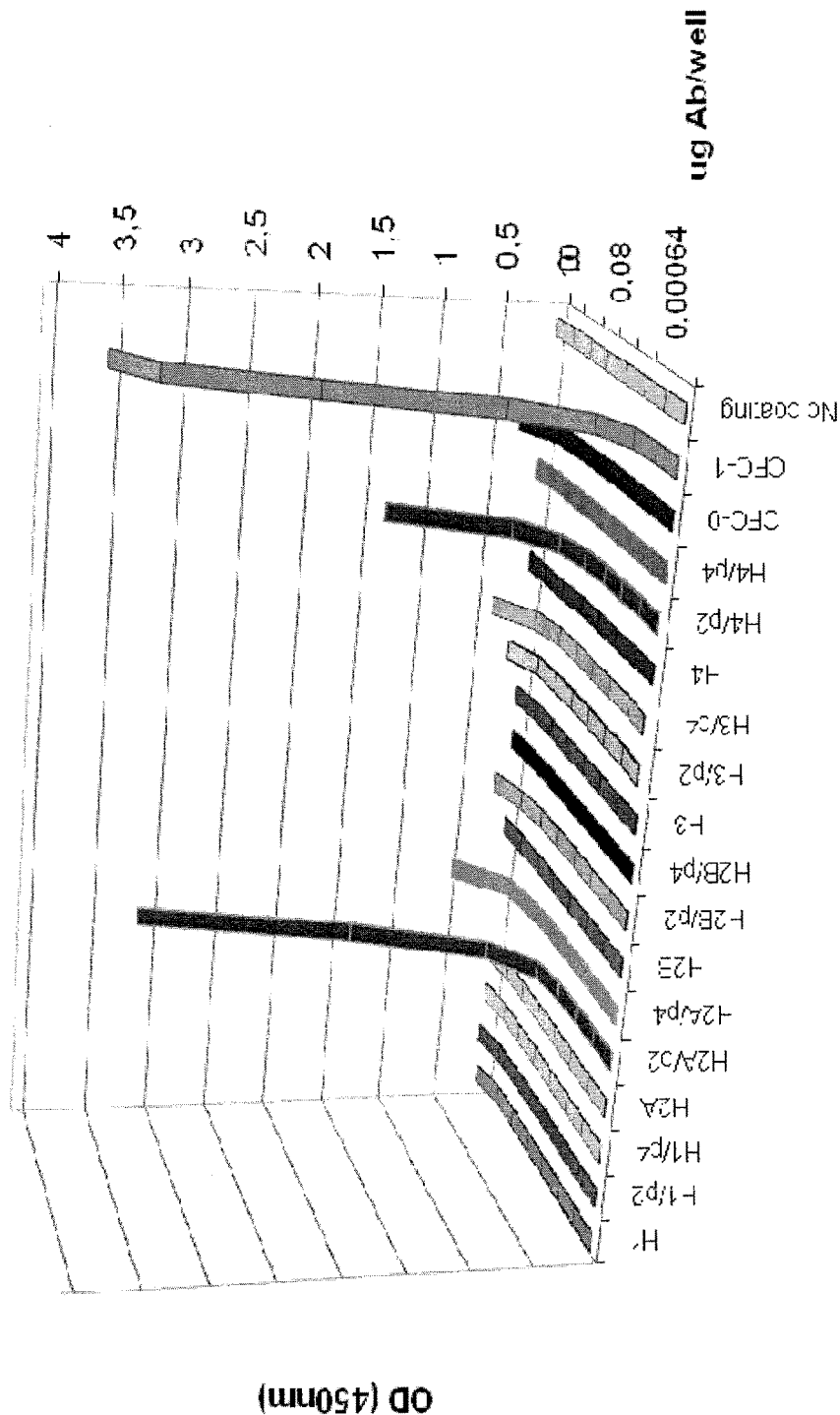
FIGS. 2A and 2B: An enzyme-linked immunosorbent assay (ELISA) was used to test the affinity of RhmAb2.101 (FIG. 2A) and RhmAb2.102 (FIG. 2B) for human recombinant histones (H1, H2A, H2B, H3 and H4) deiminated with huPAD2 or huPAD4. Deiminated as well as non-deiminated histones were immobilized on 96-well ELISA plates (0.3 CFC-1 and CFC-0 were coated at the same concentration and served as positive and negative controls, respectively, for specific anti-citrulline reactivity and as coating controls. Non-coated wells were used to test for aspecific binding of the antibodies. Coated wells were incubated with antibody dilution series ranging from 10 µg/well down to 0.000128 µg/well for 1 hour at RT (z-axis). Detection of bound anti-citrulline antibodies was performed by incubating the wells with rabbit anti-human HRP (1:2000) for 1 hour at RT followed by incubation with TMB substrate. The resulting OD (y-axis) is a measure for antibody binding. H1-recombinant histone 1; H1/p2-huPAD2 recombinant histone 1; H1/p4-huPAD4 recombinant histone 1, and so forth (x-axis).
Figure 2B:
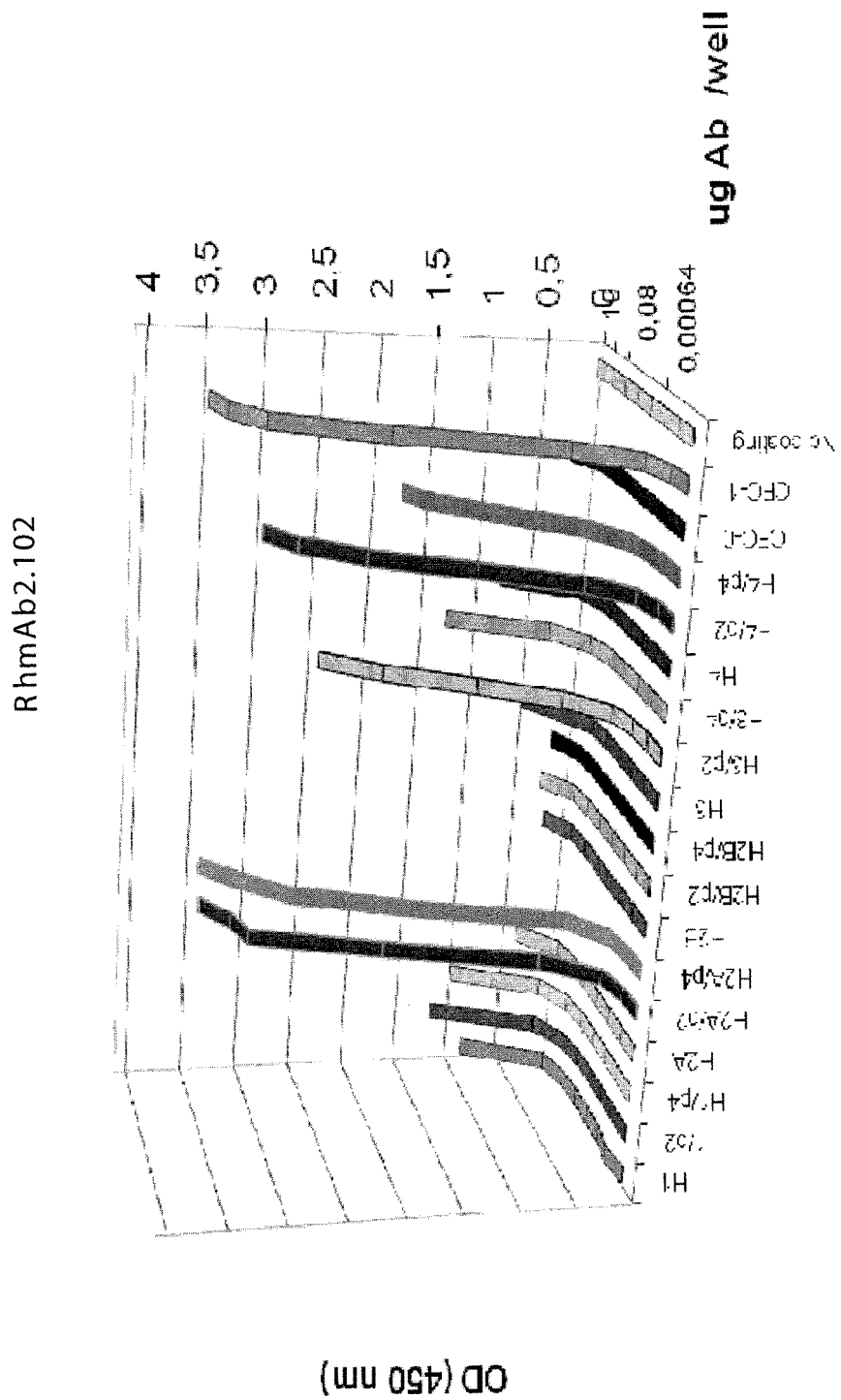

It is evident from the results shown in FIG. 2B that deiminated histone 2A, histone 3, and histone 4 are recognized by the therapeutic antibody RhmAb2.102, but with no, or significantly lower, affinity by RhmAb2.101 (FIGS. 2A and 2B).

Furthermore, these results show that this difference in affinity between RhmAb2.102 and RhmAb2.101 is highest for human PAD2- and/or PAD4-deiminated H2A, human PAD2-deiminated histone 3, and human PAD4- and/or PAD2-deiminated histone 4.

These data correlate well with the effect of these antibodies on the clinical signs of arthritis in the experimental CAIA model, in which RhmAb2.102 abolishes the clinical signs of arthritis, whereas RhmAb2.101 has no effect on the clinical signs of arthritis (FIGS. 1C and 1D).

Therefore, it is shown that a deiminated epitope on H2A/p4 and H2A/p2 or its structural mimics play a crucial role in the RA inflammatory cascade. The same is true for deiminated epitopes on H3/p2, H4/p2 and H4/p4 since RhmAb2.102 shows higher affinity for these histones as compared to RhmAb2.101 (FIGS. 2A and 2B).

A mimic is, for instance, a molecule with an acceptable level of equivalent activity, which, in this case, would include as being recognized with higher affinity by RhmAb2.102 as compared to RhmAb2.101.

The disclosure, therefore, relates to a specific binding molecule as described above, reactive with a citrullinated epitope on human PAD4- or human PAD2-deiminated human histone 2A or histone 4, or on human PAD2-deiminated histone H3.

Figure 3A:
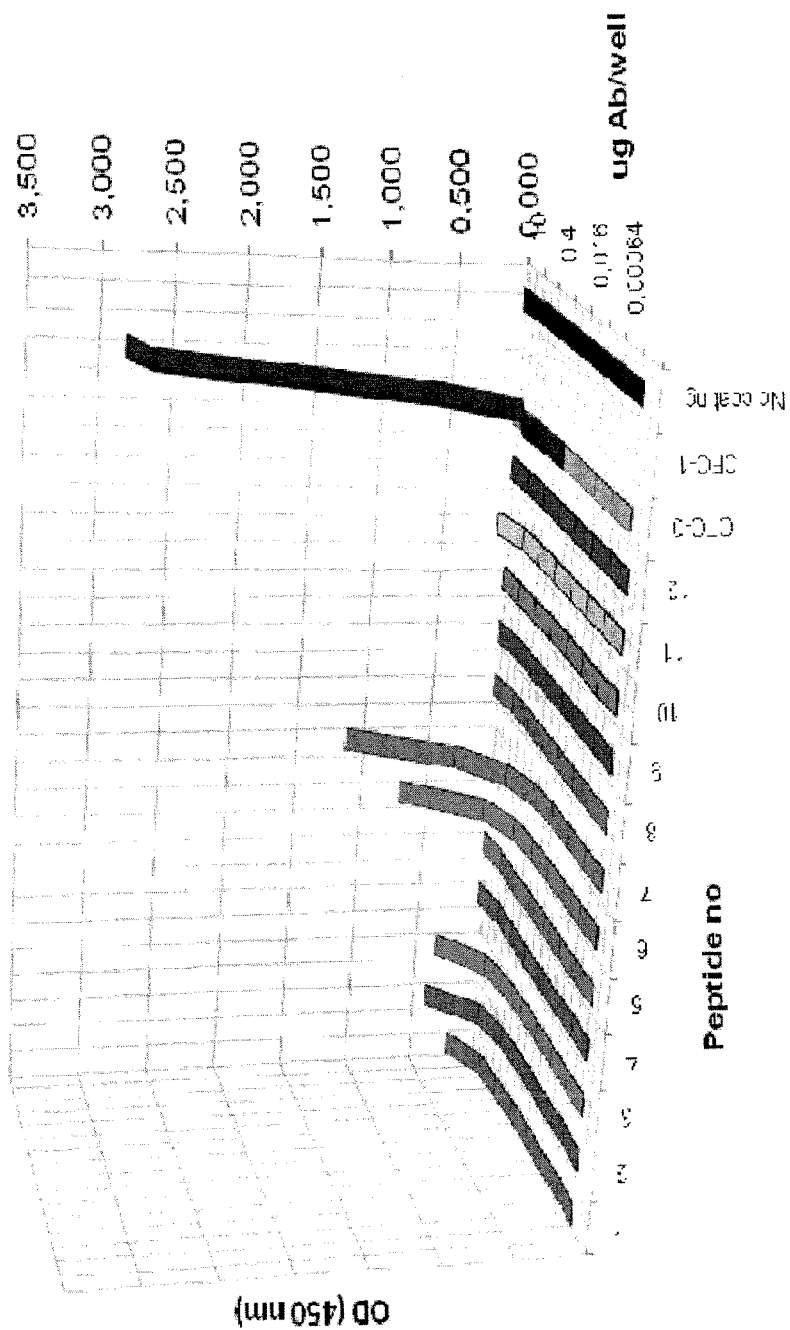
FIGS. 3A and 3B: An enzyme-linked immunosorbent assay (ELISA) was used to test the affinity of a) RhmAb2.101 and b) RhmAb2.102 for citrulline-containing peptides derived from human histones H2A. Biotin and citrulline-containing peptides derived from histone 2A were immobilized on NEUTRAVIDIN®-coated 96-well ELISA plates (0.3 µg/well). CFC-1 and CFC-0 were coated at the same concentration and served as positive and negative controls, respectively, for specific anti-citrulline reactivity and as coating controls. Non-coated wells were used to test for aspecific binding of the antibodies. Coated wells were incubated with antibody dilution series ranging from 10 µg/well down to 0.000128 µg/well for 1 hour at RT (z-axis). Detection of bound anti-citrulline antibodies was performed by incubating the wells with rabbit anti-human HRP (1:2000) for 1 hour at RT followed by incubation with TMB substrate. The resulting OD (y-axis) is a measure for antibody binding.
Figure 3B:
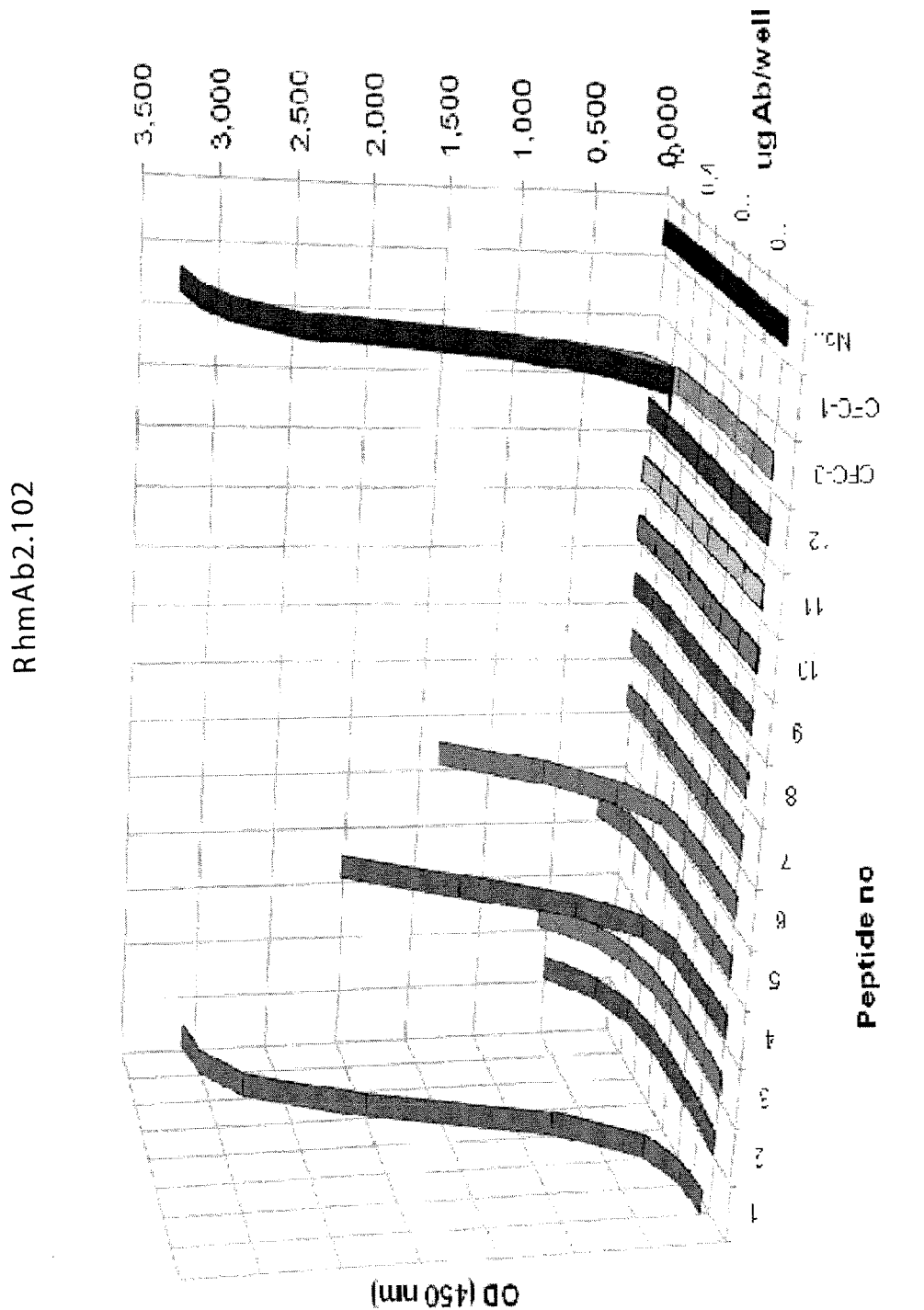

To further pinpoint the exact citrullinated epitope on H2A that is recognized by RhmAb2.102, biotin-labeled peptides as shown in Table 4 were synthesized containing potential deimination sites of histone 2A. These peptides were coated on 96-well NEUTRAVIDIN®-ELISA plates and incubated with serial dilutions of RhmAb2.101 and RhmAb2.102. The results are shown in FIGS. 3A and 3B.

TABLE 6

A: Reactivity of deiminated histones with RhmAb2.101, shown in FIG. 2A

| 2.101 | H1 | H1/p2 | H1/p4 | H2A | H2A/p2 | H2A/p4 | H2B | H2B/p2 | H2B/p4 |
|---|---|---|---|---|---|---|---|---|---|
| 10 | 0.141 | 0.151 | 0.126 | 0.14 | 3.141 | 0.522 | 0.105 | 0.216 | 0.114 |
| 2 | 0.072 | 0.09 | 0.084 | 0.089 | 1.473 | 0.159 | 0.085 | 0.12 | 0.087 |
| 0.4 | 0.067 | 0.08 | 0.083 | 0.085 | 0.426 | 0.11 | 0.069 | 0.077 | 0.069 |
| 0.08 | 0.064 | 0.072 | 0.072 | 0.076 | 0.128 | 0.073 | 0.067 | 0.067 | 0.064 |
| 0.016 | 0.061 | 0.064 | 0.072 | 0.073 | 0.076 | 0.073 | 0.065 | 0.062 | 0.064 |
| 0.0032 | 0.061 | 0.066 | 0.069 | 0.072 | 0.063 | 0.065 | 0.062 | 0.064 | 0.061 |
| 0.00064 | 0.06 | 0.067 | 0.069 | 0.071 | 0.059 | 0.064 | 0.059 | 0.06 | 0.061 |
| 0.000128 | 0.064 | 0.063 | 0.071 | 0.066 | 0.058 | 0.063 | 0.058 | 0.065 | 0.062 |

| H3 | H3/p2 | H3/p4 | H4 | H4/p2 | H4/p4 | CFC-0 | CFC-1 | No coating |
|---|---|---|---|---|---|---|---|---|
| 0.115 | 0.217 | 0.383 | 0.111 | 1.341 | 0.116 | 0.303 | 3.587 | 0.069 |
| 0.075 | 0.087 | 0.146 | 0.093 | 0.412 | 0.073 | 0.103 | 3.26 | 0.055 |
| 0.065 | 0.073 | 0.076 | 0.089 | 0.154 | 0.077 | 0.084 | 2.13 | 0.058 |
| 0.074 | 0.067 | 0.069 | 0.066 | 0.084 | 0.065 | 0.066 | 0.807 | 0.067 |
| 0.071 | 0.069 | 0.079 | 0.067 | 0.06 | 0.063 | 0.056 | 0.249 | 0.053 |
| 0.072 | 0.079 | 0.076 | 0.072 | 0.067 | 0.066 | 0.056 | 0.097 | 0.057 |
| 0.074 | 0.077 | 0.074 | 0.07 | 0.062 | 0.063 | 0.057 | 0.072 | 0.052 |
| 0.079 | 0.104 | 0.104 | 0.073 | 0.08 | 0.063 | 0.056 | 0.065 | 0.051 |

B: Reactivity of deiminated histones with. RhmAb2.102, shown in FIG. 2B

| 2.102 | H1 | H1/p2 | H1/p4 | H2A | H2A/p2 | H2A/p4 | H2B | H2B/p2 | H2B/p4 |
|---|---|---|---|---|---|---|---|---|---|
| 10 | 0.9 | 1.214 | 1.045 | 0.428 | 3.411 | 3.425 | 0.247 | 0.31 | 0.229 |
| 2 | 0.178 | 0.304 | 0.27 | 0.115 | 3.179 | 3.134 | 0.076 | 0.086 | 0.069 |
| 0.4 | 0.089 | 0.119 | 0.103 | 0.071 | 3.085 | 2.722 | 0.056 | 0.06 | 0.054 |
| 0.08 | 0.059 | 0.069 | 0.065 | 0.06 | 1.963 | 1.747 | 0.054 | 0.053 | 0.052 |
| 0.016 | 0.054 | 0.058 | 0.059 | 0.057 | 0.628 | 0.426 | 0.065 | 0.052 | 0.052 |
| 0.0032 | 0.055 | 0.058 | 0.057 | 0.056 | 0.161 | 0.135 | 0.05 | 0.052 | 0.052 |
| 0.00064 | 0.102 | 0.058 | 0.058 | 0.057 | 0.077 | 0.075 | 0.052 | 0.052 | 0.055 |
| 0.000128 | 0.053 | 0.057 | 0.057 | 0.058 | 0.063 | 0.062 | 0.052 | 0.051 | 0.053 |

| H3 | H3/p2 | H3/p4 | H4 | H4/p2 | H4/p4 | CFC-0 | CFC-1 | No coating |
|---|---|---|---|---|---|---|---|---|
| 0.549 | 2.442 | 1.311 | 0.825 | 2.979 | 1.776 | 0.26 | 3.478 | 0.08 |
| 0.275 | 1.935 | 0.439 | 0.208 | 2.735 | 1.556 | 0.086 | 3.377 | 0.053 |
| 0.08 | 1.177 | 0.166 | 0.091 | 2.218 | 0.986 | 0.06 | 3.115 | 0.05 |
| 0.062 | 0.493 | 0.093 | 0.067 | 1.343 | 0.432 | 0.05 | 2.145 | 0.046 |
| 0.058 | 0.155 | 0.076 | 0.061 | 0.491 | 0.167 | 0.05 | 0.702 | 0.047 |
| 0.058 | 0.08 | 0.065 | 0.06 | 0.151 | 0.077 | 0.049 | 0.178 | 0.047 |
| 0.056 | 0.062 | 0.062 | 0.06 | 0.073 | 0.058 | 0.048 | 0.077 | 0.045 |
| 0.058 | 0.066 | 0.06 | 0.06 | 0.073 | 0.055 | 0.047 | 0.058 | 0.046 |

TABLE 7

Reactivity of selected peptides with mAbs RhmAb2.102 and RhmAb2.101 as indicated

| 2.101 | peptide 1 | 2 | 3 | 4 | 5 | 6 | 7 | 8 | 9 | 10 | 11 | 12 | CFC-0 | CFC-1 | No coating |
|---|---|---|---|---|---|---|---|---|---|---|---|---|---|---|---|
| 10 ng/well | 0.266 | 0.457 | 0.393 | 0.095 | 0.083 | 0.750 | 1.178 | 0.090 | 0.087 | 0.073 | 0.148 | 0.072 | 0.095 | 2.841 | 0.076 |
| 2 | 0.102 | 0.136 | 0.121 | 0.048 | 0.051 | 0.218 | 0.459 | 0.053 | 0.053 | 0.069 | 0.064 | 0.053 | 0.071 | 2.717 | 0.055 |
| 0.4 | 0.086 | 0.071 | 0.068 | 0.051 | 0.064 | 0.090 | 0.174 | 0.050 | 0.056 | 0.061 | 0.058 | 0.050 | 0.068 | 1.827 | 0.050 |
| 0.08 | 0.062 | 0.054 | 0.053 | 0.056 | 0.051 | 0.062 | 0.080 | 0.051 | 0.052 | 0.052 | 0.051 | 0.050 | 0.065 | 0.951 | 0.051 |
| 0.016 | 0.057 | 0.049 | 0.049 | 0.051 | 0.054 | 0.058 | 0.055 | 0.050 | 0.049 | 0.048 | 0.050 | 0.050 | 0.055 | 0.492 | 0.050 |
| 0.0032 | 0.061 | 0.052 | 0.049 | 0.052 | 0.054 | 0.051 | 0.050 | 0.050 | 0.050 | 0.055 | 0.050 | 0.051 | 0.063 | 0.583 | 0.051 |
| 0.00064 | 0.049 | 0.038 | 0.050 | 0.040 | 0.053 | 0.052 | 0.052 | 0.050 | 0.048 | 0.066 | 0.047 | 0.045 | 0.064 | 0.548 | 0.050 |
| 0.000128 | 0.060 | 0.052 | 0.045 | 0.049 | 0.047 | 0.046 | 0.047 | 0.048 | 0.049 | 0.051 | 0.047 | 0.052 | 0.059 | 0.537 | 0.051 |

| 2.102 | 1 | 2 | 3 | 4 | 5 | 6 | 7 | 8 | 9 | 10 | 11 | 12 | CFC-0 | CFC-1 | No coating |
|---|---|---|---|---|---|---|---|---|---|---|---|---|---|---|---|
| 10 | 3.112 | 0.552 | 0.619 | 2.056 | 0.239 | 1.410 | 0.080 | 0.082 | 0.090 | 0.091 | 0.088 | 0.083 | 0.870 | 3.271 | 0.074 |
| 2 | 3.048 | 0.270 | 0.286 | 1.300 | 0.111 | 0.752 | 0.059 | 0.060 | 0.063 | 0.070 | 0.067 | 0.067 | 0.242 | 3.206 | 0.053 |
| 0.4 | 2.804 | 0.136 | 0.154 | 0.564 | 0.082 | 0.333 | 0.064 | 0.061 | 0.057 | 0.051 | 0.064 | 0.061 | 0.115 | 3.060 | 0.051 |
| 0.08 | 2.039 | 0.086 | 0.091 | 0.192 | 0.066 | 0.123 | 0.062 | 0.060 | 0.060 | 0.058 | 0.064 | 0.060 | 0.088 | 2.656 | 0.050 |
| 0.016 | 0.843 | 0.065 | 0.070 | 0.084 | 0.065 | 0.075 | 0.061 | 0.063 | 0.064 | 0.066 | 0.069 | 0.057 | 0.071 | 1.460 | 0.045 |
| 0.0032 | 0.300 | 0.062 | 0.062 | 0.078 | 0.063 | 0.058 | 0.064 | 0.060 | 0.062 | 0.068 | 0.057 | 0.059 | 0.067 | 0.916 | 0.046 |
| 0.00064 | 0.160 | 0.055 | 0.058 | 0.063 | 0.067 | 0.058 | 0.057 | 0.057 | 0.059 | 0.056 | 0.060 | 0.056 | 0.066 | 0.621 | 0.050 |
| 0.000128 | 0.128 | 0.075 | 0.063 | 0.058 | 0.059 | 0.054 | 0.056 | 0.055 | 0.055 | 0.057 | 0.059 | 0.056 | 0.063 | 0.749 | 0.047 |

TABLE 8

Reactivity of selected peptides with mAbs RhmAb2.102 and RhmAb2.101 as indicated.

| | msFib α XH | msFIB α XG | huFib α XH | huFib α XG | msFib β XG | msVim XS/XL | cfc1 XG | cf0 | Neutra | blanc |
|---|---|---|---|---|---|---|---|---|---|---|
| 2.101 (µg/well) | | | | | | | | | | |
| 10 | 0.120 | 3.876 | 0.177 | 3.778 | 2.538 | 0.282 | 3.780 | 0.154 | 0.088 | 0.069 |
| 2 | 0.081 | 3.730 | 0.124 | 3.601 | 1.260 | 0.144 | 3.612 | 0.115 | 0.120 | 0.066 |
| 0.4 | 0.074 | 2.616 | 0.107 | 2.497 | 0.457 | 0.123 | 2.581 | 0.109 | 0.098 | 0.061 |
| 0.08 | 0.073 | 0.893 | 0.100 | 0.798 | 0.203 | 0.119 | 1.070 | 0.115 | 0.099 | 0.061 |
| 0.016 | 0.087 | 0.267 | 0.112 | 0.249 | 0.132 | 0.129 | 0.459 | 0.126 | 0.135 | 0.064 |
| 0.0032 | 0.102 | 0.143 | 0.118 | 0.151 | 0.119 | 0.128 | 0.325 | 0.123 | 0.137 | 0.069 |
| 0.00064 | 0.130 | 0.130 | 0.121 | 0.254 | 0.123 | 0.134 | 0.322 | 0.123 | 0.124 | 0.062 |
| 0.000128 | 0.114 | 0.144 | 0.139 | 0.146 | 0.119 | 0.147 | 0.292 | 0.136 | 0.113 | 0.059 |
| 2.102 (µg/well) | | | | | | | | | | |
| 10 | 0.154 | 3.028 | 0.179 | 2.727 | 3.802 | 3.694 | 3.892 | 0.334 | 0.088 | 0.066 |
| 2 | 0.091 | 1.902 | 0.116 | 1.511 | 3.154 | 2.767 | 3.968 | 0.138 | 0.080 | 0.062 |
| 0.4 | 0.076 | 0.773 | 0.090 | 0.521 | 1.670 | 1.448 | 3.794 | 0.111 | 0.075 | 0.060 |
| 0.08 | 0.076 | 0.237 | 0.080 | 0.186 | 0.515 | 0.515 | 3.026 | 0.094 | 0.073 | 0.061 |
| 0.016 | 0.081 | 0.107 | 0.080 | 0.103 | 0.174 | 0.201 | 1.223 | 0.102 | 0.089 | 0.061 |
| 0.0032 | 0.085 | 0.125 | 0.123 | 0.125 | 0.120 | 0.142 | 0.506 | 0.124 | 0.103 | 0.060 |
| 0.00064 | 0.088 | 0.116 | 0.124 | 0.125 | 0.133 | 0.154 | 0.345 | 0.152 | 0.134 | 0.060 |
| 0.000128 | 0.089 | 0.119 | 0.120 | 0.115 | 0.118 | 0.133 | 0.288 | 0.139 | 0.119 | 0.059 |

It was observed that peptide 1 (AAASGXGKQGGK, SEQ ID NO: 21) was recognized by the therapeutic antibody RhmAb2.102 but not by RhmAb2.101 (Table 4 and FIGS. 3A and 3B). The same holds true for the deiminated epitopes on peptides 4 and 6 (Table 4) since RhmAb2.102 shows higher affinity for these peptides than RhmAb2.101 (FIGS. 3A and 3B). Therefore, it has therewith been shown that the deiminated epitope or the structural equivalents or mimics thereof on peptides 1, 4 and 6 play a crucial role in the RA inflammatory cascade. This antibody recognition pattern is very similar to the recognition pattern of H2A/p4 and H2A/p2. Therefore, it was concluded that the specific binding molecules according to the disclosure may also be defined by their reactivity toward peptides 1, 4 and 6; SEQ ID NO: 21, SEQ ID NO: 24 and SEQ ID NO: 26, respectively. Each of these citrulline-containing peptides or derivatives thereof, individually, or a combination of such peptides, or structures containing one or more of such peptide sequences, may be used to generate specific binding molecules such as antibodies according to the disclosure. Such antibodies may then be selected toward any of the other antigens as disclosed herein for optimal reactivity.

TABLE 4

Histone 2A citrulline-containing peptides

| Peptide Number | Sequence ID NO: | Amino acid sequence |
|---|---|---|
| 1 | Sequence ID NO: 21 | A A A S G X G K Q G G K |
| 2 | Sequence ID NO: 22 | A K A K S X S S R A G L |
| 3 | Sequence ID NO: 23 | K S R S S X A G L Q F P |

TABLE 4-continued

Histone 2A citrulline-containing peptides

| Peptide Number | Sequence ID NO: | Amino acid sequence |
|---|---|---|
| 4 | Sequence ID NO: 24 | Q F P V G X V H R L L R |
| 5 | Sequence ID NO: 25 | V G R V H X L L R K G N |
| 6 | Sequence ID NO: 26 | V H R L L X K G N Y S E |
| 7 | Sequence ID NO: 27 | G N Y S E X V G A G A P |
| 8 | Sequence ID NO: 28 | A G N A A X D N K K T R |
| 9 | Sequence ID NO: 29 | D N K K T X I I P R H L |
| 10 | Sequence ID NO: 30 | T R I I P X H L Q L A I |
| 11 | Sequence ID NO: 31 | L Q L A I X N D E E L N |
| 12 | Sequence ID NO: 32 | N K L L G X V T I A Q G |

X denotes a citrulline residue

Biotin-labeled and citrulline-containing fibrinogen and vimentin peptides (Table 5) were also tested for reactivity with the therapeutic antibodies. Peptides were coated on 96-well NEUTRAVIDIN®-ELISA plates. Subsequently, serial dilutions of RhmAb2.101 and RhmAb2.102 were applied to the coated plates. The results are shown in Table 8 and FIGS. 4A and 4B.

TABLE 5

Fibrinogen and vimentin citrulline-containing peptides

| Peptide Name | Sequence ID NO: | Amino acid sequence |
|---|---|---|
| msFibα XH | Sequence ID NO: 33 | L S E G G G V R G P R V V E X H Q S Q C K D |
| msFibα XG | Sequence ID NO: 34 | L S E G G G V X G P R V V E R H Q S Q C K D |
| huFibα XH | Sequence ID NO: 35 | L A E G G G V R G P R V V E X H Q S A C K D |
| huFibα XG | Sequence ID NO: 36 | L A E G G G V X G P R V V E R H Q S A C K D |
| msFibβ XG | Sequence ID NO: 37 | E P T D S L D A X G H R P V D R R |
| msVim XS/XL | Sequence ID NO: 39 | Y V T X S S A V X L X S S V P |

X = citrulline

Figure 4A:
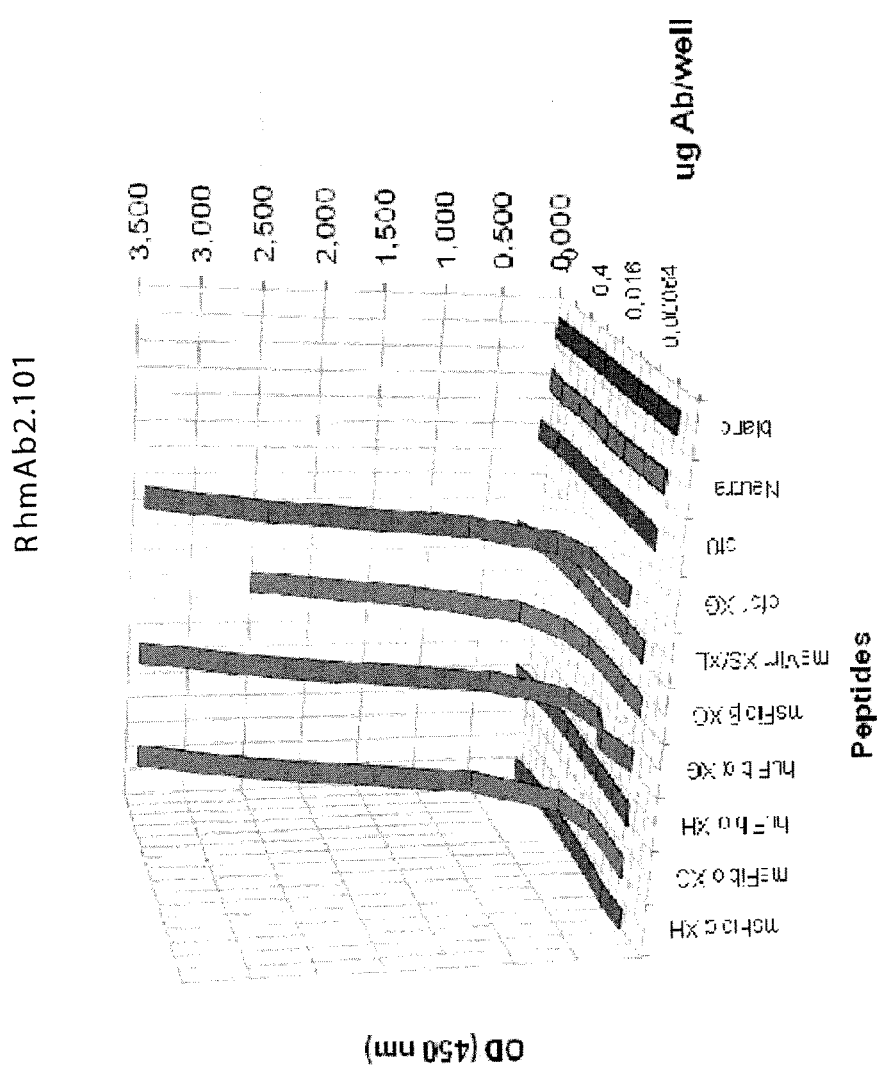
FIGS. 4A and 4B: An enzyme-linked immunosorbent assay (ELISA) was used to test the affinity of RhmAb2.101 (FIG. 4A) and RhmAb2.102 (FIG. 4B) for citrulline-containing peptides derived from fibrinogen and vimentin. Biotin and citrulline-containing peptides derived from fibrinogen and vimentin were immobilized on NEUTRAVI- DIN®-coated 96-well ELISA plates (0.3 µg/well). CFC-1 and CFC-0 were coated at the same concentration and served as positive and negative controls, respectively, for specific anti-citrulline reactivity and as coating controls. Non-coated wells were used to test for aspecific binding of the antibodies. Coated wells were incubated with antibody dilution series ranging from 10 µg/well down to 0.000128 µg/well for 1 hour at RT (z-axis). Detection of bound anti-citrulline antibodies was performed by incubating the wells with rabbit anti-human HRP (1:2000) for 1 hour at RT followed by incubation with TMB substrate. The resulting OD (y-axis) is a measure for antibody binding.
Figure 4B:
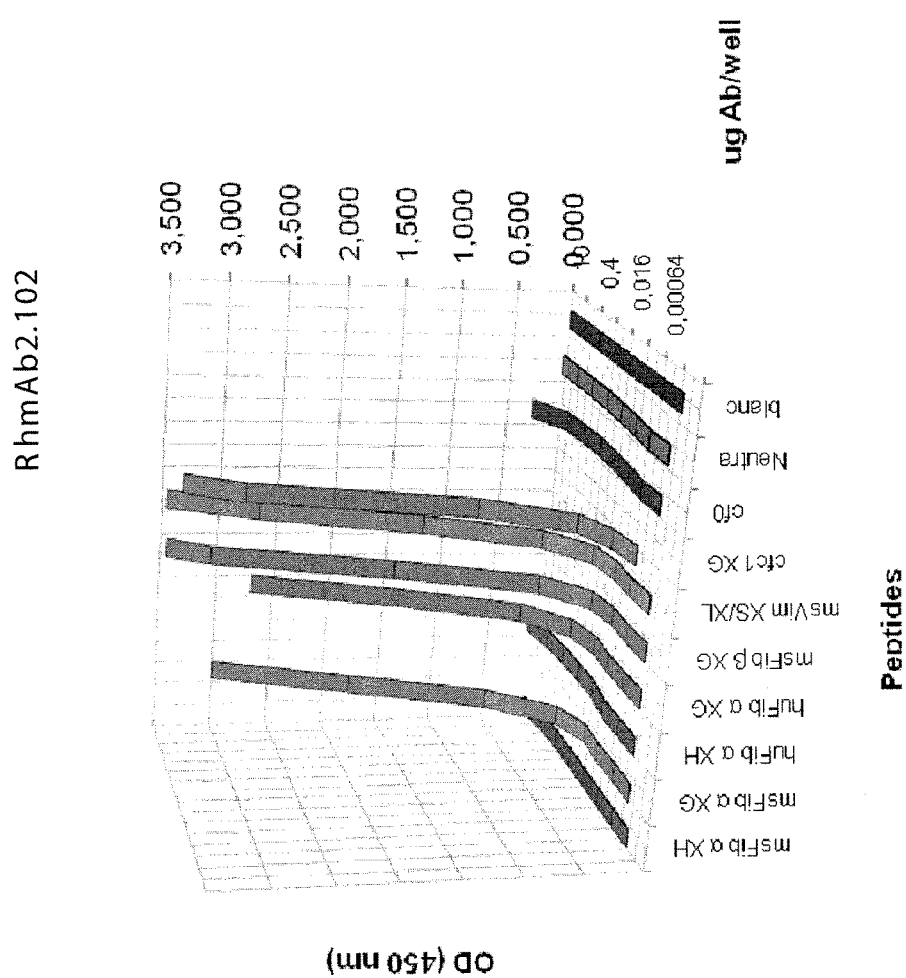

It was observed that the mouse fibrinogen β peptide (SEQ ID NO: 37) is recognized by RhmAb2.101 and RhmAb2.102 (FIG. 4A). Again, RhmAb2.102 showed higher affinity compared to RhmAb2.101 (FIGS. 4A and 4B). Furthermore, only RhmAb2.102 recognized the mouse vimentin peptide (Example 9). It is very likely that besides the above-mentioned peptides, the deiminated epitopes on peptide msFibβ (SEQ ID NO: 37) and msVim (SEQ ID NO: 38) also play a crucial role in the RA inflammatory cascade. However, it is therewith not excluded that other epitopes on fibrinogen and vimentin also play a role in the anti-inflammatory effects of our therapeutic antibodies.

The disclosure, therefore, also relates to a specific binding molecule as described above that is specifically reactive with an epitope on peptides msFibβ or msVim (SEQ ID NO: 37 or SEQ ID NO: 38) and their use.

In addition, it is shown that citrullinated epitopes appear de novo in inflamed tissue. In an experimental mouse model for rheumatoid arthritis, it was shown that citrullinated peptides were immunoprecipitable from the inflamed forepaws of affected mice using human monoclonal antibody 102 (RhmAb2.102).

A typical CAIA experiment was, therefore, performed in which mice (three mice per group) have been injected i.p. with a mixture of eight anti-collagen antibodies (2.8 mg/mouse) on day 0. Three days later, mice received another i.p. injection containing 25 µg LPS. Scoring has been performed as described above. During this experiment, a group of mice were sacrificed each day, and paws were analyzed for citrulline presence by Western blot analysis and immunohistochemical techniques.

For each group of mice, forepaws were pooled and extracts made. Immunoprecipitations (IP) have been performed on these extracts using 20 micrograms RhmAb2.102 per IP. Precipitates have been subjected to SDS-page electrophoreses and transferred to a nitrocellulose membrane by Western blot techniques. The blot was first stained with Ponceau S for total protein detection. Ponceau S staining is performed to verify that for each IP, the same amount of antibody has been used. Pronounced antibody heavy and light chains could be observed in the same amounts.

Subsequently, the citrulline residues present on blot have been chemically modified according to Senshu et al. (Senshu et al., Anal. Biochem., vol. 203, 94-100, 1992). The chemical modification can then be visualized using an antibody that recognizes the chemical modification of citrulline residues (Senshu et al., Anal. Biochem., vol. 203, 94-100, 1992). Deiminated fibrinogen was used as a positive control in this experiment. An immunoprecipitation without extracts was used as a negative control in these experiments.

As from day 4, pronounced bands appeared on the blots at positions corresponding to proteins with molecular weights of 50 kilodaltons, 15 kilodaltons, and 17 kilodaltons. These bands became more pronounced in day 5 and were most intense at day 6.

Figure 5A:
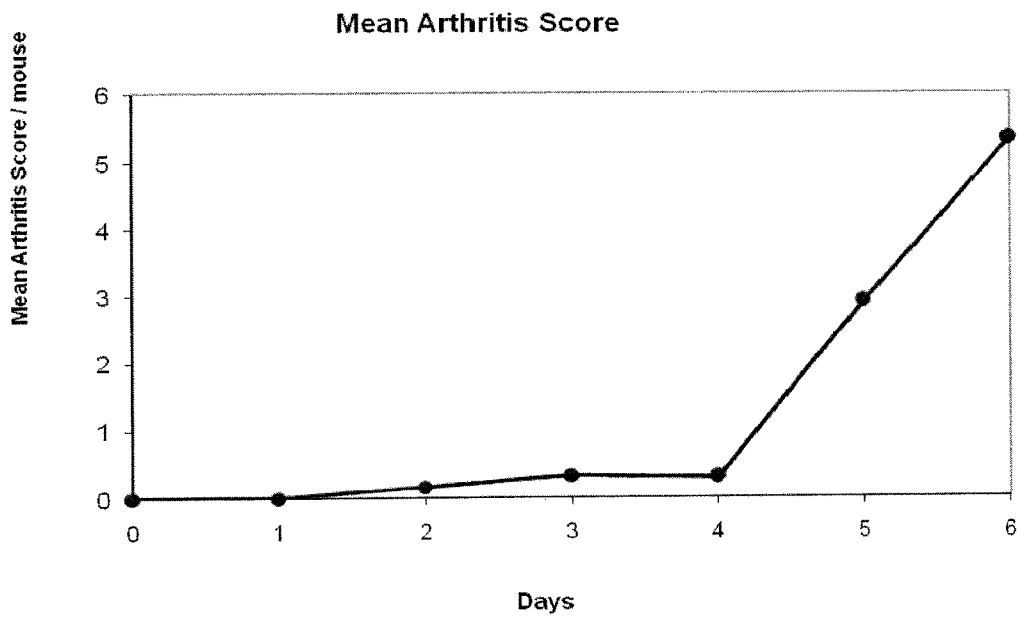
FIGS. 5A and 5B: A collagen antibody-induced arthritis (CAIA) model was used to investigate citrulline appearance in the paws. Groups of three mice were treated at day 0 with 2.8 mg anti-collagen antibodies through i.p. injection, followed by an additional i.p. injection with LPS (25 µg/mouse) on day 3. Mean arthritis score and arthritis incidence are shown in FIGS. 5A and 5B, respectively.
Figure 5B:

The arthritis incidence of the experiment was 100%, with mice having regular arthritis scores, reaching 5+ at day 6 (FIGS. 5A and 5B). The amount of precipitated protein increases in time, which is visible from days 4 to 6. Based on the citrulline specificity of RhmAb2.102 and the presence of the signals on blot obtained with the anti-chemically modified citrulline antibody, it was concluded that mice subjected to CAIA have detectable citrulline levels in their inflamed joints.

In the CAIA experiments described above, anti-citrulline antibodies were injected on day 3 after anti-collagen antibody injection, when inflammation in the paws of mice was still absent or very low. This prevented the occurrence of clinical symptoms and is, therefore, useful as a treatment of inflation, in particular, a prophylactic treatment.

Figure 6A:
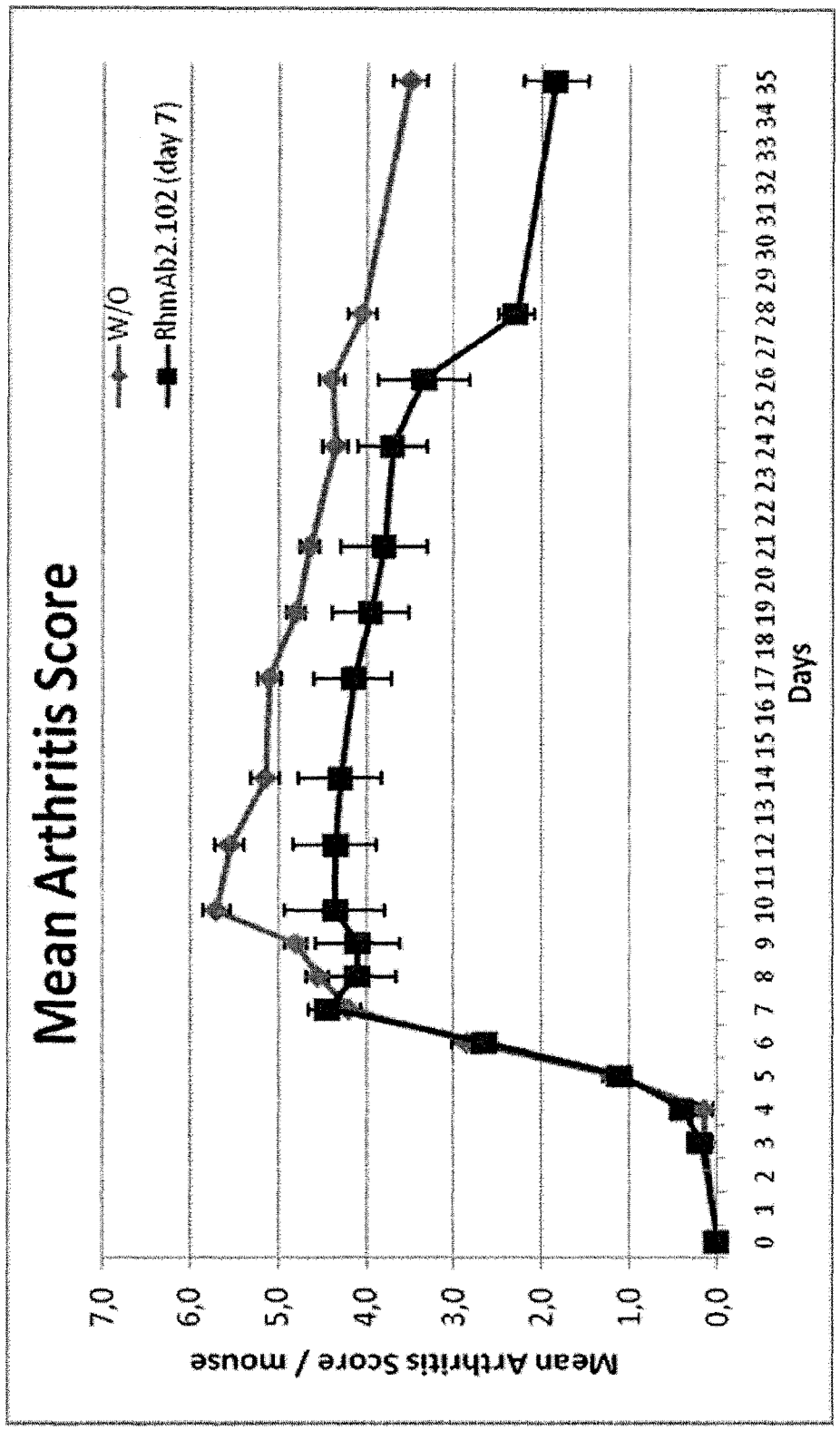
FIGS. 6A and 6B: A collagen antibody-induced arthritis (CAIA) model was used to test the therapeutic effect of RhmAb2.102 when given on day 7 after anti-collagen antibody injection. Mean arthritis score of all paws (FIG. 6A) and mean arthritis score of the right hind paws (FIG. 6B) are indicated. Groups of five mice were treated at day 0 through i.p. injection with 2.8 mg anti-collagen antibodies. LPS (25 µg/mouse) was administered on day 3 through i.p. injection, and RhmAb2.102 (1 mg/mouse) or placebo were injected via the same route at day 7. Animals have been scored daily until day 35. It was observed that RhmAb2.102 at least stabilized the present inflammation.
Figure 6B:
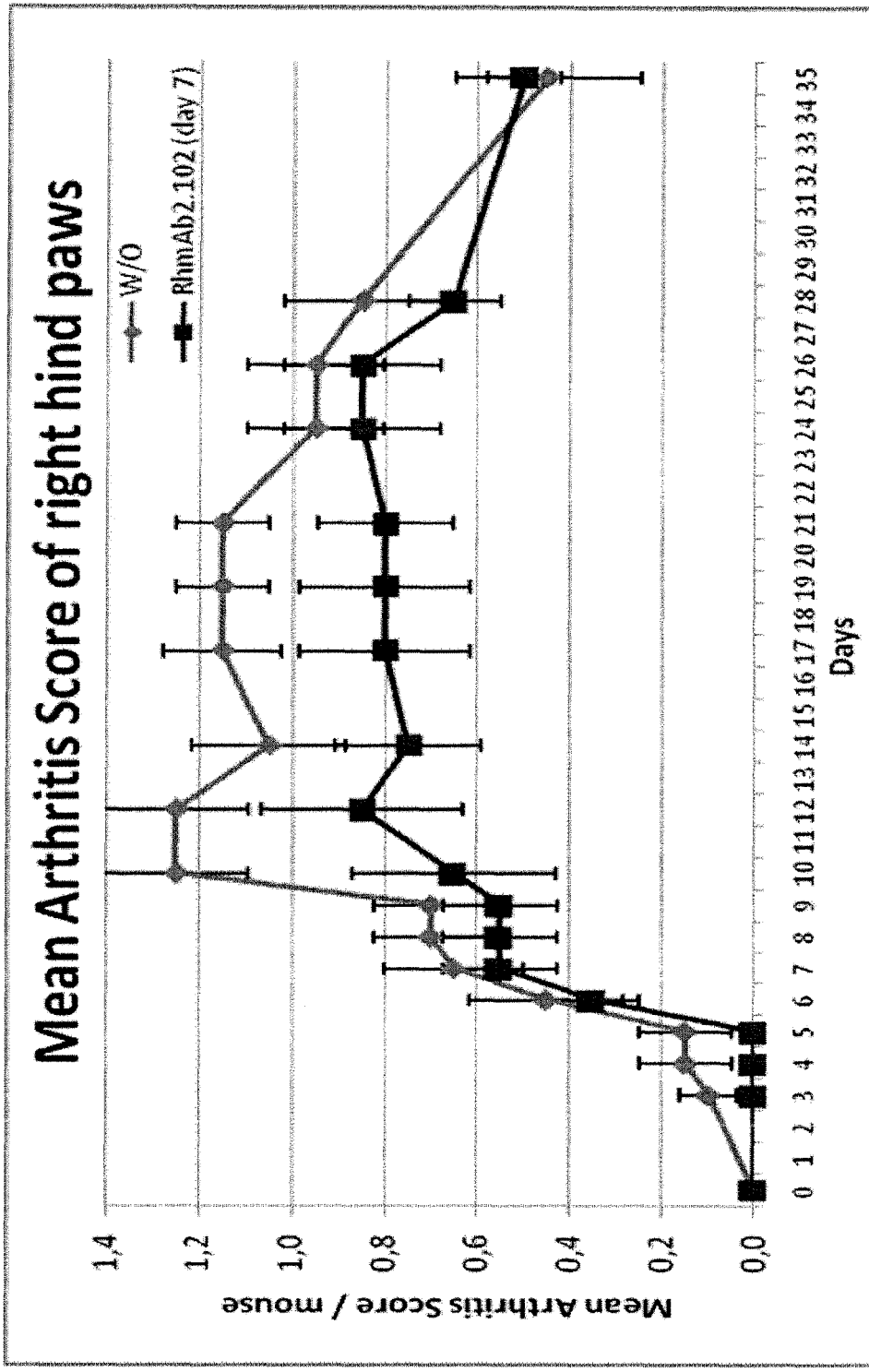

Therefore, it was desired to know if RhmAb2.102 could also cure clinical symptoms once they had occurred. This was done by treating animals on day 7 after anti-collagen injection when mean arthritis scores of all four paws of all mice reached the arbitrary score of approximately 4. As is shown in FIGS. 6A and 6B, RhmAb2.102 does not abolish the swelling observed, but rather stabilized the present inflammation/swelling. Animals were followed for 35 days after which inflammatory scores among placebo and RhmAb2.102-treated mice were equal (FIG. 6B and Example 10). FIG. 6A shows the mean arthritis score of all paws of each group, while FIG. 6B shows the mean arthritis score of the right hind paws of the animals that have been used for histological analysis at day 35.

Figure 7A:
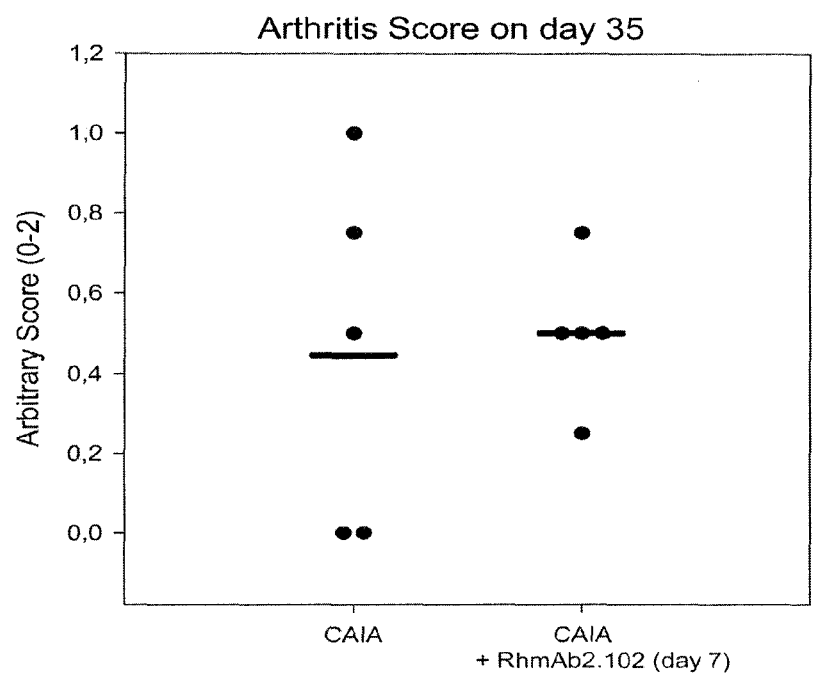
FIGS. 7A-7F: Histological analysis has been performed on Haematoxylin/eosin and safranin O-stained tissue slides of right hind paws of all CAIA animals that have been treated on day 7 with RhmAb2.102 or placebo (FIG. 7). The following parameters have been scored (arbitrary scale of 0-3) on the stained tissue slides: cartilage erosion (FIG. 7B), bone erosion (FIG. 7C), inflammatory cell influx (FIG. 7D), cartilage PG depletion (FIG. 7E), and chondrocyte death (FIG. 7F).
Figure 7B:
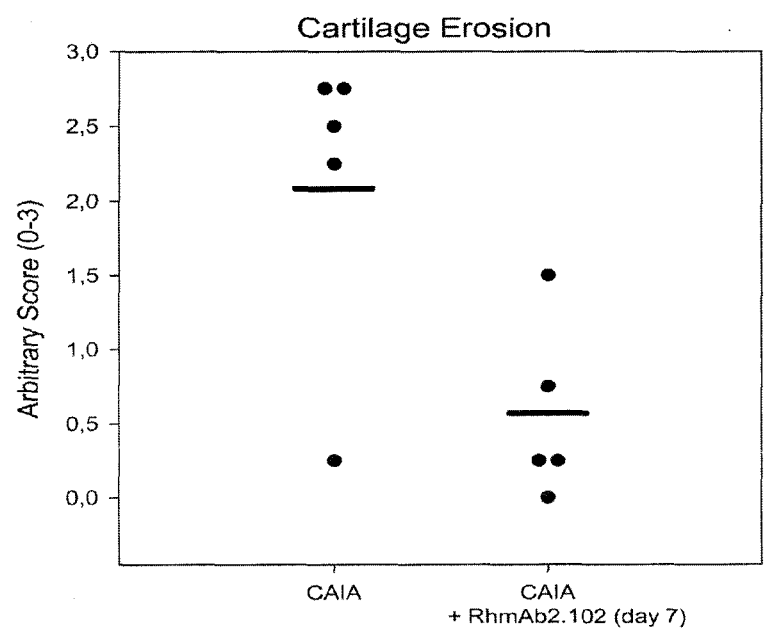

Histology on right hind paws of all animals has been performed in order to investigate whether RhmAb2.102 treatment on day 7 could protect the mice from permanent joint damage (FIGS. 7A-7F). FIG. 7A shows that macroscopical inflammation in the right hind paws between experimental groups on day 35 of the experiment were similar. Most surprisingly, however, all known parameters for joint erosion were decreased. When scoring inflammatory cell influx (FIG. 7D), cartilage erosion (FIG. 7B), cartilage PG depletion (FIG. 7E), chondrocyte death (FIG. 7F) and bone erosion (FIG. 7C), a dramatic decrease is observed in the experimental group that has been treated on day 7 with RhmAb2.102, indicating that RhmAb2.102 has a strong therapeutic potential in regard to preventing joint damage during inflammation (Example 10). The disclosure, therefore, relates to a method for preventing or treating joint damage by administering a binding molecule as described herein to a patient in need of such a treatment.

Figure 8:
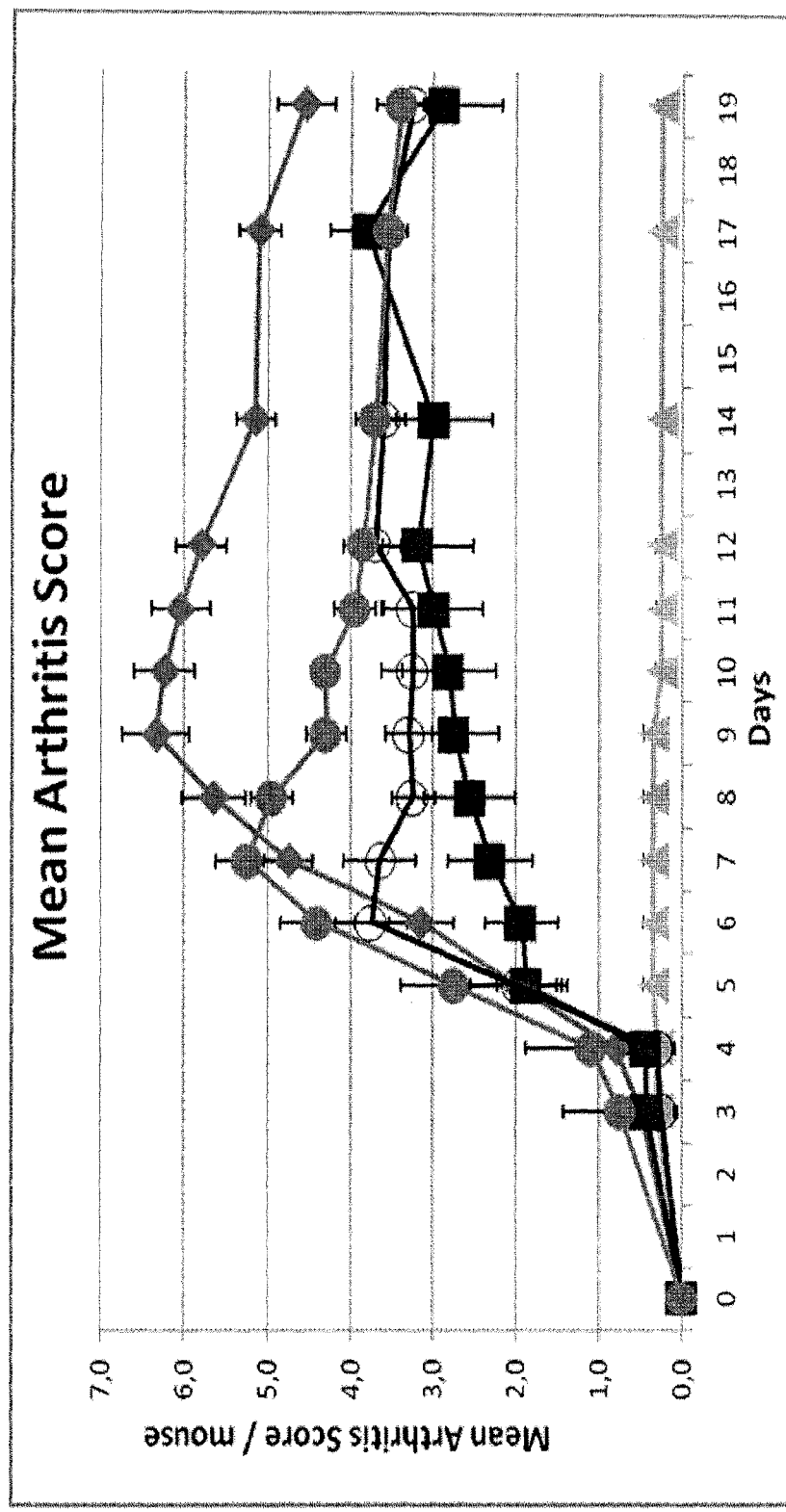
FIG. 8: A collagen antibody-induced arthritis (CAIA) model was used to test the therapeutic effect of RhmAb2.102 when given on days 3, 5, 6 and 7 after injection of anti-collagen antibodies. Groups of five mice were treated at day 0 through i.p. injection with 2.8 mg anti-collagen antibodies. LPS (25 µg/mouse) was administered on day 3 through i.p. injection. RhmAb2.102 (1 mg/mouse) was injected i.v. at days 3, 5, 6 or 7. Animals have been scored daily until day 19. The graph depicts mean arthritis score for each experimental group. It may again be concluded that RhmAb2.102 at least stabilized the inflammation at a level comparable to the level at the start of the therapy. Diamonds: control, Circle: Day 7, Open Circle: Day 6, Square: Day 5 and Triangle: Day 3.

Further CAIA experiments have been performed to investigate the therapeutic effect of RhmAb2.102 treatment on days 5, 6 and 7, respectively (FIG. 8). In this experiment, RhmAb2.102 has been injected i.v. in order to deliver the antibody rapidly to sites of inflammation. In this experiment, prophylactic treatment at day 3 and a non-treated control group have been included. Experimental procedures have been performed as in Example 10 with the only difference being injections with 1 mg RhmAb2.102 per mouse on days 3, 5 and 6. As expected, RhmAb2.102 at day 3 inhibited the inflammatory response. Treating mice with i.v. injections of RhmAb2.102 on days 5, 6 or 7 stabilized the inflammation (FIG. 8) as also seen in FIGS. 6A and 6B. It is noteworthy that the signs of inflammation were not reduced, whereas all parameters for joint erosion were decreased. This shows that joint erosion and inflammation are two separate entities that may be treated separately.

Additional deiminated proteins that preferentially bind to RhmAb2.102 have been identified by mass spectrometry analysis. Furthermore, deiminated proteins that preferentially bind to RhmAb2.102 and not, or with to a lesser extent, to RhmAb2.101 have also been identified by additional mass spectrometry analysis. Human PAD4-deiminated human embryonic kidney cell (HEK293) lysates have been immunoprecipitated with RhmAb2.101 or RhmAb2.102 (Example 11) and subjected to a high throughput nano-LC system coupled to an advanced, high-performance LTQ Fourier transform ion cyclotron resonance mass spectrometer (nLC LTQ FTMS ULTRA) (Example 12). Its ultra-high mass resolution, mass accuracy and sensitivity in combination with exponentially modified protein abundance index (emPAI) calculations enabled us to identify deiminated proteins that (preferentially) bind to RhmAb2.102. This is shown in Table 7 (Examples 11 and 12).

Hence, the disclosure also relates to a binding molecule specifically reactive with any of the proteins or polypeptides as shown in Table 7 for use in the prevention or treatment of an inflammatory disease.

In summary, it has been shown herein that a binding molecule specifically reactive with an epitope on a molecule selected from the group consisting of p15, p17, more in particular, a citrullinated epitope on human PAD4- and/or PAD2-deiminated human histone 2A, a citrullinated epitope on human PAD4-deiminated human histone 4, human PAD2-deiminated human histone H4, human PaD2-deiminated human histone H3, or a protein selected from the group consisting of the proteins of Table 9 and, even more in particular, a peptide according to SEQ ID NO: 21, SEQ ID NO: 24, SEQ ID NO 26, SEQ ID NO: 37 and SEQ ID NO: 38 may be used in the treatment or prevention of inflammatory diseases as specified herein. Whether a given binding molecule is specifically reactive with the above-mentioned molecules, may easily be determined by analysis of the ability of the binding molecule to compete with an antibody selected from the group consisting of RhmAb2.102, RhmAb2.108, RhmAb2.109, RhmAb2.110, RhmAb2.111 and RhmAb2.112, RmmAb22.101, and RmmAb22.102 for binding to an epitope on p15 or p17 or any of the citrullinated epitopes mentioned above.

Having shown the efficacy of the binding composition according to the disclosure, it will now be evident for the skilled person that inflammatory diseases may also be treated or prevented by eliciting an immune response wherein specific binding molecules according to the disclosure are generated in the patient's own body (in vivo). Such an immune response may be generated to prevent inflammatory disease from occurring (prophylaxis, prophylactic vaccines) or to ameliorate or decrease the consequences of an inflammatory disease, i.e., therapy.

Hence, the disclosure also relates to a method for the prevention or treatment of inflammatory diseases by eliciting an immune response in vivo wherein specific binding molecules are generated reactive with an epitope selected from the group consisting of a citrullinated epitope on p15, p17, a citrullinated epitope on human PAD4- and/or PAD2-deiminated human histone 2A, human PAD4- and/or PAD2-deiminated human histone 4, human PAD2-deiminated human histone H3, and a peptide according to SEQ ID NO: 21, SEQ ID NO: 24, SEQ ID NO 26, SEQ ID NO: 37 and SEQ ID NO: 38.

Vaccines or therapeutics according to the disclosure may effectively comprise a citrullinated epitope specifically reactive with a binding molecule according to the disclosure. More in particular, the citrullinated epitope may be a citrullinated epitope on human PAD4- and/or PAD2-deiminated human histone 2A, human PAD4- and/or PAD2-deiminated human histone 4, human PAD2-deiminated human histone H3, or a peptide selected from the group consisting of SEQ ID NO: 21, SEQ ID NO: 24, SEQ ID NO 26, SEQ ID NO: 37 and SEQ ID NO: 38.

Accordingly, a number of citrulline-related inflammatory diseases may be treated or prevented. Hence, the disclosure also relates to a method as described above wherein the inflammatory disease is selected from the group consisting of autoimmune diseases, arthritis, rheumatoid arthritis, osteoarthritis, multiple sclerosis, psoriatic arthritis, psoriasis, Alzheimer's disease, autoimmune hepatitis, juvenile idiopathic arthritis, spondyloarthropathy, Down's syndrome, multiple system atrophy, Parkinson's disease and Lewy body dementia. Particularly preferred is the prevention or treatment of autoimmune diseases such as rheumatoid arthritis.

Since this embodiment of the disclosure relates to an in vivo immune response, a preferred specific binding molecule is an antibody.

The skilled person will be aware of the fact that it is advantageous to use antibodies in the present disclosure that do not, or not completely, activate the immune system, such as T-cell activation or complement activation. It is preferred, therefore, to use an Fc portion of a human IgG4 or IgG2 when the invention is to be practiced in humans.

The peptides and proteins as mentioned herein may also be used as antigens for the detection of specific antibodies in order to diagnose inflammatory diseases, more preferably Rheumatoid Arthritis.

EXAMPLES

Example 1: Recombinant Human and Mouse Monoclonal Antibodies

Monoclonal antibodies against citrullinated antigens of patients with RA were initially selected by means of phage display, as described (Raats et al., *J. Rheumatology*, vol. 30, 1696-711, 2003). Briefly, the autoantibody repertoires of three patients with RA were isolated from their B-cell repertoire, and used to generate antibody fragment libraries. These libraries were subjected to four rounds of affinity selection against citrullinated cyclic peptide CFC1-cyc as described in WO98/22503. Antibody clones were selected based on their strong reactivity with CFC1-cyc and lack of reactivity with the non-citrullinated CFC0-cyc, (WO98/22503).

Antibody coding sequences described by Raats et al. (*J. Rheumatology*, vol. 30, 1696-711, 2003) were synthesized according to Stemmer et al. (*Gene*, vol. 164, 49-53, 1995), and subsequently cloned into mammalian expression vectors coding for human and mouse antibody isotypes. Human antibodies were of the isotype IgG1 lambda and were named RhmAb2.101, RhmAb2.102.

RhmAb2.101 was synthesized according to the protocol of Stemmer et al. (*Gene*, vol. 164, 49-53, 1995) based on the sequence of clone Ra3 (Raats et al., *J. Rheumatology*, vol. 30, 1696-711, 2003) and consists of a VH derived from germline family 3-21, combined with a VL derived from germline family γ1b.

RhmAb2.102 was synthesized according to Stemmer et al. (*Gene*, vol. 164, 49-53, 1995) and comprises an immunoglobulin heavy chain encoded by SEQ ID NO: 8, combined with an immunoglobulin light chain encoded by SEQ ID NO: 9. The immunoglobulin heavy chain encoded by SEQ ID NO: 8 comprises a mouse leader globulin according to SEQ ID NO: 12, followed by the variable antibody heavy chain according to SEQ ID NO: 13, followed by the immunoglobulin constant domain human IgG1 according to SEQ ID NO: 14. The immunoglobulin light chain encoded by SEQ ID NO: 9, comprises a mouse leader globulin according to SEQ ID NO: 12, followed by the variable antibody light chain according to SEQ ID NO: 15 followed by the immunoglobulin human lambda constant domain according to SEQ ID NO: 16.

The primary mRNA sequences of the variable domains (VH and VL) of monoclonal antibody RhmAb2.101 have been published and were deposited in the EMBL database under accession numbers as shown in Table 1. Full size human antibody sequences were generated using identical leader and constant human domains as described for antibody RhmAb2.102.

TABLE 1

*Homo Sapiens* Partial mRNA Database and Accession Numbers

| mAb | Database reference | Accession number | Description |
|---|---|---|---|
| RhmAb2.101 | EMBL: AJ430751 | AJ430751 | *Homo sapiens* partial mRNA for immunoglobulin heavy chain variable region (IGVH gene), clone Ra3 |
| RhmAb2.101 | EMBL: AJ430766 | AJ430766 | *Homo sapiens* partial mRNA for immunoglobulin light chain variable region (IGVL gene), clone Ra3 |

Control antibodies RmmAb13.101, RmmAb13.102 and RmmAb13,103 against citrullinated fibrinogen, and RhmAb2.201 against the apoptotic 40 kD cleavage product of the Human U1-70k protein, were commercially obtained from Modiquest Research BV, Schoutstraat 58, 6525 XV Nijmegen, The Netherlands (Cat no, MQ13.101, MQ13.102, MQ13.103, and MQR2.201).

Example 2: Experimental Model for Inflammation

The commercially available collagen antibody-induced arthritis (CAIA) mouse model from ModiQuest Research B.V. (cat no: MQ18.101) has been used according to manufacturer's specifications to induce arthritis in mice (on the World Wide Web at modiquestresearch.nl/shop/files/18.101-50MG_2007.08.22. pdf). For that purpose, on day 0, male DBA/J1 mice (five to six mice/group) of the age of 8 weeks were injected i.p. with a mix of eight anti-collagen antibodies. (Mice used in FIGS. 1A and 1B received 1.6 mg anti-collagen antibody mix, whereas mice used in FIGS. 1C-1F received 2.4 mg). On day 3, mice received another i.p. injection containing 25 µg LPS mixed with 1 mg anti-citrulline antibodies (unless stated otherwise). LPS triggers the inflammation. Until day 13 of the experiment, animals were scored daily for signs of inflammation in their paws. Scoring has been performed according to Table 2. The maximum arthritis score per animal is 8.

Mouse monoclonal anti-citrulline antibodies RmmAb13.101, RmmAb13.102 and RmmAb13.103 were confirmed to be able to enhance the severity of the collagen antibody-induced arthritis. A mixture of these antibodies had even a more pronounced response. This essentially confirms earlier results that anti-citrulline antibodies are capable of enhancing/inducing arthritis (Kuhn et al., *J. Clin. Invest*, vol. 116, 961-871, 2006; Hill et al., *J. Exp. Med.*, vol. 205, 967-979, 2008). These results are shown in FIGS. 1A and 1B, which shows the "mean arthritis score" and "arthritis incidence," respectively, of the same experiment.

Human monoclonal antibody RhmAb2.102 reduced or even abolished the clinical signs of arthritis in the experimental CAIA model, whereas RhmAb2.101 had no effect at all at the dose tested (FIGS. 1C and 1D).

TABLE 2

Results of Experimentally Induced Arthritis at Approximately Day 4

| | |
|---|---|
| 1-2 Swollen toes | 0.25 |
| 3-4 Swollen toes | 0.50 |
| Slightly swollen footpad or ankle | 0.50-0.75 |
| Swollen footpad or ankle +/− toes | 1.00 |

TABLE 2-continued

Results of Experimentally Induced Arthritis at Approximately Day 4

| | |
|---|---|
| Swollen toes + slightly swollen footpad | 1.25 |
| Swollen toes + swollen footpad | 1.5 |
| Swollen footpad + swollen ankle | 2.00 |

The decision to administer anti-citrulline antibodies on day 3 after anti-collagen antibody injection was based on the data of the experiment described hereinabove, which show that citrullinated epitopes appeared in the paws of mice with experimentally induced arthritis approximately at day 4.

Example 3: Preparation of Deiminated Cell Extract, SDS-Page Electrophoresis and Western Blotting COS-1 cells ($8 \cdot 10^5$) were transiently transfected with 2 µg huPAD2 or huPAD4 expression vector using the AMAXA NUCLEOFECTION® device (program D-005) together with the V-kit, and cells were seeded in 20 ml medium in a T75.

72 hours later, the cells were washed twice with PBS, trypsinized, spun down and resuspended in 15 µl ice cold lysis buffer (20 mM Tris pH 7.4, 10 mM β-mercaptoethanol, 100 mM NaCl, 10% glycerol, protease inhibitors).

The cell samples were sonified four times for 15 seconds on ice. The lysate was centrifuged at 3,000 rpm for 5 minutes and the supernatant transferred to a clean tube. The cell lysate was deiminated for 30 minutes to 2 hours at 37° C. by adding $CaCl_2$ and DTE at a final concentration of 10 mM and 5 mM, respectively. Deiminated cell lysates were stored at −20° C.

10× sample buffer (0.25 M Tris pH 6.8, 8% SDS, 35% glycerol, 2.5% β-mercaptoethanol, bromphenolblue) was added to the deiminated cell lysates and boiled for 5 minutes. Lysate corresponding to approximately $5 \cdot 10^5$ cells was loaded in each lane of an SDS-PAGE (15% gels) and separated, followed by electroblotting to Hybond-C extra nitrocellulose membranes (Amersham Biosciences). Blotting and loading were checked by Ponceau S staining.

Example 4: Therapeutic Anti-Citrulline Antibodies Recognize p15 and p17

Blots as prepared in Example 3 were cut in strips and blocked for 2 hours at RT with 5% (w/v) low-fat dry milk in PBS-TWEEN® (wash buffer) to block all non-specific sites. Blots were then washed five times for 5 minutes with wash buffer and strips were incubated for an additional 1 hour at RT with 4 ml wash buffer containing 20 µg anti-citrulline antibody. Thereafter, the strips were washed five times for 10 minutes with wash buffer, and incubated with a peroxidase-conjugated rabbit anti-human IgG (Dako) (1 hour at RT) in wash buffer (1:2000). Strips where then washed three times for 10 minutes with wash buffer followed by a two-times wash with PBS to wash away all unbound antibody.

Immunoreactive bands were visualized using chemiluminescent substrate (PIERCE), and exposed to Kodak BioMax XAR autoradiography films (Eastman Kodak Company, Rochester, N.Y., USA).

It was observed that strips incubated with RhmAb2.102 showed reactivity with a doublet of proteins with a molecular weight of approximately 15 kilodaltons and 17 kilodaltons.

Example 5: Immunoprecipitation of Antigens

For immunoprecipitation purposes, 20 µg anti-citrulline antibodies together with 30 µL of protein A-Sepharose fast flow (Amersham Biosciences, Uppsala, Sweden) was added to 330 µL cell lysate and incubated 2 hours at 4° C. while rotating. The Sepharose beads with immunobound proteins were subsequently washed four times in IPP150 (10 mM Tris/Hcl pH 8, 150 mM NaCl, 0.1% NP40, 0.1% TWEEN®-20). Two times sample buffer (100 mm Tris-HCl, pH 6.8, 200 mm dithiothreitol, 4% SDS, 0.2% bromophenol blue, 20% glycerol) was added to the beads, and proteins were subjected to 15% SDS-PAGE. The gel was stained overnight at RT in staining solution (10% w/v ammonium sulfate, 2% w/v phosphoric acid (85%), 0.1% w/v CBB G-250, 20% v/v methanol) while gently rocking. All staining trays were sealed with parafilm to prevent methanol evaporation. The next day, background de-staining was performed by incubating the gels in MILLI-Q® H2O until desired staining is visible. The de-staining solution (MILLI-Q® H2O) was replaced two to three times, whereafter, images of the gel were taken.

Immunoprecipitations with RhmAb2.102 on both human PAD2- and PAD4-deiminated COS-1 lysates revealed prominent p15 and p17 protein bands, which could not or hardly be detected in the RhmAb2.101 precipitates. The rate of recognition of p15 and p17 proteins, therefore, correlates well with the therapeutic properties of these antibodies (FIGS. 1A-1D).

Example 6: Mass-Spectrometry Analysis of p15 and p17

The bands at p15 and p17 of the SDS-page gels of Example 3 were excised from the gel and analyzed by MALDI-TOF MS. Briefly, excised gel pieces were washed two times with 50 µl of 25 mM ammonium bicarbonate, and incubated 30 minutes for each washing step. A 15-minute wash was repeated as above with the addition of 30% v/v acetonitrile. All liquid was removed and 25 µl of 25 mM ammonium bicarbonate+25 µl of acetonitrile were added and incubated for 15 minutes. Again, all liquid was removed and gels were incubated 30 minutes with 50 µl of acetonitrile. All liquid was removed and the pieces were dehydrated by incubating for 2 hours at 37° C. After the dehydration, the gel pieces were allowed to swell again by adding 5 µl of trypsin solution (~15 ng trypsin/µl in 25 mM ammonium bicarbonate/5 mM n-octyl-ß-D-glucopyranoside) and incubated on ice for 1 hour. Excess trypsin solution was removed and gel pieces were incubated for 14 hours at 37° C. with 5 µl 25 mM ammonium bicarbonate/5 mM n-octyl-ß-D-glucopyranoside. Peptides were extracted by incubating with 4 µl 50% acetonitrile/0.5% trifluoroacetic acid (TFA)/5 mM n-octyl-ß-D-glucopyranoside for 1 hour at RT. Samples were sonicated for 2 minutes in a sonication water bath, the liquid transferred in a new tube and the extraction step was repeated. The sample was dried in a vacuum centrifuge and subjected to MALDI-TOF MS.

All fragments identified in MALDI-TOF MS analysis were attributable to histone proteins (Table 3).

TABLE 3

| MALDI-TOF data | | |
|---|---|---|
| Description | Peptide | SEQ ID NO: |
| histone cluster 3, H2bb [Mus musculus] | KAMGIMNSFVNDIFERI | SEQ ID NO: 1 |
| histone cluster 3, H2bb [Mus musculus] | RKESYSIYVYKV | SEQ ID NO: 2 |

TABLE 3-continued

MALDI-TOF data

| Description | Peptide | SEQ ID NO: |
|---|---|---|
| similar to histone H2B [Bos taurus] | KAMGIMNSFVNDIFKRI | SEQ ID NO: 3 |
| histone cluster 1, H2bn [Bos taurus] | KAMGNMNSFVNDIFERI | SEQ ID NO: 4 |
| histone cluster 2, H4 [Rattus norvegicus] | RKTVTAMDVVYALKR | SEQ ID NO: 5 |
| histone cluster 2, H4 [Rattus norvegicus] | RDAVTYTEHAKR | SEQ ID NO: 6 |
| histone cluster 2, H4 [Rattus norvegicus] | RISGLIYEETRG | SEQ ID NO: 7 |

Example 7: Therapeutic Anti-Citrulline Antibody RhmAb2.102 Recognizes H2A/p4

Human recombinant histones H1, H2A, H2B, H3 and H4 (100 μg) were incubated 3 hours with or without 53.4 mU huPAD2 or huPAD4 at 37° C. Deiminated as well as non-deiminated histones were coated on 96-well ELISA plates (0.3 μg/well) by overnight incubation at 4° C. Wells were washed five times with PBS-TWEEN®-20 (PBS-T) and blocked by a 1-hour incubation with PBS-T+1% Bovine serum albumin (BSA) at room temperature (RT). After five more washes with PBS-T, wells were incubated for 1 hour at RT with serial dilutions of RhmAb2.101 or RhmAb2.102 in PBS-T+1% BSA starting at a concentration of 10 μg/well. Wells were washed five times with PBS-T and incubated with rabbit anti-human HRP (1:2000) for 1 hour at RT followed by five washes with PBS-T and three wash steps with PBS. Wells incubated with RhmAb2.101 were incubated 15 minutes and wells incubated with RhmAb2.102 were incubated 10 minutes with TMB substrate before stopping the reaction with 2M $H_2SO_4$. Optical density was measured by 450 nm and is a measure for the affinity of the antibodies used.

Example 8: Therapeutic Anti-Citrulline Antibody RhmAb2.102 Recognizes Peptide 1

96-well ELISA plates were coated with NEUTRAVIDIN® (0.1 μg/well) by overnight incubation at 4° C. Wells were washed five times with PBS-TWEEN®-20 (PBS-T) and blocked by a 1-hour incubation with PBS-T+1% Bovine serum albumin (BSA) at room temperature (RT). After five more washes with PBS-T, wells were incubated for 1 hour at RT with histone-derived citrulline and biotin-containing peptides (0.3 μg/well). After another five more washes with PBS-T, wells were incubated for 1 hour at RT with serial dilutions of RhmAb2.101, RhmAb2.102 or RhmAb2.104 in PBS-T+1% BSA starting at a concentration of 10 μg/well. Wells were washed five times with PBS-T and incubated with rabbit anti-human HRP (1:2000) for 1 hour at RT followed by five washes with PBS-T and three wash steps with PBS. Wells were incubated 5 minutes with TMB substrate before stopping the reaction with 2M $H_2SO_4$. Optical density was measured by 450 nm and is a measure for the affinity of the antibodies used.

Example 9: Therapeutic Anti-Citrulline Antibodies Recognize Fibrinogen and Vimentin-Derived Citrulline Peptides 96-well ELISA plates were coated with NEUTRAVIDIN® (0.1 μg/well) by overnight incubation at 4° C. Wells were washed five times with PBS-TWEEN®-20 (PBS-T) and blocked by a 1-hour incubation with PBS-T+1% Bovine serum albumin (BSA) at room temperature (RT). After five more washes with PBS-T, wells were incubated for 1 hour at RT with fibrinogen and vimentin-derived citrulline and biotin-containing peptides (0.3 μg/well). After another five more washes with PBS-T, wells were incubated for 1 hour at RT with serial dilutions of RhmAb2.101 or RhmAb2.102 in PBS-T+1% BSA starting at a concentration of 10 μg/well. Wells were washed five times with PBS-T and incubated with rabbit anti-human HRP (1:2000) for 1 hour at RT followed by five washes with PBS-T and three wash steps with PBS. μg/wells. Wells were incubated 5 minutes with TMB substrate before stopping the reaction with 2M $H_2SO_4$. Optical density was measured by 450 nm and is a measure for the affinity of the antibodies used.

Example 10: Therapeutic Potential of RhmAb2.102

The commercially available collagen antibody-induced arthritis (CAIA) mouse model from ModiQuest Research B.V. (cat no: MQ18.101) has been used according to the manufacturer's specifications to induce arthritis in mice (on the World Wide Web at modiquestresearch.nl/shop/files/18.101-50MG %20_2007.08.22.pdf). For that purpose, on day 0, male DBA/J1 mice (five mice/group) of the age of 8 weeks have been injected i.p. with a mix of eight anti-collagen antibodies (2.8 mg/mouse). On day 3, mice received another i.p. injection containing 25 μg LPS. LPS triggers the inflammation. On day 7 when the mean arthritis score was around 4 (FIG. 6A), one group received an i.v. injection containing 1 mg RhmAb2.102 and the other group received an i.v. injection containing placebo.

Animals were scored daily for signs of inflammation in their paws. Scoring has been performed according to Table 2. The maximum arthritis score per animal is 8. RhmAb2.102 stabilized the inflammation (FIG. 6A).

All right hind paws have been used for histological analysis. Tissue was fixed for 4 days in 4% formaldehyde, decalcified in 5% formic acid, and subsequently dehydrated and embedded in paraffin. Standard frontal sections of 7 μm were mounted on SUPERFROST® slides (Menzel-Gläser, Braunschweig, Germany). Haematoxylin and eosin (H&E) staining was performed to study joint inflammation (cell influx, FIG. 7D). The severity of inflammation in the joints was scored on a scale of 0-3 (0=no cells, 1=mild cellularity, 2=moderate cellularity, and 3=maximal cellularity). FIG. 7A shows the macroscopical inflammation on day 35. To study proteoglycan (PG) depletion from the cartilage matrix (FIG. 7E), sections were stained with safranin O (SO), followed by counterstaining with fast green. Depletion of PG was determined using an arbitrary scale of 0-3, ranging from normal, fully stained cartilage to destained cartilage, fully depleted of PGs. Chondrocyte death (FIG. 7F) was scored on a scale of 0 to 3, ranging from no loss of chondrocyte nuclei to complete empty cartilage surface. Cartilage and bone erosion (FIGS. 7B and 7C) were graded on a scale of 0 to 3, ranging from no damage to complete loss of the cartilage or bone structure. Histopathological changes in the joint were scored on five semi-serial sections of joint spaced 70 μm apart. Scoring was performed blind, without previous knowledge of the experimental conditions.

Figure 7C:
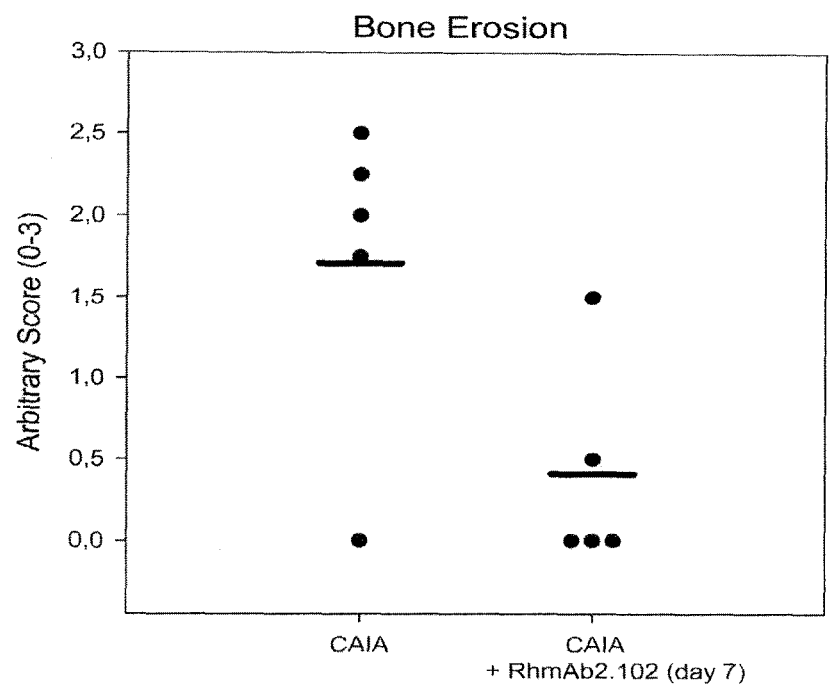
Figure 7D:
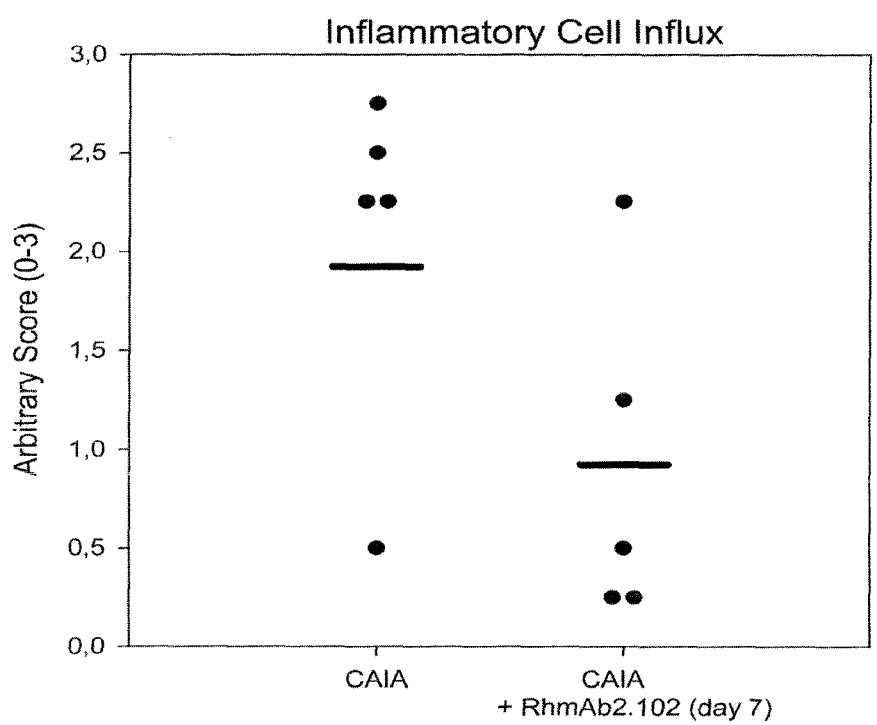
Figure 7E:
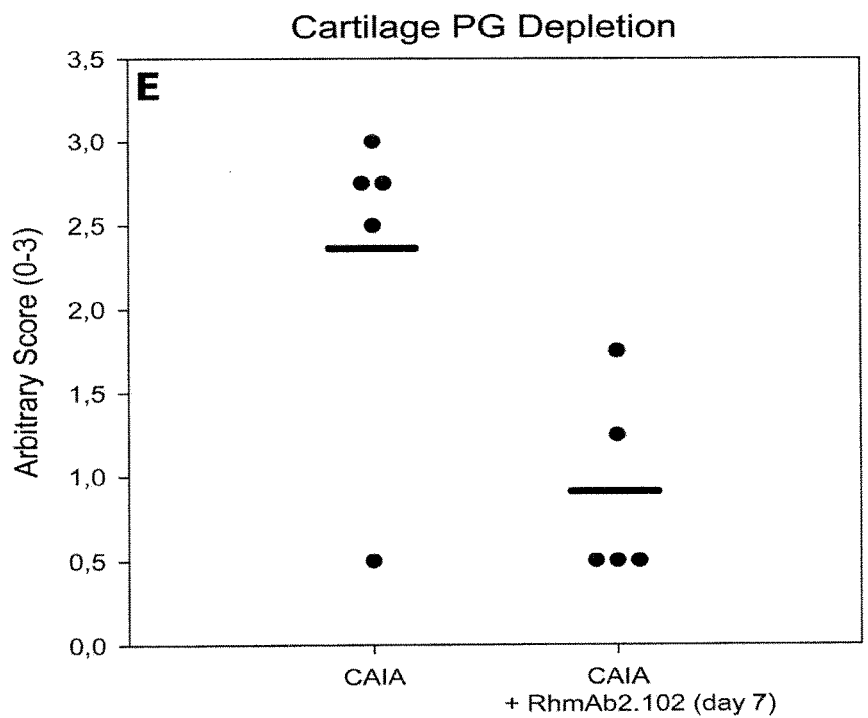
Figure 7F:
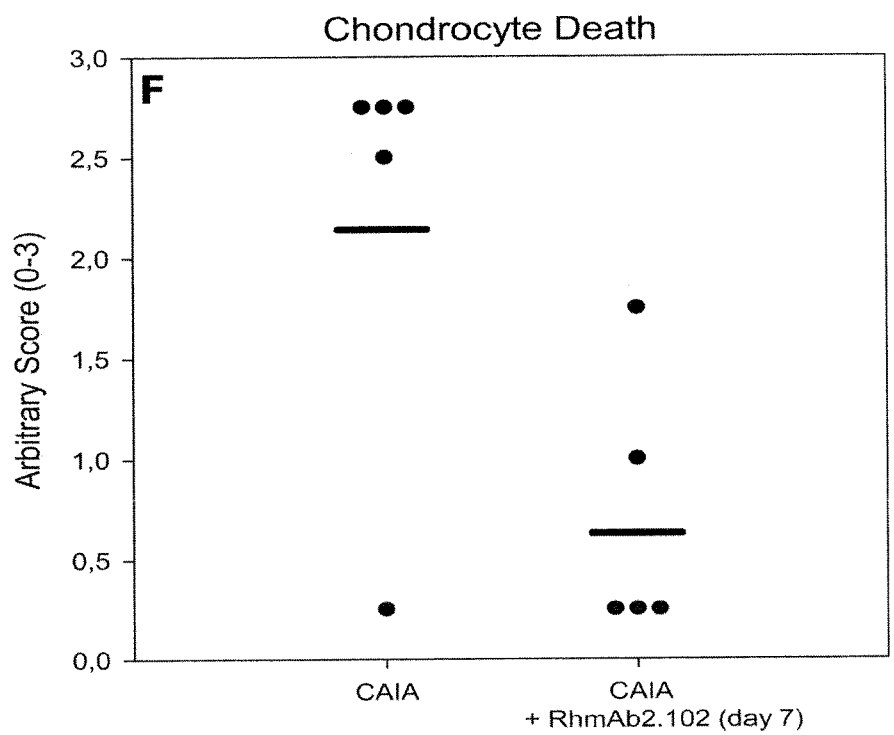

Although macroscopical inflammation in the right hind paws among groups was identical on day 35 (FIGS. 6A and 7A), a dramatic decrease is observed in the experimental group receiving RhmAb2.102 compared to the control group when looking at any of the following parameters for joint erosion: inflammatory cell influx (FIG. 7D), cartilage erosion (FIG. 7B), cartilage PG depletion (FIG. 7E), chondrocyte death (FIG. 7F) and bone erosion (FIG. 7C). This result strongly supports the therapeutic potential of RhmAb2.102.

Example 11: Preparation of huPAD4-Deiminated HEK293 Extract and Immunoprecipitation with RhmAb2.101 or RhmAb2.102

HEK293 cells were harvested, washed once with PBS, spun down, and $5 \cdot 10^5$ cells resuspended in 15 µl ice cold lysis buffer (20 mM Tris pH 7.4, 10 mM β-mercaptoethanol, 100 mM NaCl, 10% glycerol, protease inhibitors).

The cell samples were sonified four times for 15 seconds on ice. The lysate was centrifuged at 3,000 rpm for 5 minutes and the supernatant transferred to a clean tube. The cell lysate was deiminated for 2 hours at 37° C. by adding 1 U human PAD4 per 2 mg of protein (ModiQuest Research B.V.; cat no: MQ16.203), 10 mM CaCl2 and 5 mM DTT.

Deimination of lysates was verified by subjecting the deiminated HEK293 lysates to SDS-Page (12.5% gels) electrophoresis followed by Western blotting. Western blots have been immunostained with antibodies RhmAb2.101 or RhmAb2.102 and found positive. Blots treated with an irrelevant antibody did not show any staining.

Subsequently, immunoprecipitations (IP) have been performed on deiminated HEK293 lysates with antibodies RhmAb2.101 or RhmAb2.102. Briefly, 30 µl Protein A Sepharose Fast Flow were washed five times with 1 ml IPP500 (10 mM Tris/HCl pH 8.0, 500 mM NaCl, 0.1% NP40 and 0.1% TWEEN®-20), and coupled to 20 µg RhmAb2.101, 20 µg RhmAb2.102 or not coupled (negative control). Protein A Sepharose Beads/antibody mixtures have been incubated 1 hour at room temperature under constant rotation. Beads were subjected to three washes with 1 ml IPP500, one wash with 1 ml IPP150 (10 mM Tris/HCl pH 8.0, 150 mM NaCl, 0.1% NP40 and 0.1% TWEEN®-20), and subsequently incubated at room temperature with 300 µl deiminated HEK293 lysate for 2 hours under constant rotation. Beads were washed three times with 1 ml of IPP150, after which a small part has been used for SDS-PAGE electrophoresis to determine if the IP procedure with the HEK293 cells was successful. Immunoprecipitated proteins on RhmAb2.101, RhmAb2.102 and control beads have been eluted with 50 µl elution buffer (100 mM Na citrate pH 3.0), neutralized with 10 µl 1 M Tris/HCl pH 9.04, and stored at −20° C. until nLC LTQ FTMS ULTRA mass spectrometry (Example 12).

Example 12: Mass-Spectrometry Analysis of RhmAb2.101 and RhmAb2.102 Immunoprecipitated huPAD4-Deiminated HEK293 Proteins To remove PEGs from the immunoprecipitated proteins, they were loaded on a 15% SDS-PAGE gel and run shortly. The proteins were cut out of the gel and in-gel digested with trypsin as described in Example 6. Samples were diluted 50-fold before subjecting them to nLC LTQ FTMS ULTRA analysis.

Peptide and protein identifications were extracted from the data by means of the search program Mascot, using the NCBInr_20081022 database with *Homo sapiens* taxonomy. The following modifications were allowed in the search: carbamidomethylation of cysteines (C) (fixed), oxidation of methionine (M) (variable) and deamidation of asparagine (N), arginine (R) and glutamine (Q) (variable). Deimination could not be used as a search tool. This problem could be eliminated since deamidation and deimination result both in 1 dalton mass difference if compared to non-modified arginines.

Protein identification validation was performed by an in-house developed script. Briefly, the software classifies protein identifications based on the number of uniquely identified peptide sequences, clusters proteins sharing the same set of peptides and validates the proteins with the following criteria:

Proteins with 1 peptide must have a peptide score greater than 49

Proteins with more than 1 peptide must have a peptide score greater than 29

With the validation criteria used, peptides have been identified in all three samples (sample 1: HEK293 precipitate with RhmAb2.101; sample 2: HEK293 precipitate with Rhm2.102; and sample 3: HEK293 precipitate with empty beads).

The exponentially modified protein abundance index (emPAI) was calculated for all validated proteins. The emPAI provides approximate, label-free, relative quantitation of the proteins in a mixture based on protein coverage by the peptide matches in a database search result. This technique enabled identification of deiminated proteins that (preferentially) bind to RhmAb2.102. This is shown in Table 9.

TABLE 9 nLC LTQ FTMS ULTRA data

| Protein ID | Protein | Ratio 102/101 |
| --- | --- | --- |
| gi\|4503841\|ref\|NP_001460.1\| | ATP-dependent DNA helicase II, 70 kDa subunit [*Homo sapiens*] | ~ |
| gi\|4504279\|ref\|NP_002098.1\| | H3 histone, family 3A [*Homo sapiens*] | ~ |
| gi\|4504263\|ref\|NP_003512.1\| | H2B histone family, member E [*Homo sapiens*] | ~ |
| gi\|16306566\|ref\|NP_003518.2\| | histone H2B [*Homo sapiens*] | ~ |
| gi\|10800130\|ref\|NP_066409.1\| | histone 1, H2ad [*Homo sapiens*] | ~ |
| gi\|4501955\|ref\|NP_001609.1\| | poly (ADP-ribose) polymerase family, member 1 [*Homo sapiens*] | ~ |
| gi\|60097902\|ref\|NP_002007.1\| | filaggrin [*Homo sapiens*] | ~ |
| gi\|13399298\|ref\|NP_064455.1\| | immunoglobulin lambda-like polypeptide 1 isoform a precursor [*Homo sapiens*] | ~ |
| gi\|113414893\|ref\|XP_001127175.1\| | PREDICTED: similar to lactotransferrin [*Homo sapiens*] | ~ |
| gi\|62122917\|ref\|NP_001014364.1\| | filaggrin 2 [*Homo sapiens*] | ~ |
| gi\|4557581\|ref\|NP_001435.1\| | fatty acid binding protein 5 (psoriasis-associated) [*Homo sapiens*] | ~ |

TABLE-continued 9 nLC LTQ FTMS ULTRA data

| Protein ID | Protein | Ratio 102/101 |
| --- | --- | --- |
| gi\|13775212\|ref\|NP_112583.1\| | polyamine modulated factor 1 binding protein 1 [Homo sapiens] | ~ |
| gi\|21614544\|ref\|NP_002955.2\| | S100 calcium-binding protein A8 [Homo sapiens] | ~ |
| gi\|4758170\|ref\|NP_004397.1\| | deleted in malignant brain tumors 1 isoform a precursor [Homo sapiens] | ~ |
| gi\|4503143\|ref\|NP_001900.1\| | cathepsin D preproprotein [Homo sapiens] | ~ |
| gi\|77539758\|ref\|NP_001029249.1\| | histone cluster 2, H4b [Homo sapiens] | 30.2 |
| gi\|4501883\|ref\|NP_001604.1\| | alpha 2 actin [Homo sapiens] | 3.2 |
| gi\|12056468\|ref\|NP_068831.1\| | junction plakoglobin [Homo sapiens] | 2.8 |
| gi\|4501885\|ref\|NP_001092.1\| | beta actin [Homo sapiens] | 2.7 |
| gi\|58530840\|ref\|NP_004406.2\| | desmoplakin isoform I [Homo sapiens] | 2.2 |
| gi\|57864582\|ref\|NP_001009931.1\| | hornerin [Homo sapiens] | 1.7 |
| gi\|74136883\|ref\|NP_114032.2\| | heterogeneous nuclear ribonucleoprotein U isoform a [Homo sapiens] | 1.0 |
| gi\|34419635\|ref\|NP_002146.2\| | heat shock 70 kDa protein 6 (HSP70B') [Homo sapiens] | 1.0 |
| gi\|50845388\|ref\|NP_001002858.1\| | annexin A2 isoform 1 [Homo sapiens] | 1.0 |
| gi\|113425263\|ref\|XP_001133831.1\| | PREDICTED: similar to 60S ribosomal protein L29 (Cell surface heparin-binding protein HIP) [Homo sapiens] | 1.0 |
| gi\|4885431\|ref\|NP_005337.1\| | heat shock 70 kDa protein 1B [Homo sapiens] | 0.8 |
| gi\|117190254\|ref\|NP_001070911.1\| | heterogeneous nuclear ribonucleoprotein C isoform b [Homo sapiens] | 0.7 |
| gi\|32483416\|ref\|NP_066554.2\| | neurofilament, heavy polypeptide 200 kDa [Homo sapiens] | 0.7 |
| gi\|4506629\|ref\|NP_000983.1\| | ribosomal protein L29 [Homo sapiens] | 0.5 |
| gi\|5729877\|ref\|NP_006588.1\| | heat shock 70 kDa protein 8 isoform 1 [Homo sapiens] | 0.5 |
| gi\|4503471\|ref\|NP_001393.1\| | eukaryotic translation elongation factor 1 alpha 1 [Homo sapiens] | 0.5 |
| gi\|16751921\|ref\|NP_444513.1\| | dermcidin preproprotein [Homo sapiens] | 0.4 |
| gi\|4502027\|ref\|NP_000468.1\| | albumin precursor [Homo sapiens] | 0.4 |
| gi\|34098946\|ref\|NP_004550.2\| | nuclease sensitive element binding protein 1 [Homo sapiens] | 0.0 |

Example 13: Generation/Selection of a Family of Anti-Inflammatory Antibodies

Human-derived scFv libraries were panned against PAD2- or PAD4-deiminated forms of human histone 2A, histone 4, peptide 1 (AAASGXGKQGGK, SEQ ID NO: 21) and against CFC-1 peptide in a similar method as described in Raats et al., 2003 (J. M. H. Raats, E. W. Wijnen, G. J. M. Pruijn, F. H. M. Van den Hoogen, and W. J. van Venrooij. 2003. J. Rheum. 30, 1696-1711).

Selected antibodies that showed citrulline-dependent reactivity with CFC-1 and/or peptide 1 (AAASGXG-KQGGK, SEQ ID 21) and/or PAD-deiminated histone 2A and/or histone 4, were screened for reactivity against an array of citrullinated proteins and/or peptides derived thereof (Example 12, Table 9), against PAD2- and PAD4-deiminated human histone isoforms, and against deiminated human histone-derived peptides. Concomitantly, immunoprecipitation was performed on PAD2- and PAD4-deiminated human cell extracts and synovial fluid from RA patients.

Antibodies that immunoprecipitated bands p15 and/or p17, and/or antibodies with ELISA reactivity profiles against citrullinated epitopes (PAD2- and PAD4-deiminated human histone isoforms, and/or CFC-1 and/or peptide 1 (AAAS-GXGKQGGK, SEQ ID 21, and/or citrullinated epitopes derived from proteins listed in nine comparable with RhmAb2.102, were subsequently cloned into human IgG1 format. Full-size human IgG antibodies were tested for their prophylactic and/or therapeutic anti-inflammatory potential in a CAIA mouse model, as described herein.

This screening procedure yielded antibodies with prophylactic and/or therapeutic anti-inflammatory potential in the CAIA mouse model with high frequency.

Examples of novel antibodies selected according to the above method are RhmAb2.108, RhmAb2.109, RhmAb2.110, RhmAb2.111 and RhmAb2.112, are disclosed herein in SEQ ID NO: 17, SEQ ID NO: 18, SEQ ID NO: 39, SEQ ID NO: 20, SEQ ID NO: 41, SEQ ID NO: 40. SEQ ID NO: 19, SEQ ID NO: 43, and SEQ ID NO: 42. The RhmAb2.110 immunoglobulin light chain encoded by SEQ ID NO: 10 comprises a mouse leader globulin according to SEQ ID NO: 12, followed by the variable antibody light chain according to SEQ ID NO: 41, followed by the immunoglobulin human kappa constant domain according to SEQ ID NO: 11.

Subsequently, the collagen antibody-induced arthritis (CAIA) model was used to test the anti-inflammatory effect of RhmAb2.108, RhmAb2.109, RhmAb2.110, RhmAb2.111 and RhmAb2.112, compared to RhmAb2.102. For this purpose, all antibodies were produced transiently in HEK293 cells. Groups of three DBA/J1 mice were treated at day 0 with i.p. injection of 2.8 mg anti-collagen antibodies (MQ18.101). LPS (25 µg/mouse) as well as RhmAb2.108, RhmAb2.109, RhmAb2.110, RhmAb2.111, RhmAb2.112, and RhmAb2.102 (1 mg/mouse) and placebo were administered via i.p. injection on day 3. All animals have been scored for inflammation daily until day 10.

In this experiment, all novel generated antibodies showed a better anti-inflammatory response compared to RhmAb2.102, RhmAb2.1109, RhmAb2.110, completely abolished inflammation, whereas RhmAb2.112, nearly abolished, and RhmAb2.111, and RhmAb2.108 strongly reduced the signs of inflammation in the tested animals. FIG. 9.

Example 14: Mouse Monoclonal Antibodies

Antibodies against a synthetic citrulline-containing peptide according to the invention have been raised in DBA/J1 mice. At day 125 after start of the immunization process, serum samples were taken and analyzed for a citrulline-specific antigen response. All mice showed an antigen-specific serum titer at the time points tested.

In order to produce hybridoma cell lines, spleens have been dissected after the last boost, splenocytes were harvested from the spleen and fused with a mouse myeloma cell line (NS-1) according to ModiQuest B.V. procedures. Antibody specificity in hybridoma supernatants have been screened on citrulline-containing antigen as well as on the non-citrullinated equivalent.

This resulted in the hybridoma clones (DSMZ Accession no ACC 3031 and ACC 3032), producing RmmAb22.101 and RmmAb22.102, respectively; SEQ ID NO 44 and SEQ ID NO 45.

Subsequently, the collagen antibody-induced arthritis (CAIA) model was used to test the anti-inflammatory effect of RmmAb22.101 and RmmAb22.102 compared to RhmAb2.102. Groups of three DBA/J1 mice were treated at day 0 with i.p. injection of 2.8 mg anti-collagen antibodies (MQ18.101). LPS (25 µg/mouse) as well as RmmAb22.101, RmmAb22.102 and RhmAb2.102 (6 mg/mouse) and placebo were administered via i.p. injection on day 3. All animals have been scored for inflammation daily until day 10.

RhmAb2.102, RmmAb22.101 and RmmAb22.102 antibodies completely protected the mice against inflammation in their paws (FIG. 10).

Example 15: Novel Therapeutic Anti-Citrulline Antibodies Display Similar Recognition Patterns to Citrullinated Epitopes Compared toRhmAb2.102

Similar to the experiments described in Examples 7 and 8, the newly generated antibodies RhmAb2.108, RhmAb2.109, RhmAb2.110, RhmAb2.111, RhmAb2.112, RmmAb22.101, and RmmAb22.102 were analyzed in ELISA for their reactivity on various deiminated targets compared to RhmAb2.102.

Human recombinant histones H1, H2A, H2B, H3 and H4 (100 µg) were deiminated as described in Example 7.

Deiminated, as well as non-deiminated, histones were coated on 96-well ELISA plates (0.3 µg/well) by overnight incubation at 4° C.

Next to the deiminated histones, antibodies were also tested in a set of biotinylated peptides, both in their citrullinated as well as non-citrullinated forms. Coating of peptides was performed as described in Example 8.

All coated wells were washed five times with PBS-TWEEN®-20 (PBS-T) and blocked by a 1-hour incubation with PBS-T+1% Bovine serum albumin (BSA) at room temperature (RT). After five more washes with PBS-T, wells were incubated for 1 hour at RT with serial dilutions of the antibodies in PBS-T+1% BSA starting at a concentration of 2.5 µg/well. Wells were washed five times with PBS-T and incubated with rabbit anti-human HRP (1:2000) for 1 hour at RT followed by five washes with PBS-T and three wash steps with PBS. Stain 10 minutes with TMB substrate before stopping the reaction with 2M $H_2SO_4$. Optical density was measured by 450 nm and is a relative measure for the affinity of the antibodies used. This showed clearly that all therapeutic antibodies have a highly similar staining pattern compared to the therapeutic antibody RhmAb2.102. Only the mouse monoclonals show no reactivity with the Cfc1-peptide. All therapeutic antibodies have very high reactivity with the peptide according to SEQ ID NO: 21, as well as with histone 2A/p2 histone 2A/p4, and histone 4/p2, and show slight reactivity with histone 3/p2.

What is claimed is:

1. A method for treating a subject, the method comprising:
   administering to a subject an antibody;
   wherein the antibody specifically reacts with a citrullinated epitope present on a peptide with an amino acid sequence according to SEQ ID NO:21; and
   wherein the subject suffers from rheumatoid arthritis.

2. A method for treating a subject, the method comprising:
   administering to a subject an antibody;
   wherein the antibody specifically reacts with a citrullinated epitope present on a peptide with an amino acid sequence according to SEQ NO:21;
   wherein the subject suffers from rheumatoid arthritis; and
   wherein the antibody comprises:
   a heavy chain CDR1 domain comprising the polypeptide encoded by positions 76-99 of SEQ ID NO: 44;
   a heavy chain CDR2 domain comprising the polypeptide encoded by positions 151-174 of SEQ ID NO: 44;
   a heavy chain CDR3 domain comprising the polypeptide encoded by positions 289-333 of SEQ ID NO: 44;
   a light chain CDR1 domain comprising the polypeptide encoded by positions 79-111 of SEQ ID NO: 45;
   a light chain CDR2 domain comprising the polypeptide encoded by positions 163-171 of SEQ ID NO: 45; and
   a light chain CDR3 domain comprising the polypeptide encoded by positions 280-306 of SEQ ID NO: 45.

3. A method for treating a subject with rheumatoid arthritis, the method comprising:
   administering to the subject a therapeutically effective amount of an antibody;
   wherein the antibody specifically reacts with a citrullinated epitope present on a peptide with an amino acid sequence according to SEQ ID NO:21.

4. The method according to claim 3, wherein the antibody comprises:
   a heavy chain CDR1 domain comprising the polypeptide encoded by positions 76-99 of SEQ ID NO: 44;
   a heavy chain CDR2 domain comprising the polypeptide encoded by positions 151-174 of SEQ ID NO: 44;
   a heavy chain CDR3 domain comprising the polypeptide encoded by positions 289-333 of SEQ ID NO: 44;
   a light chain CDR1 domain comprising the polypeptide encoded by positions 79-111 of SEQ ID NO: 45;
   a light chain CDR2 domain comprising the polypeptide encoded by positions 163-171 of SEQ ID NO: 45; and
   a light chain CDR3 domain comprising polypeptide encoded by positions 280-306 of SEQ ID NO: 45.

* * * * *